US008257954B2

(12) United States Patent
Clark et al.

(10) Patent No.: US 8,257,954 B2
(45) Date of Patent: *Sep. 4, 2012

(54) GENERATION OF MODIFIED POLYMERASES FOR IMPROVED ACCURACY IN SINGLE MOLECULE SEQUENCING

(75) Inventors: Sonya Clark, Oakland, CA (US); Arek Bibillo, Cupertino, CA (US); Paul Peluso, San Carlos, CA (US); Fred Christians, Los Altos Hills, CA (US); Molly He, Palo Alto, CA (US); Insil Park, Fremont, CA (US); Harold Lee, Sunnyvale, CA (US); Keith Bjornson, Newark, CA (US); Lei Jia, Palo Alto, CA (US); Robin Emig, Belmont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/384,112

(22) Filed: Mar. 30, 2009

(65) Prior Publication Data
US 2010/0112645 A1 May 6, 2010

Related U.S. Application Data

(60) Provisional application No. 61/072,645, filed on Mar. 31, 2008, provisional application No. 61/094,843, filed on Sep. 5, 2008.

(51) Int. Cl.
C12N 9/12 (2006.01)
C12P 19/34 (2006.01)
(52) U.S. Cl. .................. 435/194; 435/183; 435/91.1
(58) Field of Classification Search .................. None
See application file for complete search history.

(56) References Cited

U.S. PATENT DOCUMENTS

| | | | |
|---|---|---|---|
| 5,001,050 A | 3/1991 | Blanco et al. |
| 5,198,543 A | 3/1993 | Blanco et al. |
| 5,328,824 A | 7/1994 | Ward et al. |
| 5,409,811 A | 4/1995 | Tabor et al. |
| 5,476,928 A | 12/1995 | Ward et al. |
| 5,576,204 A | 11/1996 | Blanco et al. |
| 5,723,584 A | 3/1998 | Schatz |
| 5,874,239 A | 2/1999 | Schatz |
| 6,165,765 A | 12/2000 | Hong et al. |
| 6,399,320 B1 | 6/2002 | Markau et al. |
| 6,399,335 B1 | 6/2002 | Kao et al. |
| 6,447,724 B1 | 9/2002 | Jensen et al. |
| 6,610,486 B1 | 8/2003 | Dahlhauser |
| 6,762,048 B2 | 7/2004 | Williams |
| 6,787,308 B2 | 9/2004 | Balassbramanian et al. |
| 6,917,726 B2 | 7/2005 | Levene et al. |
| 6,936,702 B2 | 8/2005 | Williams et al. |
| 7,033,764 B2 | 4/2006 | Korlach et al. |
| 7,041,812 B2 | 5/2006 | Kumar et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,057,026 B2 | 6/2006 | Barnes et al. |
| 7,315,019 B2 | 1/2008 | Turner et al. |
| 7,405,281 B2 | 7/2008 | Xu et al. |
| 2003/0044781 A1 | 3/2003 | Korlach et al. |
| 2003/0124576 A1 | 7/2003 | Kumar et al. |
| 2006/0051807 A1 | 3/2006 | Fuller |
| 2006/0063173 A1 | 3/2006 | Williams et al. |
| 2007/0036511 A1 | 2/2007 | Lunduist et al. |
| 2007/0077564 A1 | 4/2007 | Roitman et al. |
| 2007/0188750 A1 | 8/2007 | Lunduist et al. |
| 2007/0196846 A1 | 8/2007 | Hanzel et al. |
| 2007/0206187 A1 | 9/2007 | Lunduist et al. |
| 2008/0030628 A1 | 2/2008 | Lunduist et al. |
| 2008/0108082 A1 | 5/2008 | Rank et al. |
| 2008/0212960 A1 | 9/2008 | Lundquist et al. |
| 2008/0299565 A1 | 12/2008 | Schneider et al. |
| 2009/0029385 A1 | 1/2009 | Christians et al. |
| 2009/0181396 A1 | 7/2009 | Luong et al. |
| 2009/0208961 A1 | 8/2009 | Bjornson et al. |
| 2009/0280538 A1 | 11/2009 | Patel et al. |
| 2009/0298075 A1 | 12/2009 | Travers et al. |
| 2010/0075332 A1 | 3/2010 | Patel et al. |

(Continued)

FOREIGN PATENT DOCUMENTS
WO    WO 2002/086088 A2    10/2002
(Continued)

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004.*
Arndt et al. (2001) "Insight into the Catalytic Mechanism of DNA Polymerase β: Structures of Intermediate Complexes." *Biochemistry*, 40: 5368-5375.
Arnold et al. (2004) "Polivirus RNA-dependent RNA polymerase(3pol): pre-ready-state kinetic analysis of ribonucleotide incorporation in the presence ofMn2+." *Biochemistry*, 43(18): 5138-5148.

(Continued)

*Primary Examiner* — Richard Hutson
(74) *Attorney, Agent, or Firm* — Quine Intellectual Property Law Group, P.C.; Monicia Elrod-Erickson; Robert Reamey

(57) ABSTRACT

Provided are compositions comprising modified recombinant polymerases that exhibit branching fractions that are less than the branching fractions of the polymerases from which they were derived, or branching fractions that are less than about 25% for a phosphate-labeled nucleotide analog. Also provided are compositions comprising modified recombinant polymerases that exhibit closed polymerase/DNA complexes with increased stability relative to the parental polymerases. Also provided are compositions comprising modified recombinant polymerases that exhibit decreased rate constants relative to the parental polymerases. Provided are methods for generating polymerases with the aforementioned phenotypes. Provided are methods of using such polymerases to make a DNA or to sequence a DNA template.

12 Claims, 20 Drawing Sheets

U.S. PATENT DOCUMENTS

| | | | |
|---|---|---|---|
| 2010/0093555 | A1 | 4/2010 | Bjornson et al. |
| 2010/0112645 | A1 | 5/2010 | Clark et al. |
| 2010/0261185 | A1 | 10/2010 | Nikiforov |
| 2011/0014612 | A1 | 1/2011 | Hendricks et al. |
| 2011/0189659 | A1 | 8/2011 | Clark et al. |

FOREIGN PATENT DOCUMENTS

| | | | |
|---|---|---|---|
| WO | WO 2007/075987 | A2 | 7/2007 |
| WO | WO 2007/076057 | A2 | 7/2007 |
| WO | WO 2007/123763 | A2 | 11/2007 |
| WO | WO 2007/137060 | A2 | 11/2007 |
| WO | WO 2008/051530 | A3 | 5/2008 |
| WO | WO 2008/154317 | A2 | 12/2008 |
| WO | WO 2009/102470 | A1 | 8/2009 |
| WO | WO 2009/145828 | A2 | 12/2009 |

OTHER PUBLICATIONS

Bakhtina et al. (2005) "Use of Viscogens, dNTPaS, and Rhodium (III) as Probes in Stopped-Flow Experiments to Obtain New Evidence for the Mechanism of Catalysis by DNA Polymerase." *Biochemistry*, 44(13): 5177-5187.

Berman, et al. (2007) "Structures of phi29 polymerase complexed with substrate: the mechanism of translocation in polymerases." *EMBO Journal* 26: 3494-3505.

Blanco and Salas (1995) "Mutational Analysis of Bacteriophage φ29 DNA Polymerase." *Methods in Enzymology*, 262: 283-294.

Blasco et al. (1993) "φ29 DNA Polymerase Active Site." *The Journal of Biological Chemistry*, 268(22): 16763-16770.

Castro et al. (2007) "Two proton transfers in the transition state for nucleotidyl transfer catalyzed by RNA and DNA-dependent RNA and DNA polymerase." *Proceedings of the National Academy of Sciences*, USA, 104(11): 4267-4272.

Eid et al. (2009) "Real-time DNA sequencing from single polymerase molecules." *Science*, 323(5910): 133-138.

Korlach et al. (2008) "Long, Processive Enzymatic DNA Synthesis Using 100% Dye-Labeled Terminal Phosphate-Linked Nucleotides." *Nucleosides, Nucleotides and Nucleic Acids*, 27(9): 1072-1083.

Korlach et al. (2008) "Selective aluminum passive for targeted immobilization of single DNA polymerase molecules in zero-mode waveguide nanostructures." *Proceedings of the National Academy of Sciences*, USA, 105(4): 1176-1181, Aug. 18, 2011.

Levene et al. (2003) "Zero-Mode Waveguides for Single-Molecule Analysis at High Concentrations." *Science*, 299: 682-686.

Lundquist et al. (2008) "Parallel confocal detection of single molecules in real time." *Optics Letters*, 33(9): 1026-1028.

Miyake et al. (2008) "Real-Time Imaging of Single-Molecule Flourescence with a Zero-Mode Waveguide for the Analysis of Protein-Protein Interaction." *Analytical Chemistry* 80(15): 6018-6022.

Nicholson et al. (1988) "Enhanced protein thermostability from designed mutations that interact with alpha-helix dipoles." *Nature*, 336: 651-656.

Rechkunova et al. (2000) Thermostable DNA polymerase from Thermus thernophilus B35: influence of divalent metal ions on the interaction with deoxynucleoside triphosphates. *Biochemistry*, 65(5): 609-614.

Soengas et al. (1992) "Site-directed mutagenesis at the Exo III motif of φ29 DNA polymerase; overlapping structural domains for the 3'-5' exonuclease and strand-displacement activities." *The EMBO Journal*, 11(11): 4227-4237.

Tang et al. (2008) "Mismatched dNTP Incorporation by DNA Polymerase β does not Proceed via Globally Different Conformational Pathways," *Nucleic Acids Research*, 36(9): 2948-2957.

Tock et al. (2003) "Dynamic evidence for metal ion catalysis in the reaction mediated by a flap endonuclease." *The EMBO Journal*, 22(5): 995-1004.

Truniger et al. (2002) "A positively charged residue of φ29 DNA polymerase, highly conserved in DNA polymerases from families A and B, is involved in binding the incoming nucleotide." *Nucleic Acids Research*, 30(7): 1483-1894.

Xie et al. (1999) "Single-Molecule Enzymology." *Journal of Biological Chemistry*, 274(23): 15967-15970.

Zhou et al. (2007) "Kinetic Analysis of Sequential Multistep Reactions." *J Phys Chem B*. 111: 13600-13610.

EP Search Report dated Aug. 12, 2011 from corresponding EP Application No. 09755183.2.

International Search Report and Written Opinion dated Aug. 31, 2011 from corresponding International Application No. PCT/US2010/002659.

Invitation to Pay Additional Fees dated Jun. 23, 2011 from corresponding International Application No. PCT/US2010/002659.

Alba (2001) "Protein Family Review: Replicative DNA Polymerases" Genome Biology 2(1): reviews 3002.1-3002.4.

Anand, V. S. and S. S. Patel (2006). "Transient state kinetics of transcription elongation by T7 RNA polymerase." J Biol Chem 281(47): 35677-85.

Augustin et al. (2001) "Progress towards single-molecule sequencing: enzymatic synthesis of nucleotide-specifically labeled DNA" J. Biotechnol. 86:289-301.

Bernad et al. (1989) "A conserved 3'→5' exonuclease active site in prokaryotic and eukaryotic DNA polymerase," Cell, 59:219-228.

Blasco et al. (1993) "Φ29 DNA polymerase active site," J. Biol. Chem., 268(32):24106-24113.

Burgers et al. (2001) "Eukaryotic DNA polymerases: proposal for a revised nomenclature" J Biol Chem. 276(47): 43487-90.

Dahlberg, M. E. and S. J. Benkovic (1991). "Kinetic mechanism of DNA polymerase I (Klenow fragment): identification of a second conformational change and evaluation of the internal equilibrium constant." Biochemistry 30(20): 4835-4843.

De Vega et al. (1996) "Primer-terminus stabilization at the 3'-5' exonuclease active site of Φ29 DNA polymerase. Involvement of two amino acid residues highly conserved in proofreading DNA polymerases," EMBO. J., 15(5):1182-1192.

De Vega et al. (1997) "An invariant lysine residue is involved in catalysis at the 3'-5' exonuclease active site of eukaryotic-type DNA polymerases," J. Mol. Biol., 270:65-78.

De Vega et al. (2010) "Improvement of φ29 DNA polymerase amplification performance by fusion of DNA binding motifs" Proc Natl Acad Sci USA 107(38):16506-16511.

Gardner and Jack (1999) "Determinants of nucleotide sugar recognition in an archaeon DNA polymerase" Nucleic Acids Research 27(12):2545-2553.

Gardner et al. (2004) "Comparative Kinetics of Nucleotide Analog Incorporation by Vent DNA Polymerase" J. Biol. Chem. 279(12):11834-11842.

GenBank Accession No. P03680 "RecName: Full=DNA polymerase; AltName: Full=Early protein GP2," (May 31, 2011).

Giller et al. (2003) "Incorporation of reporter molecule-labeled nucleotides by DNA polymerases. I. Chemical synthesis of various reporter group-labeled 2'-deoxyribonucleoside5'-triphosphates" Nucleic Acids Res. 31(10):2630-2635.

Hsieh, J. C., S. Zinnen, et al. (1993). "Kinetic mechanism of the DNA-dependent DNA polymerase activity of human immunodeficiency virus reverse transcriptase." J Biol Chem 268(33): 24607-13.

Hübscher et al. (2002) "Eukaryotic DNA Polymerases" Annual Review of Biochemistry vol. 71: 133-163.

Ibbara et al. (2009) "Proofreading dynamics of a processive DNA polymerase," Embo J., 28(18):2794-2802.

Johnson (1986) "Rapid kinetic analysis of mechanochemical adenosinetriphosphatases" Methods Enzymol. 134:677-705.

Kamtekar et al. (2004) "Insights into strand displacement and processivity from the crystal structure of the protein-primed DNA polymerase of bacteriophage Φ29" Mol. Cell 16(4): 609-618.

Kamtekar et al. (2006) "The Φ29 DNA polymerase:protein-primer structure suggests a model for the initiation to elongation transition" EMBO J. 25(6):1335-43.

Korlach et al. (2010) "Real-Time DNA Sequencing from Single Polymerase Molecules" Methods in Enzymology 472:431-455.

Lagunavicius et al. (2008) "Duality of polynucleotide substrates for Phi29 DNA poylmerase: 3' → 5' RNase activity of the enzyme," RNA, 14(3):503-513.

Meijer et al. (2001) "Φ29 Family of Phages" Microbiology and Molecular Biology Reviews, 65(2):261-287.

Nicholson et al. (1991) "Analysis of the Interaction between Charged Side Chains and the α-Helix Dipole Using Designed Thermostable Mutants of Phage T4 Lysozyme" Biochemistry 30:9816-9828.

Patel, S. S., I. Wong, et al. (1991). "Pre-steady-state kinetic analysis of processive DNA replication including complete characterization of an exonuclease-deficient mutant." Biochemistry 30(2): 511-25.

Pérez-Arnaiz et al. (2010) "ϕ29 DNA Polymerase Active Site: Role of Residue Val250 as Metal-dNTP Complex Ligand and in Protein-Primed Initiation" J. Mol. Biol. 395:223-233.

Ried et al. (1992) "Simultaneous visualization of seven different DNA probes by in situ hybridization using combinatorial fluorescence and digital imaging microscopy" Proc. Natl Acad. Sci. USA, 89:1388-1392.

Rodriguez et al. (2003) "Φ29 DNA polymerase residue Phe128 of the highly conserved (S/T)Lx₂h motif is required for a stable and functional interaction with the terminal protein," J. Mol. Biol. 325:85-97.

Rodriguez, et al. (2005) "A specific subdomain in Φ29 polymerase confers both processivity and strand-displacement capacity" Proc Natl Acad Sci USA 102(18): 6407-6412.

Steitz (1999) "DNA polymerases: structural diversity and common mechanisms" J Biol Chem 274(25):17395-17398.

Steitz, T. A. (2004). "The structural basis of the transition from initiation to elongation phases of transcription, as well as translocation and strand separation, by T7 RNA polymerase." Curr Opin Struct Biol 14(1): 4-9.

Steitz, T. A. (2006). "Visualizing polynucleotide polymerase machines at work." EMBO J 25(15): 3458-68.

Steitz, T. A. and Y. W. Yin (2004). "Accuracy, lesion bypass, strand displacement and translocation by DNA polymerases." Philos Trans R Soc Lond B Biol Sci 359(1441): 17-23.

Tonon et al. (2000) "Spectral karyotyping combined with locus-specific FISH simultaneously defines genes and chromosomes involved in chromosomal translocations" Genes, Chromosomes and Cancer 27:418-423.

Truniger et al. (2004) "Two positively charged residues of Φ29 DNA polymerase, conserved in protein-primed DNA polymerases, are involved in stabilisation of the incoming nucleotide," J. Mol. Biol., 335:481-494.

Truniger, et al. (2004) "Function of the C-terminus of Φ29 DNA polymerase in DNA and terminal protein binding" Nucleic Acids Research 32(1): 361-370.

Tsai and Johnson (2006) "A new paradigm for DNA polymerase specificity" Biochemistry 45(32):9675-9687.

Vaisman, A., H. Ling, et al. (2005). "Fidelity of Dpo4: effect of metal ions, nucleotide selection and pyrophosphorolysis." EMBO J 24(17): 2957-2967.

Washington, M. T., L. Prakash, et al. (2001). "Yeast DNA polymerase η utilizes an induced-fit mechanism of nucleotide incorporation." Cell 107(7): 917-927.

Yu et al. (1994) "Cyanine dye dUTP analogs for enzymatic labeling of DNA probes" Nucleic Acids Res. 22(15):3226-3232.

Zhu and Waggoner (1997) "Molecular mechanism controlling the incorporation of fluorescent nucleotides into DNA by PCR" Cytometry, 28:206-211.

Zhu et al. (1994) "Directly labeled DNA probes using fluorescent nucleotides with different length linkers" Nucleic Acids Res. 22(16):3418-3422.

\* cited by examiner no product with inhibitor

SEQUENCE LISTING

<160> NUMBER OF SEQ ID NOS: 5

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365
```

```
Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
            450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 76
<212> TYPE: DNA
<213> ORGANISM: Artificial
<220> FEATURE:
<223> OTHER INFORMATION: synthetic oligonucleotide

<400> SEQUENCE: 2
acgacgttga caataataca agtccgatac atgataatta ccgataagtt cgtcgagagc      60
acattaggct ggctgg                                                      76

<210> SEQ ID NO 3
<211> LENGTH: 55
<212> TYPE: DNA
<213> ORGANISM: Artificial
<220> FEATURE:
<223> OTHER INFORMATION: synthetic oligonucleotide

<400> SEQUENCE: 3
ccagccagcc taatgtgctc tcgacgaact tatcggtaat tatcatgtat cggac           55

<210> SEQ ID NO 4
<211> LENGTH: 34
<212> TYPE: DNA
<213> ORGANISM: Artificial
<220> FEATURE:
<223> OTHER INFORMATION: synthetic oligonucleotide

<400> SEQUENCE: 4
ggtgatgtag ataggtggta ggtggtgtca gatc                                  34

<210> SEQ ID NO 5
```

```
<211> LENGTH: 54
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (25)..(25)
<223> OTHER INFORMATION: n is iAmMC6T, an Int amino modified C6 dT
      labeled with alexa fluor 488

<400> SEQUENCE: 5
acgacgttga caataatacg gatcngacac cacctaccac ctatctacat cacc            54
```

GENERATION OF MODIFIED POLYMERASES FOR IMPROVED ACCURACY IN SINGLE MOLECULE SEQUENCING

CROSS-REFERENCE TO RELATED APPLICATIONS

This application is a non-provisional utility patent application claiming priority to and benefit of the following prior provisional patent application: U.S. Ser. No. 61/072,645, filed Mar. 31, 2008, entitled "GENERATION OF POLYMERASES WITH IMPROVED CLOSED COMPLEX STABILITY AND DECREASED BRANCHING RATE" by Sonya Clark et al., which is incorporated herein by reference in its entirety for all purposes. This application also claims priority to and benefit of provisional patent application U.S. Ser. No. 61/094,843, filed Sep. 5, 2008, entitled "ENGINEERING POLYMERASES FOR MODIFIED INCORPORATION PROPERTIES" by Pranav Patel et al.

FIELD OF THE INVENTION

The invention relates to modified DNA polymerases for single molecule sequencing. The polymerases include modified recombinant polymerases that display a reduction in the formation of branching fraction during single molecule sequencing for various nucleotide analogs, modified polymerases that display increased stability of closed polymerase-DNA complexes and enhanced polymerase processivity, and modified polymerases that exhibit one or more slow steps in their catalytic cycle. The invention also relates to methods for determining the sequence of nucleic acid molecules using such polymerases.

BACKGROUND OF THE INVENTION

DNA polymerases replicate the genomes of living organisms. In addition to this central role in biology, DNA polymerases are also ubiquitous tools of biotechnology. They are widely used, e.g., for reverse transcription, amplification, labeling, and sequencing, all central technologies for a variety of applications such as nucleic acid sequencing, nucleic acid amplification, cloning, protein engineering, diagnostics, molecular medicine, and many other technologies.

Because of the significance of DNA polymerases, they have been extensively studied. This study has focused, e.g., on phylogenetic relationships among polymerases, structure of polymerases, structure-function features of polymerases, and the role of polymerases in DNA replication and other basic biology, as well as ways of using DNA polymerases in biotechnology. For a review of polymerases, see, e.g., Hübscher et al. (2002) "Eukaryotic DNA Polymerases" Annual Review of Biochemistry Vol. 71: 133-163, Alba (2001) "Protein Family Review: Replicative DNA Polymerases" Genome Biology 2(1): reviews 3002.1-3002.4, Steitz (1999) "DNA polymerases: structural diversity and common mechanisms" J Biol Chem 274:17395-17398, and Burgers et al. (2001) "Eukaryotic DNA polymerases: proposal for a revised nomenclature" J Biol Chem. 276(47): 43487-90. Crystal structures have been solved for many polymerases, which often share a similar architecture. The basic mechanisms of action for many polymerases have been determined.

A fundamental application of DNA technology involves various labeling strategies for labeling a DNA that is produced by a DNA polymerase. This is useful in DNA sequencing, microarray technology, SNP detection, cloning, PCR analysis, and many other applications. Labeling is often performed in various post-synthesis hybridization or chemical labeling schemes, but DNA polymerases have also been used to directly incorporate various labeled nucleotides in a variety of applications, e.g., via nick translation, reverse transcription, random priming, amplification, the polymerase chain reaction, etc. See, e.g., Giller et al. (2003) "Incorporation of reporter molecule-labeled nucleotides by DNA polymerases. I. Chemical synthesis of various reporter group-labeled 2'-deoxyribonucleoside-5'-triphosphates" *Nucleic Acids Res.* 31(10): 2630-2635, Augustin et al. (2001) "Progress towards single-molecule sequencing: enzymatic synthesis of nucleotide-specifically labeled DNA" *J. Biotechnol.* 86:289-301, Tonon et al. (2000) "Spectral karyotyping combined with locus-specific FISH simultaneously defines genes and chromosomes involved in chromosomal translocations" *Genes Chromosom. Cancer* 27:418-423, Zhu and Waggoner (1997) "Molecular mechanism controlling the incorporation of fluorescent nucleotides into DNA by PCR." *Cytometry,* 28:206-211, Yu et al. (1994) "Cyanine dye dUTP analogs for enzymatic labeling of DNA probes" *Nucleic Acids Res.,* 22:3226-3232, Zhu et al. (1994) "Directly labeled DNA probes using fluorescent nucleotides with different length linkers" *Nucleic Acids Res.* 22:3418-3422, and Reid et al. (1992) "Simultaneous visualization of seven different DNA probes by in situ hybridization using combinatorial fluorescence and digital imaging microscopy" *Proc. Natl Acad. Sci. USA,* 89:1388-1392.

DNA polymerase mutants have been identified that have a variety of useful properties, including altered nucleotide analog incorporation abilities relative to wild-type counterpart enzymes. For example, Vent$^{A488L}$ DNA polymerase can incorporate certain non-standard nucleotides with a higher efficiency than native Vent DNA polymerase. See Gardner et al. (2004) "Comparative Kinetics of Nucleotide Analog Incorporation by Vent DNA Polymerase" *J. Biol. Chem.,* 279(12), 11834-11842 and Gardner and Jack "Determinants of nucleotide sugar recognition in an archaeon DNA polymerase" *Nucleic Acids Research,* 27(12) 2545-2553. The altered residue in this mutant, A488, is predicted to be facing away from the nucleotide binding site of the enzyme. The pattern of relaxed specificity at this position roughly correlates with the size of the substituted amino acid side chain and affects incorporation by the enzyme of a variety of modified nucleotide sugars.

Additional modified polymerases, e.g., modified polymerases that display improved properties useful for single molecule sequencing (SMS) and other polymerase applications (e.g., DNA amplification, sequencing, labeling, detection, cloning, etc.), are desirable. The present invention provides new DNA polymerases with improved kinetic properties including reduced branching fraction formation, increased stability of closed polymerase-DNA complexes and increased processivity, and reduced rates for one or more steps in the catalytic cycle. Also included are methods of making such polymerases, methods of using such polymerases, and many other features that will become apparent upon a complete review of the following.

SUMMARY OF THE INVENTION

Modified DNA polymerases can find use in such applications as, e.g., single-molecule sequencing (SMS), genotyping analyses such as SNP genotyping using single-base extension methods, and real-time monitoring of amplification, e.g., RT-PCR. The invention provides compositions comprising modified recombinant polymerases that exhibit properties, e.g., decreased formation of branching fraction during polymerization, increased closed polymerase/DNA complex stability, and/or decreased reaction rate constants, which can be particularly desirable for these applications. These improved properties can improve polymerase processivity and/or facilitate readout accuracy. Also provided by the invention are methods of generating such modified polymerases and methods in which such polymerases can be used to, e.g., sequence a DNA template and/or make a DNA.

In one aspect, the invention provides compositions that include a modified recombinant DNA polymerase that exhibits a branching fraction that is less than about 25% for a phosphate-labeled nucleotide analog. The branching fraction is the proportion of cognate nucleotide (or nucleotide analog, e.g., A488dA4P) dissociation events from the polymerase active site to the total number of events, e.g., the sum of the incorporation events and dissociation events for the cognate nucleotide or analog. The polymerase of these compositions also exhibits a branching fraction that is less than a branching fraction for the analog exhibited by a parental polymerase, e.g., a wild-type or previously available mutant (e.g., exonuclease deficient) polymerase. The modified recombinant polymerase can be a modified recombinant Φ29-type DNA polymerase that comprises at least one mutation relative to the parental polymerase other than a T368D, T368E, or T368G substitution, where the numbering for the amino acid positions of the mutated residues is relative to that of the wild-type Φ29 polymerase. The compositions comprising a modified recombinant polymerase that exhibits a reduced branching fraction phenotype can optionally include the phosphate-labeled nucleotide analog, which can optionally comprise a fluorophore. The nucleotide analog of the compositions can optionally comprise from 3-7 phosphate groups.

The modified recombinant polymerase of the compositions described above can optionally exhibit a branching fraction of less than about 20%, less than about 15%, less than about 10%, less than about 5%, less than about 1% or even less than about 0.1% of the total interactions, e.g., association events and dissociation events, of the phosphate-labeled nucleotide analog, e.g., A488dA4P, with the nucleotide binding site of the polymerase. In comparison, a wild type Φ29 polymerase exhibits a branching fraction of about ≧40% for, e.g., a gamma-linked A488dA4P nucleotide analog, wherein ≧40% of the total events with a cognate gamma-linked A488dA4P nucleotide analog in the polymerase binding pocket are dissociation events. Alternately or additionally, the recombinant polymerases herein can exhibit a branching fraction that is less than 0.5× as high as a wild type parental polymerase (e.g., a wild type Φ29). Preferably, the branching fraction is about 0.25× as high as the parental polymerase or less, e.g., about 0.15× as high or less.

Optionally, the polymerase can exhibit a $K_m$ for the phosphate-labeled nucleotide analog that is less than a $K_m$ observed for a wild-type polymerase. This is particularly useful in applications in which the polymerase incorporates the analog, e.g., during SMS. For example, the modified recombinant polymerase can exhibit a Km for the phosphate-labeled nucleotide analog that is less than 75%, less than 50%, or less than 25% that of wild-type or parental polymerase such as a wild type Φ29). In one specific class of examples, the polymerases of the invention have a $K_m$ of about 10 µM or less for a non-natural nucleotide analog such as a phosphate-labeled analog.

The modified recombinant polymerase of the compositions described above can optionally be a modified recombinant Φ29-type DNA polymerase. Optionally, the polymerase can be a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. The polymerase can optionally comprise at least one amino acid substitution or combination of substitutions including: an amino acid substitution at position 153; an amino acid substitution at position 191; an amino acid substitution at position 388; an amino acid substitution at position 422; an amino acid substitution at position 128; an amino acid substitution at position 253; an amino acid substitution at position 504; an amino acid substitution at position 143; an amino acid substitution at position 183; an amino acid substitution at position 236; an amino acid substitution at position 363; P153L; G191A; T368F; T368P; T368S; T368V; T368N; T368A; T373N; T373V; T373C; I378V; I378F; K379S; K379A; S388A; S388T; K422R; F128M; F128V; I504V; K143D; K512R; Q183S; R236N; L253A; F363Y; L253A, F363Y, and L480M; T368F, K379S, E375Y, and K512Y; T368F and K379S; T368G and K379S; T368F and T373A; E375Y, K512Y and K379S; E375Y, K512Y and T368F; T368F and V514K; T368F and K379T; S388A and P153L; E375Y, K512Y and T368G; T368G and T373A; E375W and T368G; I378K and K379S; T368F and I378K; T368G and I378K; T368G and V514K; E375W and K379T; T373A and K379S; E375W and T373A; E375Y, K512Y and T373A; E375W and I378K; E375Y, K512Y and I378K; T373A and V514K; T373A and I378K; E375Y, K512Y and K379T; I378K and V514K; E375W and V514K; T368G and K379T; and/or E375Y, K512Y and V514K, where the numbering for the amino acid positions of the mutated residues is relative to that of the wild-type Φ29 polymerase. The modified recombinant polymerase of the compositions described above can optionally further comprise an amino acid substitution selected from the group consisting of T368D, T368E, T368G, E375Y, E375W, K512Y, K512F, K512W, K512L, K512I, K512V, and K512H, or can include one of these substitutions at an indicated position (e.g., K512F where K512Y is listed). Optionally, the polymerase can comprise a mutation that inhibits exonuclease activity of the polymerase, such as an N62D, D12A, D66A, or T15I mutation.

The compositions comprising a modified recombinant polymerase that exhibits a reduced branching fraction phenotype, e.g., a branching fraction phenotype described above, can include a phosphate-labeled nucleotide analog, a DNA template, and a modified recombinant DNA polymerase, e.g., any of the polymerases described above, that can incorporate the nucleotide analog into a copy nucleic acid in response to the DNA template. These compositions can be present in a DNA sequencing system, e.g., a zero-mode waveguide. Optionally, the polymerase of the compositions can be immobilized on a surface.

In a related aspect, the invention provides methods of sequencing a DNA template. The methods include providing a reaction mixture that includes the DNA template, a replication initiating moiety that complexes with or is integral to the template, one or more nucleotides and/or nucleotide analogs, and a modified recombinant DNA polymerase, e.g., any of those described above. The polymerase of the reaction mixture is generally capable of replicating at least a portion of the template using the moiety in a template-dependent polymerization reaction.

The methods of sequencing the DNA template include subjecting the reaction mixture to a polymerization reaction in which the modified recombinant polymerase replicates at least a portion of the template in a template-dependent manner by incorporating one or more nucleotides and/or nucleotide analogs into the resulting DNA. The methods also include identifying a time sequence of incorporation of the one or more nucleotides and/or nucleotide analogs into the resulting DNA. The nucleotide analogs used in the methods can comprise a first analog and a second analog (and optionally third, fourth, etc.), each of which comprise different fluorescent labels. The different fluorescent labels can optionally be distinguished from one another during the step in which a time sequence of incorporation is identified. Subjecting the reaction mixture to a polymerization reaction and identifying a time sequence of incorporation can optionally be performed in a zero mode waveguide.

In another aspect, the invention also provides methods of making a DNA that include providing a reaction mixture that comprises a template, a replication initiating moiety that complexes with or is integral to the template, one or more nucleotides and/or nucleotide analogs, and a modified recombinant DNA polymerase, e.g., such as those described above, which can replicate at least a portion of the template using the moiety in a template-dependent polymerase reaction. The methods of making a DNA include reacting the mixture such that the polymerase replicates at least a portion of the template in a template-dependent manner, whereby the one or more nucleotides and/or nucleotide analogs are incorporated into the resulting DNA. Optionally, the reaction mixture can be reacted in a zero mode waveguide. Optionally, the method includes detecting the incorporation of at least one of the nucleotides and/or nucleotide analogs.

The invention also features compositions that include a modified recombinant Φ29-type DNA polymerase that comprises at least one amino acid substitution or combination of substitutions selected from: an amino acid substitution at position 153; an amino acid substitution at position 191; an amino acid substitution at position 388; an amino acid substitution at position 422; an amino acid substitution at position 128; an amino acid substitution at position 253; an amino acid substitution at position 504; an amino acid substitution at position 143; an amino acid substitution at position 183; an amino acid substitution at position 236; an amino acid substitution at position 363; P153L; G191A; T368F; T368P; T368S; T368V; T368N; T368A; T373N; T373V; T373C; I378V; I378F; K379S; K379A; S388A; S388T; K422R; F128M; F128V; I504V; K143D; K512R; Q183S; R236N; L253A; F363Y; L253A, F363Y, and L480M; T368F, K379S, E375Y, and K512Y; T368F and K379S; T368G and K379S; T368F and T373A; E375Y, K512Y and K379S; E375Y, K512Y and T368F; T368F and V514K; T368F and K379T; S388A and P153L; E375Y, K512Y and T368G; T368G and T373A; E375W and T368G; I378K and K379S; T368F and I378K; T368G and I378K; T368G and V514K; E375W and K379T; T373A and K379S; E375W and T373A; E375Y, K512Y and T373A; E375W and I378K; E375Y, K512Y and I378K; T373A and V514K; T373A and I378K; E375Y, K512Y and K379T; I378K and V514K; E375W and V514K; T368G and K379T; and E375Y, K512Y and V514K, where the numbering for the amino acid positions of the mutated residues is relative to that of the wild-type Φ29 polymerase. The modified recombinant polymerase of the compositions described above can optionally include one or more of amino acid substitution T368D, T368E, T368G, E375Y, E375W, K512Y, K512F, K512W, K512L, K512I, K512V, or K512H, or can include one of these substitutions at an indicated position (e.g., K512F where K512Y is listed). Optionally, the polymerase of the compositions can be exonuclease deficient. Essentially all of the features noted above apply to these embodiments as well, as relevant, e.g., with respect to inclusion of analogs in the composition, immobilization of the polymerase on a surface, use of the polymerase in sequencing or making DNA, and the like.

In a related aspect, the invention provides methods of making a modified recombinant DNA polymerase that include structurally modeling a parental DNA polymerase, e.g., a Φ29-type DNA polymerase, identifying one or more complex stability or nucleotide interaction feature affecting complex stability or nucleotide access or binding in the active site or a complementarity feature for a nucleotide analog at the active site, and mutating the parental DNA polymerase to include or remove these features. For example, the polymerase can be mutated to improve steric access of the nucleotide analog to the active site or to improve charge-charge or hydrophobic interactions between the nucleotide analog and the polymerase. The methods also include determining whether the resulting modified recombinant polymerase displays a decreased branching fraction for a nucleotide or nucleotide analog as compared to the parental polymerase.

Determining whether the resulting modified recombinant polymerase displays a decreased branching fraction for a nucleotide or nucleotide analog as compared to the parental polymerase can optionally include determining whether the modified recombinant polymerase displays a decreased branching fraction for a phosphate-labeled nucleotide analog, e.g., an analog including 3-7 phosphate groups such as those described herein. The methods optionally include making a library of modified recombinant polymerases, a plurality of which comprise one or more mutations at the one or more positions. Optionally, the methods include screening the library to identify at least one member exhibiting a decreased branching fraction.

Another aspect of the invention provides compositions that include a modified recombinant DNA polymerase that comprises at least one mutation relative to a parental polymerase that increases, or is predicted to increase, the stability of a closed complex comprising the recombinant DNA polymerase and a DNA (relative to a closed complex including the parental polymerase and DNA). A mutation that stabilizes the closed complex can optionally stabilize an interaction between the thumb, TPR2, and/or exonuclease domains.

The stability of the closed complex can optionally be measured by determining a dissociation rate or dissociation rate constant ($k_{off}$) for dissociation of the polymerase from the DNA. The dissociation rate constant ($k_{off}$) for dissociation of the polymerase from the DNA is optionally measured in the presence of an excess of a competitor of the DNA, e.g., heparin or a population of DNA molecules. Optionally, dissociation can be indirectly measured by measuring an activity of the DNA polymerase over time. Optionally, the stability of the closed complex can be determined by measuring $K_d$ for the complex. The increased stability of the complex can optionally include an improvement of at least about 30%.

The recombinant DNA polymerase that can form a more stable closed complex with a DNA can optionally exhibit increased processivity as compared to the parental polymerase. Processivity can be defined as $(k_{ext})/(k_{ext}+k_{off})$, wherein $k_{ext}$ is the extension rate constant and $k_{off}$ is the rate constant for polymerase dissociation from the DNA. Optionally, the mutation decreases $k_{off}$. Processivity of the modified recombinant polymerase can optionally be at least twice that of the parental polymerase. The DNA of the compositions can optionally comprise a template strand and a primer.

The recombinant DNA polymerase that includes at least one mutation relative to a parental polymerase that increases, or is predicted to increase, the stability of a closed conformation of a complex comprising the recombinant DNA polymerase and a DNA can optionally be homologous to a Φ29 DNA polymerase, a Taq polymerase, an exonuclease deficient Taq polymerase, a DNA Pol I polymerase, a T7 polymerase, a T5 Polymerase, an RB69 polymerase, a T5 polymerase or a polymerase corresponding to a Klenow fragment of a DNA Pol I polymerase. Optionally the polymerase can be homologous to one or more polymerases, including a wild-type Φ29 DNA polymerase, an exonuclease deficient Φ29 DNA polymerase, a B103 DNA polymerase, a GA-1 DNA polymerase, a PZA DNA polymerase, a Φ15 DNA polymerase, a BS32 DNA polymerase, a M2Y DNA polymerase, an Nf DNA polymerase, a G1 DNA polymerase, a Cp-1 DNA polymerase, a PRD1 DNA polymerase, a PZE DNA polymerase, an SF5 DNA polymerase, a Cp-5 DNA polymerase, a Cp-7 DNA polymerase, a PR4 DNA polymerase, a PR5 DNA polymerase, a PR722 DNA polymerase, or an L17 DNA polymerase. Optionally, the modified recombinant polymerase can be a modified recombinant Φ29-type DNA polymerase, which modified recombinant polymerase comprises at least one mutation relative to the parental polymerase at one or more positions selected from the group consisting of position 68-position 76, position 92, position 405-position 413, and position 560-position 564, where the numbering for the amino acid positions of the mutated residues is relative to that of the wild-type Φ2 polymerase. For example, the polymerase optionally comprises at least one amino acid substitution or combination of substitutions from T92F, T92I, G410D, T92I and G410D, N72A, N72I, N72F, and N72S. Essentially all of the features noted above apply to these embodiments as well, as relevant, e.g., with respect to inclusion of analogs in the composition, immobilization of the polymerase on a surface, use of the polymerase in sequencing or making DNA, and the like.

A related aspect of the invention provides compositions comprising a modified recombinant Φ29-type DNA polymerase that comprises one or more amino acid substitutions relative to a parental polymerase at one or more positions selected from the group consisting of position 68-position 76, position 92, position 405-position 413, and position 560-position 564, where the numbering for the amino acid positions of the mutated residues is relative to that of the wild-type Φ29 polymerase. The modified recombinant polymerase of the compositions exhibits increased stability of a closed complex comprising the recombinant DNA polymerase and a DNA as compared to the parental polymerase.

The recombinant and parental polymerase of the compositions can optionally be homologous to a Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. Optionally, the modified recombinant polymerase is a modified recombinant Φ29 polymerase that comprises at least one amino acid substitution or combination of substitutions that include T92F, T92I, G410D, T92I and G410D, N72A, N72I, N72F,and N72S.

The compositions that comprise a modified recombinant polymerase that can form a more stable closed complex with a DNA can optionally include a nucleotide analog. The analog can optionally comprise a fluorophore, a phosphate-labeled nucleotide analog, and/or a labeled nucleotide analog having from 3-7 phosphate groups. Optionally, the compositions can include a nucleotide analog and a DNA template, and the modified recombinant polymerase of the composition can incorporate the nucleotide analog into a copy nucleic acid in response to the DNA template. The composition can optionally be present in a DNA sequencing system, e.g., a zero-mode waveguide. The one or more amino acid substitutions of the modified recombinant polymerase in the compositions can optionally increase, or be predicted to increase, the stability of a closed conformation of the modified recombinant polymerase relative to the parental polymerase. Optionally, the modified recombinant polymerase can be immobilized on a surface. Essentially all of the features noted above apply to these embodiments as well, as relevant.

In a related aspect, the invention provides methods of sequencing a DNA template that include providing a reaction mixture. The reaction mixture includes the DNA template, a replication initiating moiety that complexes with or is integral to the template, one or more nucleotides and/or nucleotide analogs, and a modified recombinant Φ29-type DNA polymerase that comprises one or more amino acid substitutions relative to a parental polymerase at one or more positions selected from the group consisting of position 68-position 76, position 92, position 405-position 413, and position 560-position 564, where the numbering for the amino acid positions of the mutated residues is relative to that of the wild-type Φ29 polymerase. The polymerase of the reaction mixture can be capable of replicating at least a portion of the template using the moiety in a template-dependent polymerization reaction.

The methods of sequencing a DNA template include subjecting the reaction mixture to a polymerization reaction in which the modified recombinant polymerase replicates at least a portion of the template in a template-dependent manner, whereby the one or more nucleotides and/or nucleotide analogs are incorporated into the resulting DNA. The methods also include identifying a time sequence of incorporation of the one or more nucleotides and/or nucleotide analogs into the resulting DNA.

The nucleotide analogs used in the methods can comprise a first analog and a second analog (and optionally third, fourth, etc.), each of which comprise different fluorescent labels. The different fluorescent labels can optionally be distinguished from one another during the step in which a time sequence of incorporation is identified. Optionally, subjecting the reaction mixture to a polymerization reaction and identifying a time sequence of incorporation can be performed in a zero mode waveguide.

In another related aspect, the invention provides methods of making a DNA that include providing a reaction mixture. The reaction mixture includes a template, a replication initiating moiety that complexes with or is integral to the template, one or more nucleotides and/or nucleotide analogs, and a modified recombinant Φ29-type DNA polymerase that comprises one or more amino acid substitutions relative to a parental polymerase at one or more positions selected from the group consisting of position 68-position 76, position 92, position 405-position 413, and position 560-position 564, where the numbering for the amino acid positions of the mutated residues is relative to that of the wild-type Φ29 polymerase. The polymerase in the reaction mixture can be capable of replicating at least a portion of the template using the moiety in a template-dependent polymerase reaction.

The methods include reacting the mixture such that the polymerase replicates at least a portion of the template in a template-dependent manner, whereby the one or more nucleotides and/or nucleotide analogs are incorporated into the resulting DNA. The reaction mixture used in the methods can optionally be reacted in a zero mode waveguide. The method can optionally include detecting incorporation of at least one of the nucleotides and/or nucleotide analogs.

In another aspect, the invention also provides methods of making a modified recombinant DNA polymerase. These methods include structurally modeling a parental DNA polymerase, identifying one or more amino acid residue positions in the parental DNA polymerase as targets for mutation, and mutating the parental polymerase at the one or more positions to introduce at least one intramolecular interaction predicted to stabilize the closed complex of the polymerase or to remove at least one intramolecular interaction predicted to destabilize the closed complex. The methods include determining whether the resulting modified recombinant polymerase displays an increased processivity, decreased $k_{off}$, or decreased $K_d$, as compared to the parental polymerase.

The methods can optionally include making a library of modified recombinant polymerases that comprise one or more mutations at the one or more positions. Optionally, the methods can include screening the library to identify at least one member exhibiting increased processivity, decreased $k_{off}$, or decreased $K_d$. The parental DNA polymerase can optionally be a Φ29-type DNA polymerase, and the amino acid positions identified in the parental DNA polymerase as targets for mutation can comprise at least one residue selected from position 68-position 76, position 92, position 405-position 413, and position 560-position 564, where the numbering for the amino acid positions of the mutated residues is relative to that of the wild-type Φ29 polymerase.

In another aspect, the invention provides a composition that includes a modified recombinant DNA polymerase that comprises one or more mutations relative to a parental polymerase and that exhibits a first rate constant for a first step in its catalytic cycle (generally, the forward rate constant for the first step) that is less than a first rate constant for the first step exhibited by the parental polymerase (e.g., a wild-type or previously available mutant polymerase, e.g., an exonuclease-deficient polymerase). For example, the first rate constant exhibited by the modified recombinant polymerase can be less than 0.25 times the first rate constant exhibited by the parental polymerase, e.g., less than about 0.1 times.

As discussed in greater detail herein, decreasing the rate of certain steps within the catalytic cycle can improve accuracy in single molecule sequencing techniques, for example, by reducing the number of times that incorporation of a labeled nucleotide with release of the label is too fast to be detected. Slowing the rate of a step which is not normally rate limiting in the catalytic cycle can be particularly useful in this regard. Manipulating the rate of the first step so that it is comparable to that of another step, particularly one that is already relatively slow, is also particularly useful in this regard. Thus, the modified recombinant polymerase optionally exhibits a second rate constant for a second step in its catalytic cycle (generally, the forward rate constant for the second step), where the second rate constant is between 0.1 and 10 times the first rate constant, preferably between 0.2 and 5 times the first rate constant, and more preferably approximately equal to the first rate constant. It will be understood that in this context, the terms first step and second step are merely used for convenience in referring to two different steps and do not imply any particular order of occurrence (that is, the first step can precede or follow the second and need not be the initial event in the catalytic pathway).

The second step is optionally rate limiting in the catalytic cycle of the parental polymerase (and optionally also of the modified polymerase). More generally, however, the first and/or second step can be limiting in a portion of the cycle, not necessarily the entire cycle. For example, the first and second steps can be limiting in the bright portion of the cycle where a label from a labeled analog is retained in a complex with the polymerase, or in the dark portion of the cycle where the label is not associated with the polymerase. As one example, the second step can involve incorporation of a bound nucleotide or nucleotide analog, e.g., an analog having from 3-7 phosphate groups, e.g., with a terminal label.

Any of a number of steps can be slowed using the techniques of the instant invention. In one aspect, product release, particularly polyphosphate product release, is slowed (i.e., the first step involves release of a polyphosphate product). Optionally, the first rate constant exhibited by the modified recombinant polymerase is less than about 100/second, e.g., less than about 75/second or even less than about 50/second. In one exemplary embodiment, the second step involves incorporation of a bound nucleotide or nucleotide analog, the first step involves release of a polyphosphate product, and the second rate constant exhibited by the modified recombinant polymerase is between 0.1 and 10 times (e.g., between 0.2 and 5 times or between 0.2 and 1 times) the first rate constant exhibited by the modified recombinant polymerase.

It will be evident that the rate of the second step can also be manipulated, e.g., to balance the rates of the first and second steps. Thus, the second rate constant exhibited by the modified recombinant polymerase is optionally smaller (faster) than the second rate constant exhibited by the parental polymerase for the second step.

The modified recombinant polymerase can be a modified recombinant I29-type DNA polymerase, for example, a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. The polymerase optionally comprises at least one amino acid substitution or combination of substitutions selected from the group consisting of: an amino acid substitution at position 484; an amino acid substitution at position 198; an amino acid substitution at position 381; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F; wherein numbering of positions is relative to wild-type Φ29 polymerase. Additional exemplary mutations are described herein. The polymerase can include a mutation that inhibits exonuclease activity of the polymerase, e.g., an N62D, D12A, D66A, or T15I substitution.

The composition optionally also includes one or more nucleotide analog, for example, a phosphate-labeled nucleotide analog, e.g., one comprising a fluorophore and/or having from 3-7 phosphate groups. Similarly, the composition can include a phosphate-labeled nucleotide analog and a DNA template, wherein the modified recombinant polymerase incorporates the nucleotide analog into a copy nucleic acid in response to the DNA template. The composition can be present in a DNA sequencing system, e.g., a zero mode waveguide. Optionally, the polymerase is immobilized on a surface.

In a related aspect, the invention provides methods of sequencing a DNA template. In the methods, a reaction mixture that includes the DNA template, a replication initiating moiety that complexes with or is integral to the template, one or more nucleotides and/or nucleotide analogs, and a modified recombinant DNA polymerase, e.g., any of those described above, is provided. The polymerase is generally capable of replicating at least a portion of the template using the moiety in a template-dependent polymerization reaction.

The reaction mixture is subjected to a polymerization reaction in which the modified recombinant polymerase replicates at least a portion of the template in a template-dependent manner by incorporating one or more nucleotides and/or nucleotide analogs into the resulting DNA. A time sequence of incorporation of the one or more nucleotides and/or nucleotide analogs into the resulting DNA is identified. The nucleotide analogs used in the methods can comprise a first analog and a second analog (and optionally third, fourth, etc.), each of which comprise different fluorescent labels. The different fluorescent labels are optionally distinguished from one another during the step in which a time sequence of incorporation is identified. The polymerization reaction and the identification step are optionally performed in a zero mode waveguide.

In another aspect, the invention also provides methods of making a DNA that include providing a reaction mixture that comprises a template, a replication initiating moiety that complexes with or is integral to the template, one or more nucleotides and/or nucleotide analogs, and a modified recombinant DNA polymerase, e.g., such as those described above, which can replicate at least a portion of the template using the moiety in a template-dependent polymerase reaction. The methods of making a DNA include reacting the mixture such that the polymerase replicates at least a portion of the template in a template-dependent manner, whereby the one or more nucleotides and/or nucleotide analogs are incorporated into the resulting DNA. The reaction mixture is optionally reacted in a zero mode waveguide. Optionally, the method includes detecting the incorporation of at least one of the nucleotides and/or nucleotide analogs.

One general class of embodiments provides a composition comprising a modified recombinant DNA polymerase, e.g., a modified recombinant Φ29-type DNA polymerase, that exhibits a rate constant for release of a polyphosphate product that is less than about 50/second. Essentially all of the features noted above apply to these embodiments as well, as relevant, e.g., with respect to inclusion of analogs in the composition, immobilization of the polymerase on a surface, use of the polymerase in sequencing or making DNA, and the like. The modified polymerase can include mutations detailed herein, for example, one or more amino acid substitution or combination of substitutions selected from: an amino acid substitution at position 484; an amino acid substitution at position 198; an amino acid substitution at position 381; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F.

Another general class of embodiments provides a composition comprising a modified recombinant polymerase, e.g., a modified recombinant Φ29-type DNA polymerase, that comprises one or more mutations relative to a parental polymerase at one or more positions selected from the group consisting of a) positions that form a binding site for a metal ion that interacts with an epsilon and/or digamma phosphate of a bound nucleotide analog having five or more phosphate groups; b) positions 372-397 and 507-514; c) positions that form a binding site for a terminal fluorophore on a phosphate-labeled nucleotide analog; d) positions at an intramolecular interface in a closed conformation of a ternary complex comprising the polymerase, a DNA, and a nucleotide or nucleotide analog; e) positions that form a binding site for a polyphosphate group of a bound nucleotide or nucleotide analog; 0 positions that interact with the base of a bound nucleotide or nucleotide analog; and g) positions that interact with a bound DNA; wherein numbering of positions is relative to wild-type Φ29 polymerase. Typically, the one or more mutations comprise at least one mutation other than a 514Y, 514W, 514F, 514I, 514K, 259S, 370V, 370K, 372D, 372E, 372R, 372K, 372N, 372L, 387A, 387D, 478D, 478E, 478R, 480K, 480M, 480R, 371Q, 379E, 379T, 486D, 486A, 188A, 188S, 254F, 254V, 254A, 390F, or 390A substitution.

The recombinant and parental polymerase are optionally homologous to a Φν, B103, GA-1, PZA, Φ15, BS32, M2Y, Nf, G1, Cp-1, PRD1, PZE, SF5, Cp-5, Cp-7, PR4, PR5, PR722, or L17 polymerase.

The one or more mutations can include at least one amino acid substitution, for example, at least one amino acid substitution at at least one residue selected from the group consisting of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, and 390. Exemplary substitutions and combinations thereof include, but are not limited to, A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F. Exemplary mutations also include insertions and deletions. Thus, for example, the one or more mutations can comprise an insertion of at least one amino acid within residues 372-397 and/or 507-514. Other exemplary mutations are described herein.

Essentially all of the features noted above apply to these embodiments as well, as relevant, e.g., with respect to inclusion of analogs in the composition, immobilization of the polymerase on a surface, use of the polymerase in sequencing or making DNA, and the like.

A related aspect of the invention provides methods of making a modified recombinant DNA polymerase that include structurally modeling a parental DNA polymerase, identifying one or more amino acid residue positions in the parental DNA polymerase as targets for mutation, mutating the parental polymerase at the one or more positions, and determining whether the resulting modified recombinant polymerase exhibits a first rate constant for a first step in its catalytic cycle that is less than a first rate constant for the first step exhibited by the parental polymerase. The methods optionally also include determining whether the resulting modified polymerase exhibits a second rate constant for a second step where the second rate constant is between 0.1 and 10 times the first rate constant.

A number of strategies for producing such polymerases are described herein. For example, the parental DNA polymerase and a bound nucleotide analog having five or more phosphate group can be modeled, and one or more amino acid residues of the parental DNA polymerase that form a binding site for a metal ion that interacts with an epsilon and/or digamma phosphate of the analog can be identified as the targets for mutation. In another example, the parental polymerase is mutated at the one or more positions to introduce at least one intramolecular interaction predicted to stabilize a closed conformation of a ternary complex comprising the polymerase, a DNA, and a nucleotide or nucleotide analog or to remove at least one intramolecular interaction predicted to destabilize the closed conformation.

In another example, the parental polymerase is mutated at the one or more positions to increase intermolecular interaction between the polymerase and the base of an incoming nucleotide or nucleotide analog. In yet another example, the parental polymerase is mutated at the one or more positions to increase intermolecular interaction between the polymerase and a terminal fluorophore on a nucleotide analog. In an additional example, the parental DNA polymerase is modeled with a bound nucleotide analog having four or more phosphate groups, and the parental polymerase is mutated at the one or more positions to alter isomerization of the phosphate groups. In a related example, the parental DNA polymerase is modeled with a bound polyphosphate, and the parental polymerase is mutated at the one or more positions to alter isomerization of the polyphosphate. In another example, the parental DNA polymerase and a DNA are modeled, and one or more amino acid residues of the parental DNA polymerase that interact with the DNA and/or that are within 4 Å of the DNA are identified as targets for mutation.

The methods can be applied to any of the large number of polymerases available in the art, for example, a Φ29-type DNA polymerase. In one exemplary class of embodiments, the parental polymerase is a Φ29-type DNA polymerase, and the one or more positions identified in the parental DNA polymerase as targets for mutation comprise at least one residue selected from the group consisting of position 484, 249, 179, 198, 211, 255, 259, 360, 363, 365, 370, 372, 378, 381, 383, 387, 389, 393, 433, 478, 480, 514, 372-397, 507-514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, and 390, wherein numbering of positions is relative to wild-type Φ29 DNA polymerase.

The methods optionally include making a library of modified recombinant polymerases, a plurality of which comprise one or more mutations at the one or more positions. Optionally, the methods include screening the library to identify at least one member exhibiting the decreased first rate constant. Similarly, the library is optionally screened to identify at least one member exhibiting comparable first and second rate constants, as described herein.

Essentially all of the features noted for the compositions above apply to these embodiments as well, as relevant, e.g., with respect to type of first and/or second steps, balance of the first and second rate constants, type of parental polymerase, and the like.

The present invention also features kits that include the polymerases of the invention, optionally with additional useful reagents such as one or more nucleotide analogs, e.g., for sequencing, nucleic acid amplification, or the like. Such kits can include the polymerase of the invention packaged in a fashion to enable use of the polymerase, a set of different nucleotide analogs of the invention, e.g., those that are analogous to A, T, G, and C, e.g., where one or more of the analogs comprise a detectable moiety to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions such as $Ca^{++}$, $Mg^{++}$, $Mn^{++}$ and/or $Fe^{++}$, and standard solutions, e.g., dye standards for detector calibration. Such kits also typically include instructions for use of the polymerases and other reagents in accordance with the desired application methods, e.g., nucleic acid sequencing, amplification and the like. DNA sequencing systems that include any of the modified polymerases described herein are also a feature of the invention. Such systems can optionally include detectors, excitation light sources, array readers, and the like.

Those of skill in the art will appreciate that that the methods provided by the invention for modifying a DNA polymerase, e.g., to decrease branching fraction formation during polymerization, increase closed polymerase/DNA complex stability, and/or slow one or more steps in the catalytic cycle, can be used alone or in combination. Accordingly, all of the various mutations described herein can appear singly or in combination in a modified recombinant polymerase.

DEFINITIONS

Figure 1B:
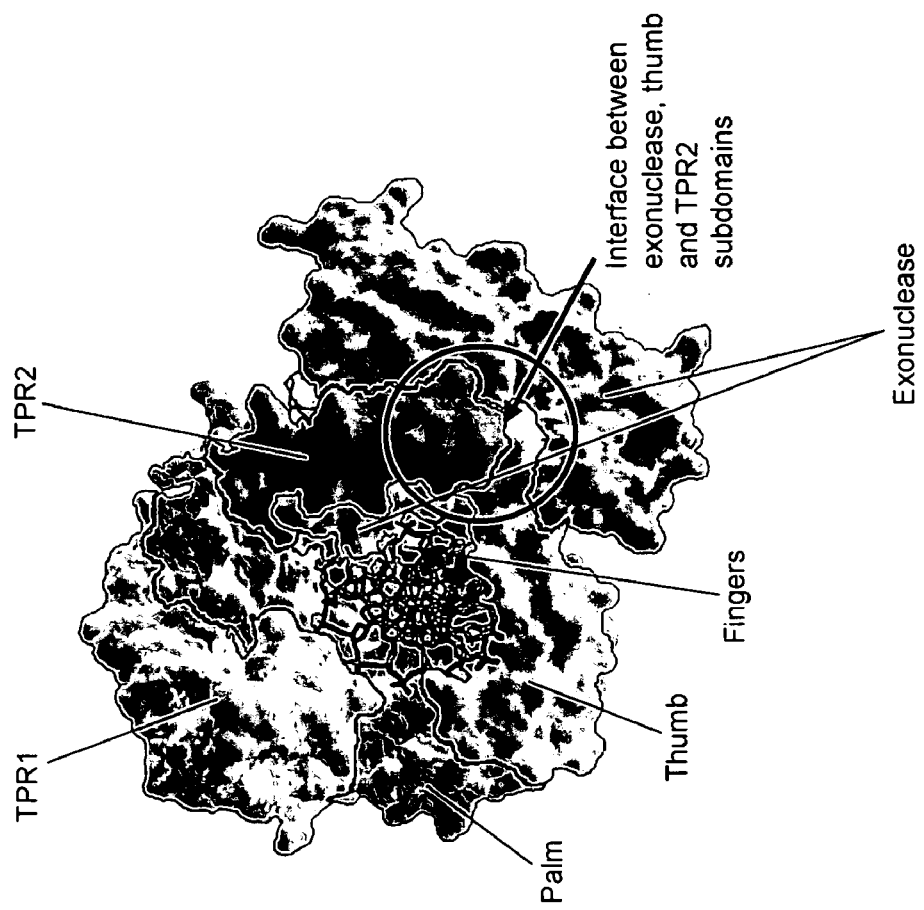
FIG. 1 Panels A and B depict a closed Φ29 polymerase/DNA complex.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like.

The term "about" as used herein indicates the value of a given quantity varies by ±10% of the value, or optionally ±5% of the value, or in some embodiments, by ±1% of the value so described.

The term "nucleic acid" or "polynucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention encompasses complementary sequences, in addition to the sequence explicitly indicated.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

An "amino acid sequence" is a polymer of amino acid residues (a protein, polypeptide, etc.) or a character string representing an amino acid polymer, depending on context.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Numbering of a given amino acid or nucleotide polymer "corresponds to numbering of" or is "relative to" a selected amino acid polymer or nucleic acid when the position of any given polymer component (amino acid residue, incorporated nucleotide, etc.) is designated by reference to the same residue position in the selected amino acid or nucleotide, rather than by the actual position of the component in the given polymer. Correspondence of positions is typically determined by aligning the relevant amino acid or polynucleotide sequences.

The term "recombinant" indicates that the material (e.g., a nucleic acid or a protein) has been artificially or synthetically (non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is, e.g., a polypeptide or protein which is produced by expression of a recombinant nucleic acid.

A "Φ29-type DNA polymerase" (or "phi29-type DNA polymerase") is a DNA polymerase from the Φ29 phage or from one of the related phages that, like Φ29, contain a terminal protein used in the initiation of DNA replication. Φ29-type DNA polymerases are homologous to the Φ2 DNA polymerase; examples include the B103, GA-1, PZA, Φ15, BS32, M2Y, Nf, G1, Cp-1, PRD1, PZE, SF5, Cp-5, Cp-7, PR4, PR5, PR722, and L17 DNA polymerases, as well as chimeras thereof. A modified recombinant Φ29-type DNA polymerase includes one or more mutations relative to naturally-occurring wild-type Φ29-type DNA polymerases, for example, one or more mutations that increase closed complex stability, decrease branching fraction, and/or slow a catalytic step relative to a corresponding wild-type polymerase, and may include additional alterations or modifications over wild-type Φ29-type DNA polymerases, such as deletions, insertions, and/or fusions of additional peptide or protein sequences (e.g., for immobilizing the polymerase on a surface or otherwise tagging the polymerase enzyme).

A variety of additional terms are defined or otherwise characterized herein.

DETAILED DESCRIPTION

One aspect of the invention is generally directed to modified or engineered polymerases that are characterized by lowered frequency of branching events during polymerization reactions, increased stability of closed polymerase-DNA complexes, and/or decreased rates for steps in the polymerization cycle. Individually or in combination, these modifications can increase polymerase processivity and/or polymerase activity readout accuracy (e.g., increase sequence accuracy in single molecule sequencing reactions). Polymerases of the invention optionally include additional mutations that provide other desirable features, e.g., that eliminate exonuclease or proof reading activity of the relevant polymerase, increase residence time of nucleotide analogs at an active site of the polymerase, modify one or more kinetic feature of the polymerase, increase surface stability for polymerases bound to a surface, or the like.

As noted, polymerases exhibiting a decreased branching fraction are a feature of the invention. "Branching" is a phenomenon that occurs during polymerization. During a polymerase kinetic cycle, sampling of each of four possible nucleotides (or analogs) occurs until a correct Watson-Crick pairing is generated (see, e.g., Hanzel et al. WO 2007/076057 POLYMERASES FOR NUCLEOTIDE ANALOGUE INCORPORATION for a description of the kinetic cycle of a polymerase; see also the section entitled "Polymerase Mediated Synthesis" hereinbelow). However, chemical linkages between a sampled nucleotide and a 3' hydroxyl group of a preceding base can fail to occur for a correctly paired nucleotide, due to release of the correctly paired base from the active site. Such failures to physically incorporate the correct nucleotide can result in sequence read errors in single molecule sequencing by incorporating methods, e.g., because the correct nucleotide can display a longer residence time than an incorrect nucleotide at the site, and can be read by the readout system as an incorporation event. The polymerase kinetic cycle is repeated for the same site, eventually resulting in actual physical incorporation of the correct nucleotide at the site. However, where both the failed incorporation and the actual incorporation of the nucleotides are read by the system as incorporation events, sequences deciphered during single molecule sequencing (SMS) for the incorporation site have an incorrect "insertion" relative to the correct sequence. This phenomenon is termed "branching" because it leads to a "branch" in the sequence (a site where two identical molecules will be read as having different sequences) and can ultimately generate high error rates during single molecule sequencing. In one aspect of the present invention, modification of the polymerase by site-directed mutagenesis is used to lower the frequency of these "branching" events by creating a more tightly structured binding pocket for the (typically non-natural) nucleotides that are incorporated during SMS. Accordingly, as described in this application, mutants were designed to address this issue by modifying various sites in the Φ29 polymerase, predominantly in and around the binding pocket, to create tighter polymerase-analog interactions during an extension reaction. As noted, the "branching fraction" is the proportion of cognate nucleotide (or nucleotide analog, e.g., A488dA4P) dissociation events from the polymerase active site to the total number of events, e.g., the sum of the incorporation events and dissociation events. Desirably, the branching fraction for a polymerase for a given nucleotide or analog of interest (e.g., a labeled nucleotide analog) should be less than 25%, more preferably less than 20%, more preferably less than 15%, yet more preferably less than 10%, or even less than 5%, 1%, or 0.1% of the total interactions, e.g., dissociation events and association events, of the nucleotide analog with the polymerase binding pocket. For example, the branching fraction can be e.g., about 22.5% or less, about 17.5% or less, about 12.5% or less, or about 7.5% or less. In comparison, a wild type Φ29 polymerase exhibits a branching fraction of about ≧40% for, e.g., a gamma-linked A488dA4 nucleotide analog, wherein ≧40% of the total events with the A488dA4 nucleotide analog in the polymerase binding pocket are dissociation events.

Alternately or additionally, the polymerases of the invention can display a branching fraction that is 0.5× as high as a wild type parental polymerase (e.g., a wild type Φ29) or less. Preferably, the branching fraction, or optionally rate, is about 0.25× as high as the parental polymerase or less, e.g., about 0.15× as high or less, or even 0.05× as high or less.

Polymerases with increased stability of a closed polymerase/DNA complex are another feature of the invention. "Increased stability of a closed polymerase-DNA complex" refers to an increased stability of a polymerase when it is bound to a DNA template, e.g., in the presence of a primer or other moiety that can serve as an extension site for the polymerase. This increased stability can be measured as a rate of dissociation of the polymerase from the DNA, e.g., in the presence of a DNA trap (an excess of a competitor molecule that binds to the polymerase once it releases from the DNA, such as an excess of heparin, non-specific DNA, or the like); optionally, the dissociation rate constant ($k_{off}$) is determined. As another example, $K_d$ can be measured to assess stability ($K_d$ is an equilibrium constant depending on the binding rate and dissociation rate constants). Improvements of about 30% in complex stability, and preferably about 50%, about 75%, about 100% or more for a polymerase of the invention as compared to a parental (e.g., wild-type) polymerase are desirable. Increases in stability of the complex lead, e.g., to an increase in processivity of the DNA polymerase, which increases the speed and accuracy of sequence reads. Processivity can be defined as the number of bases that can be read without dissociation of the polymerase; here again improvements of about 30% in complex stability, and preferably about 50%, about 75%, about 100% or more are desirable. Improvements in stability can be brought about by selecting mutations that modify amino acid interactions between major domains of the polymerase that wrap around a DNA in the closed conformation (e.g., when the polymerase is wrapped around the DNA template). These domains include the exonuclease domain, the thumb domain, and the TPR2 domain. These include, e.g., residues 68 to 76 and 92 (exonuclease), 405 to 413 (TPR2), and 560-564 (thumb), with the numbering being relative to wild-type Φ29.

Polymerases that exhibit altered kinetic behavior, particularly a decreased rate for at least one step in the catalytic cycle, form yet another feature of the invention. Such polymerases optionally exhibit comparable rates (e.g., comparable rate constants) for two steps within the catalytic cycle. As is described in greater detail below, by decreasing the rate of certain steps the interaction between the polymerase and nucleotides or nucleotide analogs to be incorporated can be prolonged, increasing detection of incorporation events in single molecule sequencing techniques and improving sequencing accuracy.

The properties of decreased sequence branching, increased polymerase complex stability (and processivity), and selectively decreased rates are particularly useful in the context of incorporation of labeled nucleotides by the polymerase, e.g., as detected during "sequencing by incorporation" methods (including, e.g., SMS methods). For example, the invention provides, e.g., compositions that include one or more engineered or modified polymerase enzymes optionally with one or more template DNAs and/or labeled or otherwise modified nucleotides or nucleotide analogs, where the composition exhibits decreased branching fraction, increased stability of the closed polymerase-DNA complex and/or improved processivity, and/or decreased rate constant for one or more steps during template dependent polymerase mediated nucleic acid synthesis. Methods, including SMS methods, using these compositions are also provided, as are general methods of making polymerases having the properties noted herein.

The polymerase mutations and mutational strategies noted herein can be combined with each other and with essentially any other available mutations and mutational strategies to confer additional improvements in, e.g., nucleotide analog specificity, enzyme processivity, improved retention time of labeled nucleotides in polymerase-DNA-nucleotide complexes, and the like. For example, the mutations and mutational strategies herein can be combined with those taught in, e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al. This combination of mutations/mutational strategies can be used to impart several simultaneous improvements to a polymerase (e.g., decreased branch fraction formation, improved specificity, improved processivity, altered rates, improved retention time, improved stability of the closed complex, etc.). In addition, polymerases can be further modified for application-specific reasons, such as to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

Specific mutations noted herein can be used alone or in combination with each other and/or with available mutations as described in the references noted above, or can be used in polymerases that lack such previously described mutations. As just one example, essentially any mutation or combination thereof noted herein can be introduced into an E375Y/K512Y/T368F Φ29 polymerase, optionally, an exonuclease-deficient E375Y/K512Y/T368F Φ29 polymerase.

Accordingly, among other aspects, the present invention provides new polymerases that incorporate nucleotide analogs, such as dye labeled phosphate labeled analogs, into a growing template copy during DNA amplification. These polymerases are modified such that they have decreased branching fraction formation when incorporating the relevant analogs, have improved DNA-polymerase stability or processivity, and/or have altered kinetic properties as compared to corresponding wild-type or other parental polymerases (e.g., polymerases from which modified recombinant polymerases of the invention were derived, e.g., by mutation). The polymerases of the invention can also include any of the additional features for improved specificity, improved processivity, improved retention time, improved surface stability, affinity tagging, and/or the like.

These new polymerases are particularly well suited to DNA amplification and/or sequencing applications, particularly sequencing protocols that include detection in real time of the incorporation of labeled analogs into DNA amplicons, since the decreased branch fraction, improved complex stability, and/or altered rates can facilitate discrimination of nucleotide incorporation events from non-incorporation events such as transient binding of a mis-matched nucleotide in the active site of the complex, improve processivity, and/or facilitate detection of incorporation events.

DNA Polymerases

DNA polymerases that can be modified to have decreased branching fraction, increased stability for the closed DNA polymerase-DNA complex, or altered rate constants are generally available. DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.) and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576, 204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287.

Nucleotide Analogs

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). A "nucleotide analog" (or "nucleotide analogue") herein is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can also be modified to achieve any of the improved properties desired. For example, various linkers or other substituents can be incorporated into analogs that have the effect of reducing branching fraction, improving processivity, or altering rates. Modifications to the analogs can include extending the phosphate chains, e.g., to include a tetra-, penta-, hexa- or heptaphosphate group, and/or adding chemical linkers to extend the distance between the nucleotide base and the dye molecule, e.g., a fluorescent dye molecule. Substitution of one or more non-bridging oxygen in the polyphosphate, for example with S or $BH_3$, can change the polymerase reaction kinetics, e.g., to achieve a system having two slow steps as described hereinbelow. Optionally, one or more, two or more, three or more, or four or more non-bridging oxygen atoms in the polyphosphate group of the analog has an S substituted for an O. While not being bound by theory, it is believed that the properties of the nucleotide, such as the metal chelation properties, electronegativity, or steric properties, can be altered by substitution of the non-bridging oxygen(s).

Many nucleotide analogs are available and can be incorporated by the polymerases of the invention. These include analog structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, the nucleotide analog includes three phosphate containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate. For example, a variety of nucleotide analogs that comprise, e.g., from 4-6 or more phosphates are described in detail in U.S. patent application Ser. No. 11/241,809, filed Sep. 29, 2005, and incorporated herein by reference in its entirety for all purposes. Other exemplary useful analogs, including tetraphosphate and pentaphosphate analogs, are described in U.S. Pat. No. 7,041, 812, incorporated herein by reference in its entirety for all purposes.

For example, the analog can include a labeled compound of the formula:

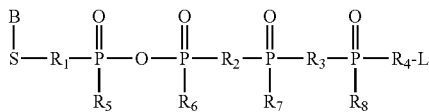

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

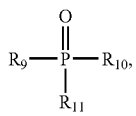

and

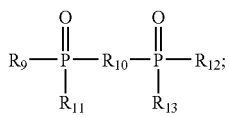

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., U.S. patent application Ser. No. 11/241,809, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2', 3'-D-didehydrodideoxyribosyl, 2' or 3' alkoxyribosyl, 2' or 3' aminoribosyl, 2' or 3+ mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$ etc.) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., U.S. Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Thus, in one illustrative example, the analog can be a phosphate analog (e.g., an analog that has more than the typical number of phosphates found in nucleoside triphosphates) that includes, e.g., an Alexa dye label. For example, an Alexa488 dye can be labeled on a delta phosphate of a tetraphosphate analog (denoted, e.g., A488dC4P or A488dA4P, shown in FIG. 3, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C or A568dT6P for a labeled hexaphospate analog of T), or an Alexa546 dye can be used (e.g., A546dG4P), or an Alexa594 dye can be used (e.g., A594dT4P). As additional examples, an Alexa555 dye (e.g., A555dC6P or A555dA6P), an Alexa 647 dye (e.g., A647dG6P), an Alexa 568 dye (e.g., A568dT6P), and/or an Alexa660 dye (e.g., A660dA6P or A660dC6P) can be used in, e.g., single molecule sequencing. Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

Applications for Enhanced Nucleic Acid Amplification and Sequencing

Polymerases of the invention, e.g., modified recombinant polymerases, are optionally used in combination with nucleotides and/or nucleotide analogs and nucleic acid templates (DNA or RNA) to copy the template nucleic acid. That is, a mixture of the polymerase, nucleotides/analogs, and optionally other appropriate reagents, the template and a replication initiating moiety (e.g., primer) is reacted such that the polymerase synthesizes nucleic acid (e.g., extends the primer) in a template-dependent manner. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as a initiating moiety. At least one nucleotide analog can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogs by the polymerases of the invention is particularly useful in a variety of different nucleic acid analyses, including real-time monitoring of DNA polymerization. The label can itself be incorporated, or more preferably, can be released during incorporation of the analog. For example, analog incorporation can be monitored in real-time by monitoring label release during incorporation of the analog by the polymerase. The portion of the analog that is incorporated can be the same as a natural nucleotide, or can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in U.S. Patent Application Publication No. 2003/0044781, incorporated herein by reference.

In one example reaction of interest, a polymerase reaction can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., U.S. Patent Application Publication No. 2003/0044781, and U.S. Pat. No. 6,917,726, each of which is incorporated herein by reference in its entirety for all purposes. See also Levene et al. (2003) "Zero-mode waveguides for single-molecule analysis at high concentrations" Science 299:682-686, Eid et al. (2009) "Real-time DNA sequencing from single polymerase molecules" Science 323:133-138, and U.S. Pat. Nos. 7,056,676, 7,056,661, 7,052,847, and 7,033,764, the full disclosures of which are incorporated herein by reference in their entirety for all purposes.

In general, a polymerase enzyme is complexed with the template strand in the presence of one or more nucleotides and/or one or more nucleotide analogs. For example, in certain embodiments, labeled analogs are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such nucleotide, and incorporates that analog into the nascent and growing nucleic acid strand. In one aspect, incorporation can result in a label being released, e.g., in polyphosphate analogs, cleaving between the $\alpha$ and $\beta$ phosphorus atoms in the analog, and consequently releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. For additional information on single molecule sequencing monitoring incorporation of phosphate-labeled analogs in real time, see, e.g., Eid et al. (2009) "Real-time DNA sequencing from single polymerase molecules" Science 323:133-138.

In addition to their use in sequencing, the polymerases of the invention are also useful in a variety of other genotyping analyses, e.g., SNP genotyping using single base extension methods, real time monitoring of amplification, e.g., RT-PCR methods, and the like. Further details regarding sequencing and nucleic acid amplification can be found, e.g., in Sambrook, Ausubel, and Innis, all infra.

Modified Recombinant Polymerases with Increased Closed Complex Stability

The invention features methods of generating recombinant DNA polymerases with modifications that increase the stability of the closed polymerase/DNA complex, compositions that include such polymerases, and methods of using such modified polymerases to, e.g., sequence a DNA template or make a DNA. Any of a number of polymerases, e.g., those described herein or polymerases homologous to those described herein, can be modified to exhibit increased closed polymerase/DNA complex stability using the methods described herein. In a preferred embodiment, a Φ29 polymerase and Φ29 polymerase derivatives, e.g., exonuclease-deficient Φ29 mutants, Φ29-type polymerases, or polymerases homologous to Φ29, can be modified to exhibit this phenotype.

Figure 1A:
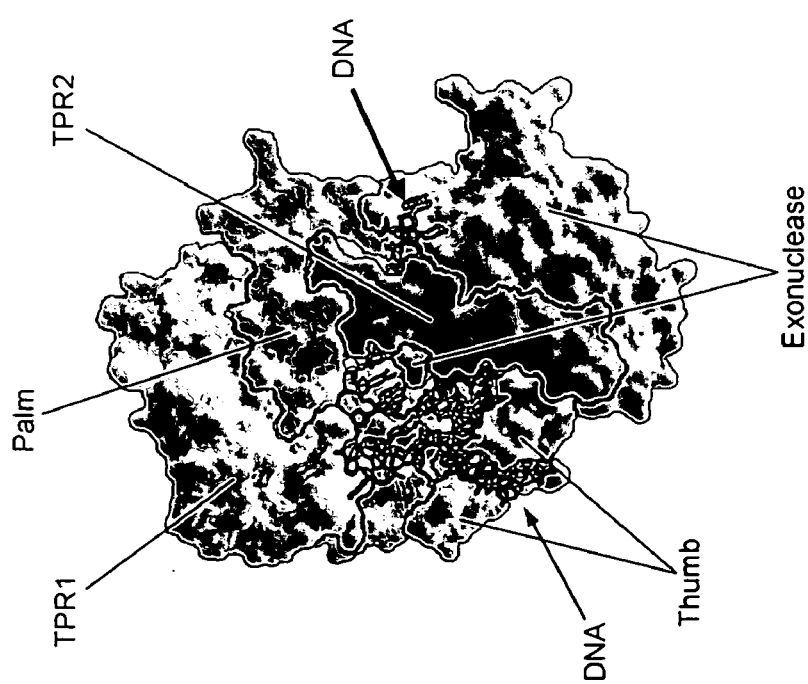

A closed polymerase/DNA complex is formed, e.g., by Φ29 DNA polymerase, when the Terminal Protein Region 2 (TPR2), exonuclease, thumb, and palm subdomains of Φ29 (FIG. 1 Panels A and B) encircle the DNA binding groove at the polymerization active site, forming a "doughnut" (FIG. 1 Panel B and FIG. 2 Panel A) around the upstream duplex DNA. This conformation enhances polymerase processivity in a manner analogous to sliding clamp proteins (Kamtekar, et al. (2004) "Insights into strand displacement and processivity from the crystal structure of the protein-primed DNA polymerase of bacteriophage phi29." Mol. Cell 16: 1035-6). The other Φ29 subdomains represented in FIG. 1 include TPR1 and fingers. It is worth noting that closed complex formation can be independent of the presence of a nucleotide or nucleotide analog.

Φ29 DNA polymerase mutants lacking the TPR2 subdomain exhibit drastically decreased processivity (Rodriguez, et al. (2005) "A specific subdomain in Φ2 polymerase confers both processivity and strand-displacement capacity" Proc Natl Acad Sci USA 102: 6407-6412), indicating that mutations that stabilize the protein-protein interactions at the interface of these subdomains (FIG. 2 Panel B, example circled) can increase the stability of the closed complex comprising the polymerase and DNA, e.g., a template strand and a primer. An increase in closed polymerase/DNA complex stability can comprise an improvement of at least 30%, e.g., 50% or better, 75% or better, or even 100% or better.

Mutations that increase the stability of the closed polymerase/DNA complex can indirectly improve polymerase processivity and can generate polymerases that can be of beneficial use in any application where increased read length, speed and accuracy of polymerization is desirable, e.g., single-molecule sequencing (SMS), e.g., in a zero-mode waveguide (ZMW), SNP genotyping using single base extension methods, real time monitoring of amplification, e.g., RT-PCR methods, and the like. Useful compositions comprising such polymerases can include nucleotide analogs, e.g., analogs labeled with fluorophores, phosphate-labeled nucleotide analogs, and/or labeled nucleotide analogs having, e.g., 3-7 phosphate groups, that the polymerase can incorporate into a DNA. In some embodiments of the compositions, a modified polymerase with improved closed polymerase/DNA complex stability can be immobilized on a surface, e.g., in a ZMW.

Figure 2B:
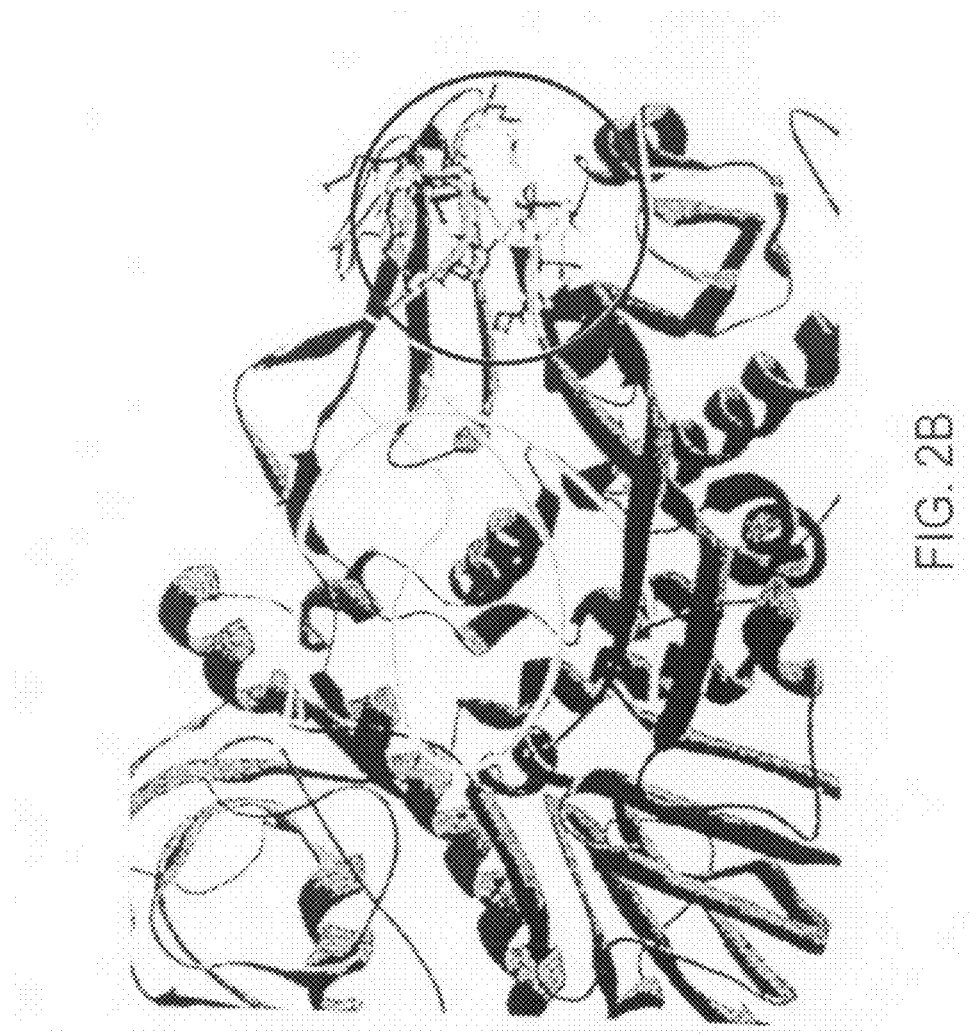
FIG. 2 Panels A and B depict the interface of the TPR2, thumb, and exonuclease subdomains of a Φ29 polymerase complexed with a DNA.
Figure 2A:
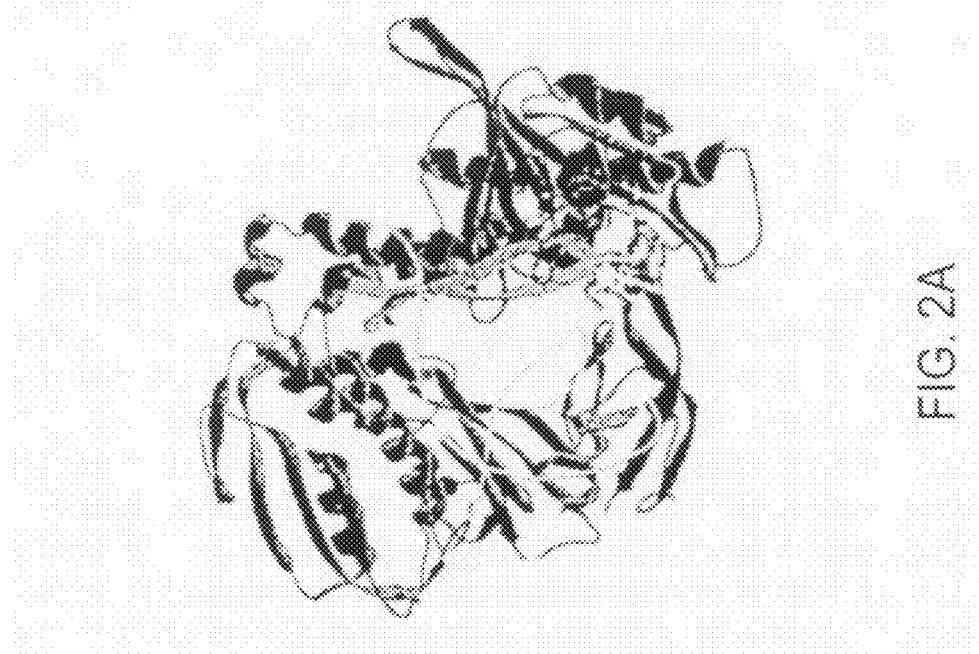

Mutations that can stabilize a closed polymerase/DNA complex include mutations to amino acids regions that correspond to Ala68-Arg76, Tyr405-Gly413, and Gln560-Gly564 of wild type Φ29. These amino acid regions comprise the interface of the exonuclease, TPR2, and thumb subdomains, respectively, and are depicted in FIG. 2 Panels A and B. Mutation of Thr92, in the exonuclease domain, can also stabilize interaction with TPR2 domain. Mutations can be introduced into one or more of these residues to provide additional stability to the closed complex, e.g., by stabilizing the interface of the exonuclease, TPR2, and thumb domains. For example, the hydrophobic environment between domains can be increased to increase complex stability, charged residues can be introduced to add favorable electrostatic interactions (or removed to remove unfavorable interactions), hydrogen bonds can be introduced, and the like. In general terms, a mutation can introduce an intramolecular interaction between domains that is predicted to stabilize the interface (and thus the closed complex) and/or can remove an interaction predicted to destabilize the interface. Thus, strategic mutations such as Thr92Phe, Thr92Ile, Gly410Asp, Asn72Ala, Asn72Ile, Asn72Phe, or Asn72Ser, or combinations thereof such as Thr92Ile and Gly104Asp, can stabilize a closed polymerase/DNA complex. Strategies for mutating and screening polymerases are detailed herein.

Increases in the stability of a closed polymerase/DNA complex can be measured by comparing a rate of dissociation or the dissociation rate constant ($k_{off}$) of the modified polymerase from a DNA to $k_{off}$ of the parental polymerase from a DNA. Decreases in $k_{off}$ can correspond to an increase in closed complex stability. In one preferred embodiment, $k_{off}$ can be determined by, e.g., stopped-flow fluorometric analysis, incubating a fluorescently labeled DNA template, e.g., 2-aminopurine-labeled DNA, with a modified polymerase in the presence of an excess of competitor, e.g., unlabelled DNA or heparin. In another embodiment, a preformed complex comprising a modified polymerase and a template DNA can be incubated in the presence of excess competitor DNA or heparin. A time course of activity assays, e.g., primer extension, can measure the fraction of polymerase that remains associated with template. As indicated above, $k_{off}$ is optionally decreased by at least 30%, e.g., by at least 50%, at least 75%, or at least 100%, for the modified recombinant polymerase as compared to the parental polymerase.

Increases in the stability of a closed polymerase/DNA complex can also be measured by determining the equilibrium dissociation constant $K_d$, where a decrease in $K_d$ can correspond to increased closed complex stability. Optionally, $K_d$ is decreased by at least 30%, e.g., by at least 50%, at least 75%, or at least 100%, for the modified recombinant polymerase as compared to the parental polymerase. $K_d$ can be determined using techniques known in the art, for example, surface plasmon resonance (SPR), fluorescent anisotropy measurements, gel mobility shift assays, or isothermal titration calorimetry (ITC).

Processivity can be defined as the modified polymerase's extension rate constant ($k_{ext}$) divided by the sum of the extension rate constant and the rate constant for dissociation of the modified polymerase from a DNA ($k_{off}$), e.g., $k_{ext}/(k_{ext}+k_{off})$. As described herein, mutations in a polymerase that improve the stability of a closed polymerase/DNA complex can result in a measurable decrease in $k_{off}$, which can, accordingly, improve the polymerase's processivity, such that the modified polymerase's processivity is, e.g., at least twice that of the polymerase from which is was derived, or better. In a related aspect, a modified polymerase's processivity can be improved by increasing its extension rate, a phenotype which can be dependent on the type of nucleotide and/or nucleotide analog assayed. The extension rate constant can be determined using techniques known in the art. See, e.g., Korlach et al. (2008) "Long, processive enzymatic DNA synthesis using 100% dye-labeled terminal phosphate-linked nucleotides" Nucleosides Nucleotides Nucleic Acids 27(9):1072-83 (defined as $k_{et}$).

Modified Recombinant Polymerases with Decreased Branching Fraction

During a polymerase kinetic cycle, sampling of each of the possible nucleotides or nucleotide analogs occurs until a correct Watson-Crick pairing is generated (see, e.g., Hanzel, et al. WO 2007/076057 POLYMERASES FOR NUCLEOTIDE ANALOGUE INCORPORATION for a description of the kinetic cycle of a polymerase; see also the section entitled "Polymerase Mediated Synthesis" hereinbelow). According to structural studies of DNA polymerases complexed with DNA substrates, the primer-terminus can not typically form a covalent bond with an incorrectly paired nucleotide (Berman, et al. (2007) "Structures of phi29 polymerase complexed with substrate: the mechanism of translocation in polymerases." EMBO J 26: 3494-3505). Chemical linkages between a correctly paired nucleotide and the 3'OH of a preceding base can also fail to form, e.g., due to premature release of the sampled nucleotide from the active site. Sampling is then repeated for the same site, eventually resulting in the physical incorporation of the correct nucleotide. However, the premature release can be misread as an incorporation event by a readout system during, e.g., single molecule sequencing, e.g., where the system monitors residence time of the nucleotide analog at the active site as a proxy for incorporation; this can result in sequence read errors which include a nucleotide "insertion" relative to the correct sequence. This phenomenon is termed "branching" and can generate high error rates in single molecule sequencing, especially when chemically modified nucleotides or nucleotide analogs are used.

Among other aspects, the invention provides methods for generating recombinant polymerases that comprise modifications that reduce the frequency of branching, which can be useful in any number of applications where accuracy of polymerization is beneficial, e.g., high-throughput sequencing systems, e.g., in a zero-mode waveguide (ZMW), SNP genotyping using single base extension methods, real time monitoring of amplification, e.g., RT-PCR methods, and the like. Also provided are compositions that include such polymerases and methods in which these polymerases can be useful in, e.g., sequencing or making a DNA. In some embodiments, the compositions can also include a nucleotide analog, e.g., a phosphate-labeled nucleotide analog, an analog labeled with a fluorophore, and/or a nucleotide analog comprising from 3-7 phosphate groups, which can be incorporated into a copy nucleic acid by the modified polymerase in response to a DNA template. In some embodiments, the compositions can be present in a sequencing system, e.g. in a zero-mode waveguide, where a polymerase of the invention can optionally be immobilized on a surface.

Modification of a polymerase, e.g., any of the polymerases described herein, or polymerases homologous to those described herein, by any one or more of the strategies described herein can lower the frequency of these events by creating a more tightly structured binding pocket for non-native nucleotides. Modified polymerases can comprise at least one amino acid substitution or a combination of amino acid substitutions relative to the parental polymerase, such as those listed in Table 1. The modified polymerases can also comprise additional mutations, e.g., T368D, T368E, T368G, E375Y, E375W, K512Y, K512F, K512W, K512L, K512I, K512V, or K512H substitutions or other mutations described herein. In one embodiment, a polymerase that exhibits a reduced branching frequency can comprise at least one mutation that provides other useful features such as reduced exonuclease activity (e.g., N62D, D12A, D66A, and/or T15I substitutions relative to a wild-type Φ29 polymerase).

A number of specific examples of a modified polymerase, e.g. modified to lower the frequency of branching events, are described herein. The binding pocket is a portion of the polymerase that encompasses the nucleotide binding site and analog base during the pairing of a nucleotide analog with a template DNA. Because of the physical proximity of the binding pocket to the incoming nucleotide or nucleotide analog, mutations to this region can affect the branching fraction. However, mutations that lower the branching fraction are not limited to this area of the polymerase. For example, relative to a wild-type Φ29 DNA polymerase, these modifications, in addition to those described above, can include any one of, or any combination of: an amino acid substitution at position 153, an amino acid substitution at amino acid position 191, an amino acid substitution at position 388, an amino acid substitution at position 422, an amino acid substitution at position 128; an amino acid substitution at position 253; an amino acid substitution at position 504; an amino acid substitution at position 143; an amino acid substitution at position 183; an amino acid substitution at position 236; an amino acid substitution at position 363; and/or any of the following mutations or combinations thereof: P153L; G191A; T368F; T368P; T368S; T368V; T368N; T368A; T373N; T373V; T373C; I378V; I378F; K379S; K379A; S388A; S388T; K422R; F128M; F128V; I504V; K143D; K512R; Q183S; R236N; L253A; F363Y; L253A, F363Y, and L480M; T368F, K379S, E375Y, and K512Y; T368F and K379S; T368G and K379S; T368F and T373A; E375Y, K512Y and K379S; E375Y, K512Y and T368F; T368F and V514K; T368F and K379T; S388A and P153L; E375Y, K512Y and T368G; T368G and T373A; E375W and T368G; I378K and K379S; T368F and I378K; T368G and I378K; T368G and V514K; E375W and K379T; T373A and K379S; E375W and T373A; E375Y, K512Y and T373A; E375W and I378K; E375Y, K512Y and I378K; T373A and V514K; T373A and I378K; E375Y, K512Y and K379T; I378K and V514K; E375W and V514K; T368G and K379T; and E375Y, K512Y and V514K. A list of specific useful Φ29 mutants and the corresponding reduced branching fraction that they exhibit is provided in Table 1 below. For comparison, wild-type Φ29 polymerase exhibits a branching fraction of about ≧40% for, e.g., an A488dA4P nucleotide analog. Values in Table 1 were determined as described in Example 1.

TABLE 1

| Mutation Name | Branching Fraction (%) |
|---|---|
| N62D_T368F_K379S_E375Y_K512Y | 8.01 |
| N62D_T368F_K379S | 6.47 |
| N62D_T368P | 6.58 |
| N62D_T368G_K379S | 6.96 |
| N62D_T368F_T373A | 6.99 |
| N62D_T368S | 7.32 |
| N62D_E375Y_K512Y_K379S | 7.66 |
| N62D_E375Y_K512Y_T368F | 8.53 |
| N62D_T368F_V514K | 8.58 |
| N62D_T368F_K379T | 8.71 |
| N62D_S388A_P153L | 8.93 |
| N62D_T368V | 9.94 |
| N62D_E375Y_K512Y_T368G | 10.14 |
| N62D_T368D | 10.41 |
| N62D_T368G_T373A | 10.69 |
| N62D_T368N | 10.73 |
| N62D_E375W_T368G | 12.04 |
| N62D_G191A | 12.32 |
| N62D_I378K_K379S | 12.47 |

TABLE 1-continued

| Mutation Name | Branching Fraction (%) |
|---|---|
| N62D_K379A | 12.75 |
| N62D_T368F_I378K | 13.30 |
| N62D_K379S | 13.34 |
| N62D_T368F | 13.55 |
| N62D_T368G_I378K | 13.59 |
| N62D_T368G_V514K | 14.01 |
| N62D_E375W_K379T | 14.66 |
| N62D_T373A_K379S | 14.72 |
| N62D_S388T | 14.82 |
| N62D_E375W_T373A | 16.40 |
| N62D_T368A | 16.60 |
| N62D_I378V | 17.38 |
| N62D_E375Y_K512Y_T373A | 17.54 |
| N62D_T373N | 17.63 |
| N62D_E375W_I378K | 17.70 |
| N62D_E375Y_K512Y_I378K | 17.83 |
| N62D_T373A_V514K | 17.87 |
| N62D_T373A_I378K | 17.89 |
| N62D_T373V | 18.26 |
| N62D_I378F | 18.32 |
| N62D_E375Y_K512Y_K379T | 18.72 |
| N62D_I378K_V514K | 18.74 |
| N62D_T368E | 18.82 |
| N62D_E375W_V514K | 19.68 |
| N62D_T368G_K379T | 19.77 |
| N62D_T373C | 20.54 |
| N62D_K422R | 20.68 |
| N62D_T368G | 21.48 |
| E375Y_K512Y_V514K | 24.90 |
| N62D_F128M | 8.86 |
| N62D_F128V | 8.35 |
| L253A_F363Y_L480M | 9.59 |
| N62D_I504V | 5.24 |
| N62D_K143D | 9.66 |
| N62D_K512R | 8.63 |
| N62D_Q183S | 9.62 |
| N62D_R236N | 9.71 |

Figure 3:
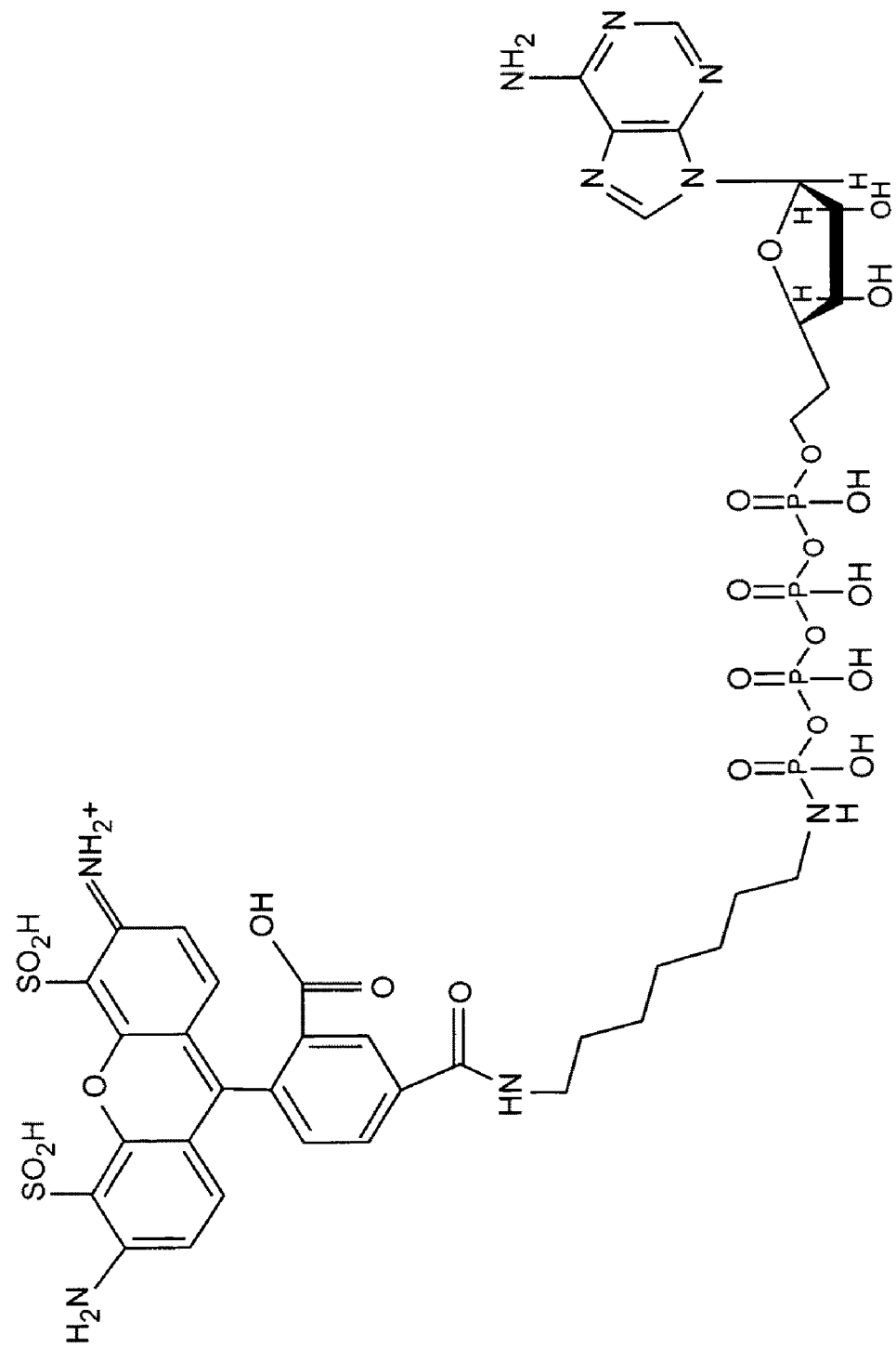
FIG. 3 depicts the structure of A488dA4P.

As noted, the branching fraction, e.g., % branching, is a relative measure of the number of times a correctly paired base, e.g., a Watson-Crick paired base, leaves the active site of the polymerase without forming a phosphodiester bond with the 3'OH of the primer-terminus relative to the total number of interactions that occur between the nucleotide (or nucleotide analog) and the binding pocket of the polymerase, e.g., the total number of opportunities the nucleotide or nucleotide analog, e.g., A488dA4P in FIG. 3, has to correctly pair and incorporate. Branching is expressed as a percentage of the dissociation events vs. the total sum events, e.g., dissociation and association events. For example, for an N62D/T368G Φ29 mutant polymerase, for every 100 times an A488dA4P analog interacts with the binding pocket of this polymerase, 21.477 of the events are non-productive dissociation events, e.g., wherein the analog dissociates from the polymerase instead of participating in a polymerization reaction.

The branching fraction is measured by "loading" a polymerase active site with a cognate-matching nucleotide analog that can bind in the +1 and +2 positions. In the absence of divalent cation this nucleotide cannot be incorporated into the DNA strand, so will pair with the template nucleotide at the +1 position but be released at some frequency specific for that analog/polymerase combination, e.g., the branching rate. This 'loading' reaction is then followed by a 'chase' reaction consisting of a divalent cation that supports extension, e.g., $Mn^{2+}$), and a terminating-type nucleotide analog, e.g., a dideoxynucleotide, comprising the same base as the cognate-matching analog in the loading step.

The dideoxy-analog will be incorporated into any +1 sites that are unoccupied and, once added, preclude further extension. Hence polymerase active sites that are already occupied by a paired analog base extend to the +2 position, while those that are not occupied (i.e. "branched") incorporate the dideoxy-type analog at +1 and do not extend, resulting in a single base addition. The extension products of this reaction are visualized by standard separation methods, e.g., gel or capillary electrophoresis, and the ratio of terminated product that is generated when a dideoxynucleotide is incorporated at the +1 position divided by the total terminated product, e.g., when a dideoxynucleotide is incorporated at both the +1 and +2 positions, indicates the fraction of 'branched' events that occur.

The branching fraction exhibited by a modified polymerase, e.g., a modified Φ29 polymerase, a modified Φ29-type polymerase, or a modified exonuclease-deficient Φ29 polymerase, can be less than a branching fraction exhibited by the parental polymerase for a given nucleotide analog or, e.g., less than 25% for a phosphate-labeled nucleotide analog, less than 20% for the phosphate-labeled analog, less than 15% for the phosphate-labeled analog, or less than 10% for the phosphate-labeled analog.

In some embodiments, the modified polymerase that exhibits a reduced frequency of branching can also exhibit a $K_m$ for a given phosphate-labeled nucleotide analog, e.g., any of the phosphate-labeled nucleotide analogs described herein, that is less than 10 µM. For enzymes obeying simple Michaelis-Menten kinetics, kinetic parameters are readily derived from rates of catalysis measured at different substrate concentrations. The Michaelis-Menten equation, $V=V_{max}[S]$ $([S]+K_m)^{-1}$ relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V). To determine a $K_m$ for a particular analog a series of extension reactions are performed with a varying concentration of the analog of interest with a fixed, saturating concentration of native nucleotides. A fit of the rate versus the substrate concentration generates estimation of the $-K_m$ as the slope of this line. Modified polymerases that exhibit reductions in branching fraction can also exhibit increased accuracy of nucleotide incorporation. The modified polymerases optionally exhibit improved specificity, e.g., as assessed by determining $k_{cat}/K_m$.

Modified Recombinant Polymerases with Slow Steps

The invention also features recombinant polymerases with modifications that decrease the rate of one or more steps within the catalytic cycle, for example, to achieve a reaction system having two kinetically observable reaction steps within an observable phase of the polymerase reaction. Such systems can be useful for observing the activity of a polymerase enzyme in real time, for example, for carrying out single molecule nucleic acid sequencing. For example, a system in which the reaction kinetics exhibit two slow steps within an observable phase can result in more observable sequencing events, allowing for a more accurate determination of a nucleic acid sequence.

In single molecule DNA sequencing by synthesis, for example as described in Eid et al. (2009) Science 323(5910): 133-138, the incorporation of specific nucleotides can be determined by observing bright phases and dark phases which correspond, for example, to reaction steps in which a fluorescent label is associated with the polymerase enzyme, and steps in which the fluorescent label is not associated with the enzyme. In some embodiments of the invention, the polymerase reaction system will exhibit two sequential slow (kinetically observable) reaction steps wherein each of the steps is in a bright phase. In some embodiments of the invention, the system will exhibit two sequential slow reaction steps wherein each of the steps is in a dark phase. In some embodiments, the system will have four slow reaction steps, two slow steps in a bright phase and two slow steps in a dark phase. In some cases, the two or more slow steps are consecutive. In some cases, there can be intervening fast steps between the two or more slow steps.

An observable phase will generally have a time period during which it is observable. The time period for a bright phase, for example, can be represented by the pulse width. The time period for a dark phase can be represented, for example, by the interpulse distance. The length of each time period will not be the same for each nucleotide addition, resulting in a distribution of the length of the time periods. In some cases, the time periods with the shortest length will not be detected, leading to errors in single molecule sequencing. By designing polymerase reaction systems in which there are two slow, or kinetically observable, steps within an observable phase, the relative number of short, unobservable, time periods can be reduced, resulting in a higher proportion of observable sequencing events and allowing for a more accurate determination of nucleotide sequence. For example, having two slow steps within a bright phase can reduce the incidence of very short pulses, while having two slow steps within a dark phase can reduce the incidence of very short interpulse distances (which occasionally cause pulse merging).

The modified recombinant polymerases with decreased reaction rates described hereinbelow are desirably employed to obtain such a system with two (or more) slow reaction steps. Optionally, the polymerase reaction conditions, including the type and levels of cofactors, and/or the reaction substrates are also manipulated to achieve such a system, as described in U.S. patent application Ser. No. 12/414,191 filed Mar. 30, 2009, and entitled "Two slow-step polymerase enzyme systems and methods."

Polymerase Mediated Synthesis

In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation is relatively complex.

The process can be described as a sequence of steps, wherein each step can be characterized as having a particular forward and reverse reaction rate that can be represented by a rate constant. One representation of the incorporation biochemistry is provided in FIG. 12. It is to be understood that the scheme shown in FIG. 12 does not provide a unique representation of the process. In some cases, the process can be described using fewer steps. For example, the process is sometimes represented without inclusion of the enzyme isomerization steps 106 and 110. Alternatively, the process can be represented by including additional steps such as cofactor binding. Generally, steps which can be slow, and thus limit the rate of reaction, will tend to be included. Various schemes can be used to represent a polymerization reaction, e.g., having one or two slow steps, that may have more or fewer identified steps.

Figure 12:
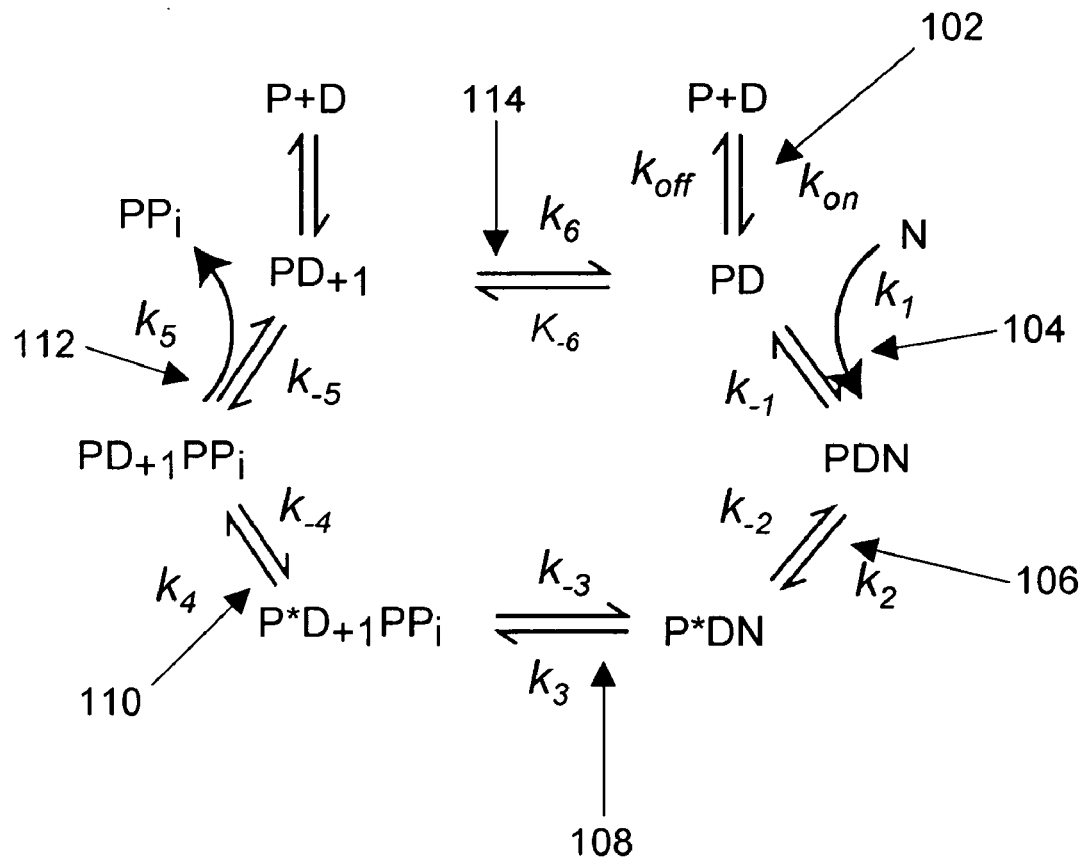
FIG. 12 schematically illustrates the catalytic cycle for polymerase-mediated nucleic acid primer extension.

As shown in FIG. 12, the synthesis process begins with the binding of the primed nucleic acid template (D) to the polymerase (P) at step 102. Nucleotide (N) binding with the complex occurs at step 104. Step 106 represents the isomerization of the polymerase from the open to closed configuration. Step 108 is the chemistry step where the nucleotide is incorporated into the growing strand of the nucleic acid being synthesized. At step 110, polymerase isomerization occurs from the closed to the open position. The polyphosphate component that is cleaved upon incorporation is released from the complex at step 112. The polymerase then translocates on the template at step 114. As shown, the various steps can include reversible paths and may be characterized by the reaction constants shown in FIG. 12 where:

$k_{on}/k_{off}$=DNA binding/release;
$k_1/k_{-1}$=nucleotide binding/release;
$k_2/k_{-2}$=polymerase isomerization (open/closed);
$k_3/k_{-3}$=nucleotide incorporation (chemistry);
$k_4/k_{-4}$=polymerase isomerization (closed/open);
$k_5/k_{-5}$=polyphosphate release/binding;
$k_6/k_{-6}$=polymerase translocation.

Thus, during steps 104 through 110, the nucleotide is retained within the overall complex, and during steps 104 and 106, reversal of the reaction step will yield an unproductive event, i.e., not resulting in incorporation. For example, a bound nucleotide at step 104 may be released regardless of whether it is the correct nucleotide for incorporation.

By selecting the appropriate polymerase enzyme, polymerase reaction conditions, and polymerase substrates, the absolute and relative rates of the various steps can be controlled. Controlling the reaction such that the reaction exhibits two or more sequential kinetically observable, or slow, steps can produce a nucleic acid polymerization reaction in which the incorporation of the nucleotides can be observed more accurately. These characteristics are particularly useful for sequencing applications, and in particular single molecule DNA sequencing.

In some cases, the invention involves a process having two or more slow steps that comprise steps after nucleotide binding through the step of product release. For the mechanism shown in FIG. 12, this would be, for example, any of steps 106, 108, 110, and 112. In some cases, steps 108 (nucleotide incorporation) and 112 (product release) are the two slow steps. In some cases, the invention involves a process having two or more slow steps that comprise the steps after product release through nucleotide binding. For the mechanism shown in FIG. 12, this would include steps 114 and 104.

In some cases, the invention involves a process in which there are two or more slow steps in two different observable phases within the polymerization, for example, two slow steps in a bright phase and two slow steps in a dark phase. For example, this could include a system having two slow steps in the steps after nucleotide binding through product release, and two slow steps for the steps after product release through nucleotide binding. As is described herein, producing a process in which there are two slow steps in these portions of the polymerase reaction can result in a higher proportion of detectable enzyme states which can be useful, for example, to observe the sequential incorporation of nucleotides for nucleotide sequencing.

By the term slow step is generally meant a kinetically observable step. An enzymatic process, such as nucleic acid polymerization, can have both slower, kinetically observable steps and faster steps which are so fast that they have no measurable effect on the kinetics, or rate, of the reaction. In some reactions, there can be a single rate limiting step. For such reactions, the kinetics can be characterized by the rate of that single step. Other reactions will not have a single rate limiting step, but will have two or more steps which are close enough in rate such that the characteristics of each will contribute to the kinetics of the reaction. For the current invention, the slow, or kinetically observable, steps need not be the slowest step or the rate limiting step of the reaction. For example, a process of the current invention can involve a reaction in which step 104, nucleotide addition, is the slowest (rate limiting) step, while two or more of steps 106, 108, 110, or 112 are each kinetically observable.

As used herein, the term rate as applied to the steps of a reaction can refer to the average rate of reaction. For example, when observing a single molecule reaction, there will generally be variations in the rates as each individual nucleotide is added to a growing nucleic acid. In such cases the rate of the reaction can be represented by observing a number of individual events, and combining the rates, for example, by obtaining an average of the rates.

As used herein, the reference to the rate of a step or rate constant for a step can refer to the forward reaction rate of the polymerase reaction. As is generally understood in the art, reaction steps can be characterized as having forward and reverse rate constants. For example, for step 108, $k_3$ represents the forward rate constant, and $k_{-3}$ represents the reverse rate constant for the nucleotide incorporation. Some reaction steps, such as step 108, constitute steps which would be expected to be first order steps. Other steps, such as the forward reaction of step 104, with rate constant $k_2$, would be expected to be second order rate constants. For the purposes of the invention, for comparing the rate or the rate constant of a first order to a second order step, the second order rate constant $k_2$ can be treated as a pseudo-first order rate constant with the value $[N]*k_2$ where the concentration of nucleotide [N] is known.

For some applications, it is desirable that the kinetically observable steps of the invention have rate constants that are lower than about 100 per second. In some cases, the rate constants are lower than about 60 per second, lower than about 50 per second, lower than about 30 per second, lower than about 20 per second, lower than about 10 per second, lower than about 5 per second, lower than about 2 per second, or lower than about 1 per second.

In some embodiments the slowest of the two or more kinetically observable steps has a rate constant when measured under single molecule conditions of between about 60 to about 0.5 per second, about 30 per second to about 2 per second, or about 10 to about 3 per second.

The ratio of the rate constants of each the two or more slow steps is generally greater than 1:10; in some cases the ratio of the rate constants is about 1:5, in some cases the ratio of the rate constants is about 1:2, and in some cases, the ratio of rate constants is about 1:1. The ratio of the rate constants can be between about 1:10 and about 1:1, between about 1:5 and about 1:1, or between about 1:2 and about 1:1.

In some cases it is useful to consider the two slow-step system in terms of rates rather than rate constants. It is generally desirable that the kinetically observable steps of the invention have rates that are lower than about 100 molecules per second when the reactions are carried out under single-molecule conditions. In some cases, the rates are lower than about 60 molecules per second, lower than about 50 molecules per second, lower than about 30 molecules per second, lower than about 20 molecules per second, lower than about 10 molecules per second, lower than about 5 molecules per second, lower than about 2 molecules per second, or lower than about 1 molecule per second.

In some embodiments the slowest of the two or more kinetically observable steps has a rate when measured under single molecule conditions of between about 60 to about 0.5 molecules per second, about 30 molecules per second to about 2 molecules per second, or about 10 to about 3 molecules per second.

The ratio of the rates of each the two or more slow steps is generally greater than 1:10. In some cases the ratio of the rates is about 1:5, in some cases the ratio of the rates is about 1:2, and in some cases, the ratio of rates is about 1:1. The ratio can be between about 1:10 and about 1:1, between about 1:5 and about 1:1, or between about 1:2 and about 1:1.

Any one (or more) of the steps described above is optionally slowed in the recombinant polymerases of the invention, e.g., to produce a polymerase useful in achieving a reaction system exhibiting two slow steps.

Sequencing by Incorporation

For sequencing processes that rely upon monitoring of the incorporation of nucleotides into growing nascent strands being synthesized by the complex, the progress of the reaction through these steps is of significant importance. In particular, for certain "real time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene et al. (2003) Science 299:682-686 and Eid et al. (2009) Science 323(5910):133-138, the full disclosures of which are incorporated herein by reference in their entirety for all purposes.

Figure 13A:
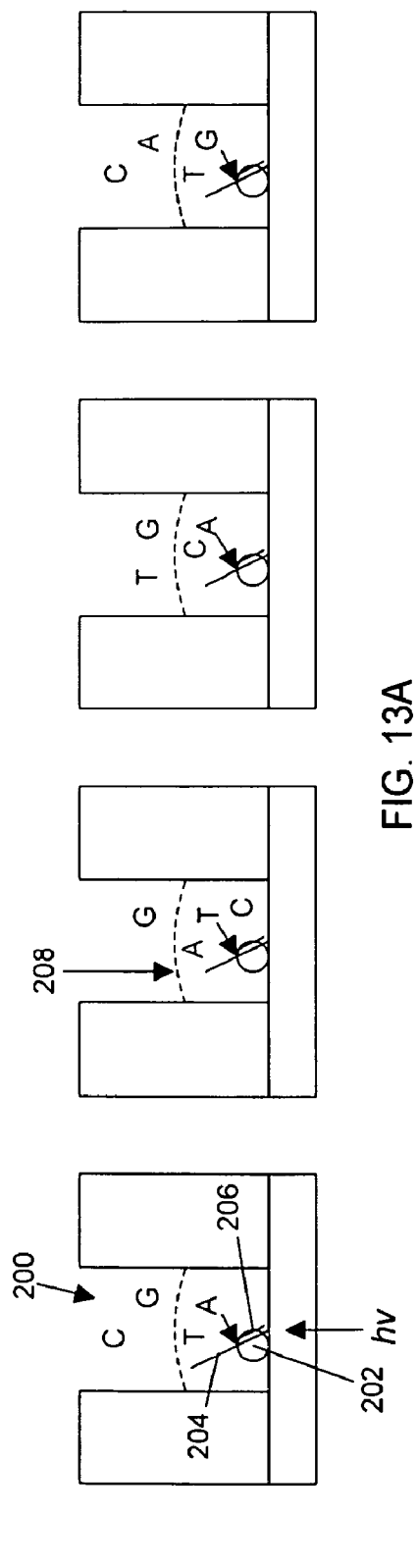
FIG. 13 Panels A and B schematically illustrate an exemplary single molecule sequencing by incorporation process in which the compositions of the invention provide particular advantages.
Figure 13B:
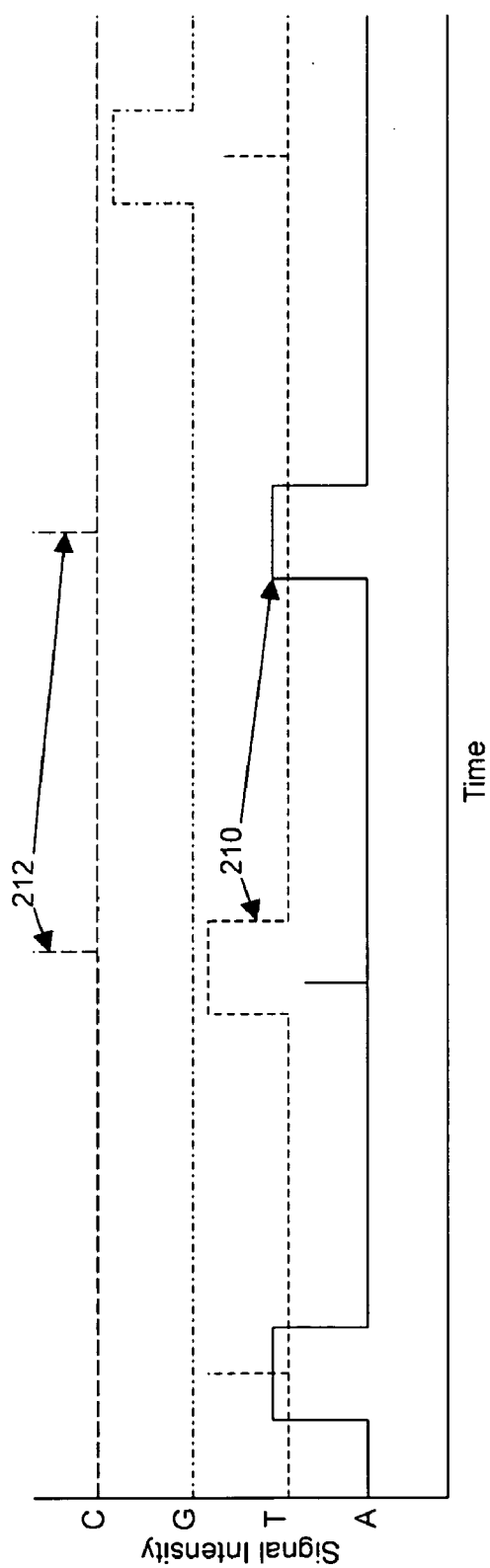

In a first exemplary technique, as schematically illustrated in FIG. 13 Panel A, a nucleic acid synthesis complex, including a polymerase enzyme 202, a template sequence 204 and a complementary primer sequence 206, is provided immobilized within an observation region 200, that permits illumination (as shown by hv) and observation of a small volume that includes the complex without excessive illumination of the surrounding volume (as illustrated by dashed line 208). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particular, as shown in Panel B of FIG. 13, when a nucleotide, e.g., A, is incorporated into by the polymerase, it is retained within the observation volume for a prolonged period of time, and upon continued illumination yields a prolonged fluorescent signal (shown by peak 210). By comparison, randomly diffusing and not incorporated nucleotides remain within the observation volume for much shorter periods of time, and thus produce only transient signals (such as peak 212), many of which go undetected, due to their extremely short duration.

In particularly preferred exemplary systems, the confined illumination volume is provided through the use of arrays of optically confined apertures termed zero mode waveguides (ZMWs), e.g., as shown by confined reaction region 200 (see, e.g., U.S. Pat. No. 6,917,726, which is incorporated herein by reference in its entirety for all purposes). For sequencing applications, the DNA polymerase is typically provided immobilized upon the bottom of the ZMW. See, e.g., Korlach et al. (2008) PNAS U.S.A. 105(4):1176-1181, which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In a second exemplary technique, the immobilized complex and the nucleotides to be incorporated are each provided with interactive labeling components. Upon incorporation, the nucleotide borne labeling component is brought into sufficient proximity to the complex borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal quenching. Upon incorporation and cleavage of the terminal phosphate groups, e.g., bearing a donor fluorophore, the quenching is removed and the resulting characteristic fluorescent signal of the donor is observable.

In exploiting the foregoing processes, where the incorporation reaction occurs too rapidly, it may result in the incorporation event not being detected, i.e., the event speed exceeds the detection speed of the monitoring system. The missed detection of incorporated nucleotides can lead to an increased rate of errors in sequence determination, as omissions in the real sequence. In order to mitigate the potential for missed pulses due to short reaction times, in one aspect, the current invention can result in increased reaction time for incorporations. An advantage of employing polymerases with reduced reaction rates, e.g., polymerases exhibiting decreased rates and/or two slow-step kinetics, is an increased frequency of longer, detectable, binding events. This advantage may also be seen as an increased ratio of longer, detectable pulses to shorter, non-detectable pulses, where the pulses represent binding events.

Single molecule sequencing often involves the optical observation of the polymerase process during the process of nucleotide incorporation, for example, observation of the enzyme-DNA complex. During this process, there are generally two or more observable phases. For example, where a terminal-phosphate labeled nucleotide is used and the enzyme-DNA complex is observed, there is a bright phase during the steps where the label is incorporated with (bound to) the polymerase enzyme, and a dark phase where the label is not incorporated with the enzyme. For the purposes of this invention, both the dark phase and the bright phase are generally referred to as observable phases, because the characteristics of these phases can be observed.

Whether a phase of the polymerase reaction is bright or dark can depend, for example, upon how and where the components of the reaction are labeled and also upon how the reaction is observed. For example, as described above, the phase of the polymerase reaction where the nucleotide is bound can be bright where the nucleotide is labeled on its terminal phosphate. However, where there is a quenching dye associated with the enzyme or template, the bound state may be quenched, and therefore be a dark phase. Analogously, in a ZMW, the release of the terminal phosphate may result in a dark phase, whereas in other systems, the release of the terminal phosphate may be observable, and therefore constitute a bright phase.

For example, consider again the reaction scheme of FIG. 12 in the context of the sequencing by incorporation embodiment described above which utilizes nucleotides having labels on their terminal phosphates. For this system, intermediates PDN, P*DN, P*$D_{+1}PP_i$, and $PD_{+1}PP_i$ would all represent bright states of a bright phase because for each of these intermediates, the label is associated with the polymerase enzyme. In contrast, intermediates $PD_{+1}$ and PD correspond to dark states of a dark phase, because for these intermediates, no dye is associated with the polymerase enzyme. In one aspect of the invention, any step (and preferably any two of the steps) which proceed from a bright intermediate, e.g. steps 106, 108, 110, and 112 of FIG. 12 are slow. By having two or more sequential bright steps that are slow, the relative number of longer pulses and detectable incorporation events increases.

Another example of a polymerase reaction with distinct observable phases is one in which the nucleotide is labeled such that its label does not dissociate from the enzyme upon product release, for example where the nucleotide is labeled on the base or on the sugar moiety. Here, the phase in which the label is associated with the active site of the enzyme (bright or dark) may extend past product release until translocation. For this example, an observable phase may extend from nucleotide binding until translocation.

In addition, the systems of the present invention may have two or more different distinct bright phases, for example, phases that can be distinguished based on different colors, e.g. different fluorescent emission wavelengths in the different observable phases. For all of these cases, it can be advantageous to have more than one rate limiting (kinetically observable) step within a phase. Having more than one rate limiting step within a phase can result in a distribution of pulse widths having relatively fewer undetectable or poorly detectable short pulses.

Figure 14:
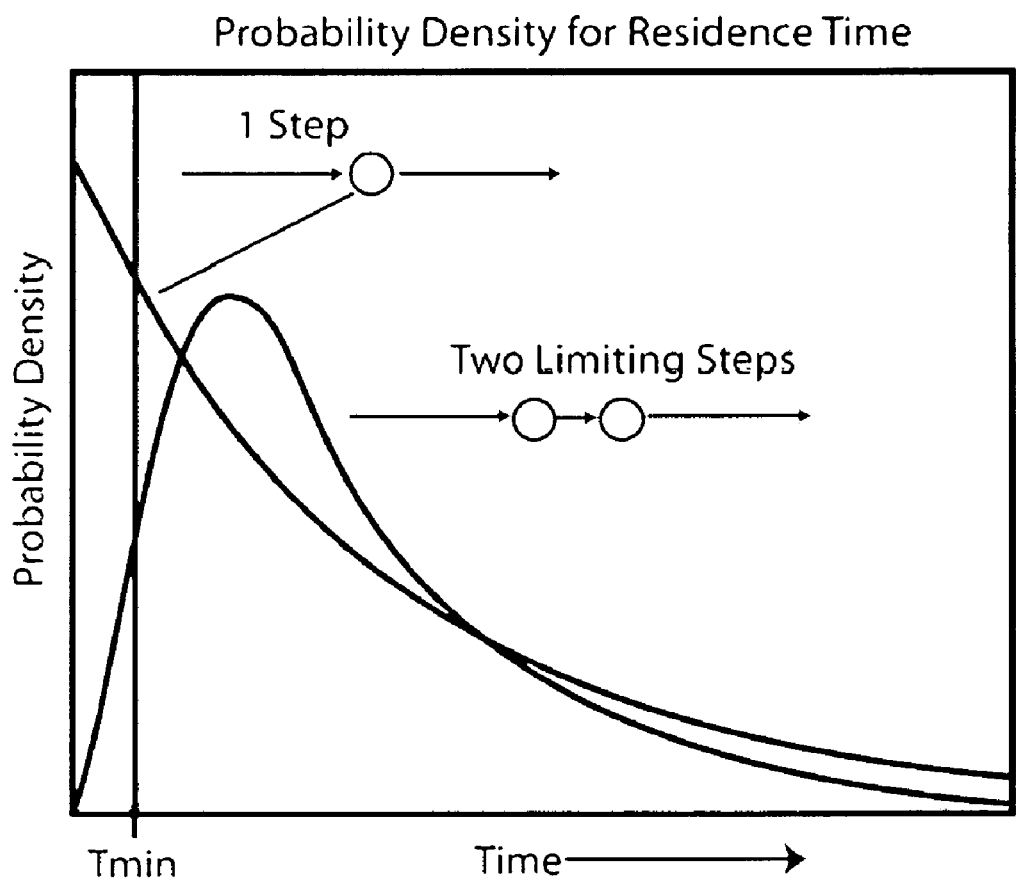
FIG. 14 shows a theoretical representation of the probability density for residence time for a polymerase reaction having one rate limiting step or two rate limiting steps within an observable phase.

While not being bound by theory, the following theoretical basis is provided for obtaining improved single molecule sequencing results by using a system having two or more slow steps. A model for the effect of two slow steps on the probability density for residence time is described herein. FIG. 14 shows a plot of calculated probability density for residence time for cases in which (1) one step is rate limiting and (2) two equivalent rate limiting (slow) steps are present for the observable phase in which the nucleotide is associated with the enzyme.

For the case in which one step is rate limiting, the probability distribution for the binding time can be represented by the single exponential equation:

$$y = A_0 e^{-kt} \qquad \text{Eq. 1}$$

This represents the case in which, for example, incorporation of nucleotide into the growing nucleic acid (step 108 in FIG. 12) is the single slow step.

FIG. 14 illustrates that where one slow-step is present in this phase, there is an exponentially decreasing probability of a given residence time as the residence time increases, providing a distribution in which there is a relatively high probability that the residence time will be short.

For the case in which there are two slow steps in this phase, for example where both the incorporation step (step 108 in FIG. 12) and the release of product (PPi) step (step 112 in FIG. 12) are slow, the probability density versus residence time can be represented by a double exponential equation:

$$y = A_0 e^{-k_1 t} - B_0 e^{-k_2 t} \qquad \text{Eq. 2}$$

FIG. 14 illustrates that for the case in where there are two slow steps, the probability of very fast residence times is relatively low as compared to the case having one slow step. In addition, the probability distribution for two slow steps exhibits a peak in the plot of probability density versus residence time. This type of residence time distribution can be advantageous for single molecule sequencing where it is desired to measure a high proportion of binding events and where fast binding events may be unreliably detected.

Typically, for a given illumination/detection system there will be a minimum detection time below which events, such as binding events, will be unreliably detected or not detected at all. This minimum detection time can be attributed, for example, to the frame acquisition time or frame rate of the optical detector, for example, a CCD camera. A discussion of detection times and approaches to detection for these types of systems is provided in U.S. patent application Ser. No. 12/351,173 the full disclosures of which are incorporated herein by reference in their entirety for all purposes. FIG. 14 includes a line which indicates a point where the residence time equals a minimum detection time (Tmin). The area under the curve in the region below Tmin represents the population of short pulses which will not be accurately detected for this system. It can be seen from FIG. 14 that the relative proportion of binding times that fall below Tmin is significantly lower for the case in which the reaction exhibits two sequential slow steps as compared to the case where the reaction exhibits one slow step.

Thus, as described above, one aspect of the invention relates to methods, systems, and compositions for performing nucleic acid sequencing with a nucleic acid synthesis reaction in which the reaction exhibits two or more slow steps within a bright phase, e.g., employing a modified polymerase exhibiting one or more slowed step. In addition, an aspect of the invention relates to nucleic acid synthesis reactions having two or more slow states wherein each of the slow steps proceeds from a state in which the labeled component is associated with the polymerase enzyme.

In some embodiments of the invention, the two or more slow steps are within a dark phase. In some cases the two or more slow steps proceed from states in which the labeled component is not associated with the enzyme. Having two or more slow states that proceed from a dark intermediate can be advantageous, for example, for lowering the frequency of events having a very short dark state or having a very short interpulse distance. The advantage of this type of system can be demonstrated by again considering FIG. 12 in the context of the sequencing by incorporation embodiment described above which utilizes nucleotides having labels on their terminal phosphates. In this system, intermediates $PD_{+1}$ and PD can correspond to dark states within a dark phase, for example in a ZMW, because for these intermediates, no dye is associated with the polymerase enzyme.

The steps that comprise the two slow steps can include, for example, nucleotide addition, enzymatic isomerization such as to or from a closed state, cofactor binding or release, product release, incorporation of nucleic acid into the growing nucleic acid, or translocation. As noted, one or more of the slow steps can be achieved by modification of the polymerase. Various exemplary modified recombinant polymerases exhibiting one or more slow steps are described herein, along with strategies for producing additional such polymerases.

Modified Recombinant Polymerases Exhibiting Slow Steps

The invention features recombinant polymerases with modifications that slow one or more steps in the catalytic cycle, for example, to achieve two limiting steps as described above. Accordingly, one aspect of the invention provides a modified recombinant DNA polymerase that comprises one or more mutations relative to a parental polymerase and that exhibits a first rate constant for a first step in its catalytic cycle that is less than a first rate constant for the first step exhibited by the parental polymerase. For example, the first rate constant exhibited by the modified recombinant polymerase can be less than 0.5 times, less than 0.25 times, or even less than 0.1 times the first rate constant exhibited by the parental polymerase.

As noted above, to achieve a two slow step enzyme it is typically desirable to decrease the rate of a step which is not already rate limiting. Thus, in one aspect, the first step is not rate limiting in the catalytic cycle of the parental polymerase. Also as noted above, polymerases exhibiting approximately the same rate for two sequential (though not necessarily consecutive) steps are desirable. Thus, the modified recombinant polymerase optionally exhibits a second rate constant for a second step in its catalytic cycle, where the second rate constant is between 0.1 and 10 times the first rate constant. Preferably, the second rate constant exhibited by the modified recombinant polymerase is between 0.2 and 5 times the first rate constant exhibited by the modified recombinant polymerase. More preferably, the second rate constant exhibited by the modified recombinant polymerase is approximately equal to the first rate constant exhibited by the modified recombinant polymerase (e.g., within 10%, 5%, or 1%). In one exemplary embodiment, the second step involves incorporation of a bound nucleotide or nucleotide analog, the first step involves release of a polyphosphate product, and the second rate constant exhibited by the modified recombinant polymerase is between 0.2 and 1 times the first rate constant exhibited by the modified recombinant polymerase. It will be understood that in this context, the terms first step and second step are merely used for convenience in referring to two different steps and do not imply any particular order of occurrence (that is, the first step can precede or follow the second and need not be the initial event in the catalytic pathway).

Optionally, the second step is rate limiting in the catalytic cycle of the parental polymerase. The first or second step can be rate limiting in the catalytic cycle of the modified polymerase. As another option, however, the first and/or second steps are not rate limiting for the catalytic cycle, but are limiting for a portion of the cycle (e.g., the bright or dark portion). Optionally, the polymerase exhibits two limiting steps in the bright portion of the cycle and two in the dark portion.

Since for many polymerases nucleotide incorporation is rate limiting, the second step can, for example, involve incorporation of a bound nucleotide or nucleotide analog, e.g., an analog having from 3-7 phosphate groups, e.g., with a terminal label. The second rate constant would then be $k_3$ according to the catalytic cycle illustrated in FIG. 12.

Essentially any step in the cycle can correspond to the first step whose rate is slowed, for example, translocation, isomerization, e.g., of the polymerase or analog, chemistry (incorporation or transphosphorylation), pre-product release isomerization, and product release. Optionally, an extra kinetic step is created that does not occur in the parental enzyme's cycle. In one exemplary class of useful embodiments, the first step involves release of a polyphosphate product, including, for example (and depending on the type of nucleotide or analog incorporated), a pyrophosphate, a polyphosphate with three or more phosphate groups, a labeled polyphosphate, etc. Polyphosphate release is typically so fast as to be undetectable by routine techniques, but in the polymerases of the invention release can be sufficiently slowed as to be observable and permit determination of a rate constant (e.g., $k_5$). Accordingly, the first rate constant exhibited by a modified recombinant polymerase for release of polyphosphate can be less than 100/second, less than 75/second, or even less than 50/second.

The parental and modified polymerases can display comparable rates for the second step, or the second step can also be slowed for the recombinant polymerase. Thus, the second rate constant exhibited by the modified recombinant polymerase is optionally smaller than the second rate constant exhibited by the parental polymerase for the second step, e.g., less than 0.5 times, less than 0.25 times, or even less than 0.1 times the second rate constant exhibited by the parental polymerase.

A modified polymerase (e.g., a modified recombinant Φ29-type DNA polymerase) that exhibits one or more slow steps optionally includes a mutation (e.g., an amino acid substitution or insertion) at one or more of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, 390, 372-397, and 507-514, where numbering of positions is relative to wild-type Φ29 polymerase. For example, relative to wild-type Φ29 a modified recombinant polymerase can include at least one amino acid substitution or combination of substitutions selected from the group consisting of: an amino acid substitution at position 484; an amino acid substitution at position 198; an amino acid substitution at position 381; an amino acid substitution at position 387 and an amino acid substitution at position 484; an amino acid substitution at position 372, an amino acid substitution at position 480, and an amino acid substitution at position 484; an amino acid substitution at position 372, an amino acid substitution at position 387, and an amino acid substitution at position 480; an amino acid substitution at position 372, an amino acid substitution at position 387, and an amino acid substitution at position 484; an amino acid substitution at position 372, an amino acid substitution at position 387, an amino acid substitution at position 478, and an amino acid substitution at position 484; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F. A K512F substitution (or K512W, K512L, K512I, K512V, K512H, etc.) is optionally employed, e.g., where a K512Y substitution is listed herein. As another example, the modified polymerase can include an insertion of at least one amino acid (e.g., 1-7 amino acids, e.g., glycine) within residues 372-397 and/or 507-514. For example, a glycine residue can be introduced after residue 374, 375, 511, and/or 512 (designated as 374.1G, 375.1G, etc.).

A list of exemplary mutations and combinations thereof is provided in Table 2, and additional exemplary mutations are described herein. Essentially any of these mutations, or any combination thereof, can be introduced into a polymerase to produce a modified recombinant polymerase (e.g., into wild-type Φ29, an exonuclease deficient Φ29-type polymerase, and/or E375Y/K512Y/T368F Φ29, as just a few examples).

TABLE 2

| Mutation | Rationale |
| --- | --- |
| D249E | metal coordination |
| A484E | metal coordination |
| D249E/A484E | metal coordination |
| A484D | metal coordination |
| A484H | metal coordination |
| A484Y | metal coordination |
| D249E/A484D | metal coordination |
| D249E/A484H | metal coordination |
| D249E/A484Y | metal coordination |
| 374.1G/375.1A | dye interaction |
| 374.1Gins/375.1Gins | dye interaction |
| V514Y | dye interaction |
| V514F | dye interaction |
| 511.1G/K512Y/512.1G | dye interaction |
| T372H | closed conformation of fingers |
| T372V | closed conformation of fingers |
| T372I | closed conformation of fingers |
| T372F | closed conformation of fingers |
| T372Y | closed conformation of fingers |
| T372N | closed conformation of fingers |
| T372Q | closed conformation of fingers |
| T372L | closed conformation of fingers |
| T372L/K478Y | closed conformation of fingers |
| T372Y/K478Y | closed conformation of fingers |
| T372Y/K478L | closed conformation of fingers |
| K478Y | closed conformation of fingers |
| D365N | closed conformation of fingers |
| D365Q | closed conformation of fingers |
| L480H | closed conformation of fingers |
| L480F | closed conformation of fingers |
| L381A | closed conformation of finger and exo |
| I179A | closed conformation of finger and exo |
| I378A | closed conformation of finger and exo |
| I179A/L381A | closed conformation of finger and exo |
| I179A/I378A/L381A | closed conformation of finger and exo |
| I370A/I378A | closed conformation of finger and exo |
| I179A/I370A/I378A/L381A | closed conformation of finger and exo |
| I179W | closed conformation of finger and exo |
| I179H | closed conformation of finger and exo |
| F211A | closed conformation of finger and exo |
| F211W | closed conformation of finger and exo |
| F211H | closed conformation of finger and exo |
| F198A | closed conformation of finger and exo |
| F198W | closed conformation of finger and exo |
| F198H | closed conformation of finger and exo |
| P255A | closed conformation of finger and exo |
| P255W | closed conformation of finger and exo |
| P255H | closed conformation of finger and exo |
| Y259A | closed conformation of finger and exo |
| Y259W | closed conformation of finger and exo |

TABLE 2-continued

| Mutation | Rationale |
| --- | --- |
| Y259H | closed conformation of finger and exo |
| F360A | closed conformation of finger and exo |
| F360W | closed conformation of finger and exo |
| F360H | closed conformation of finger and exo |
| F363A | closed conformation of finger and exo |
| F363H | closed conformation of finger and exo |
| F363W | closed conformation of finger and exo |
| I370W | closed conformation of finger and exo |
| I370H | closed conformation of finger and exo |
| K371A | closed conformation of finger and exo |
| K371W | closed conformation of finger and exo |
| I378H | closed conformation of finger and exo |
| I378W | closed conformation of finger and exo |
| L381W | closed conformation of finger and exo |
| L381H | closed conformation of finger and exo |
| K383N | closed conformation of finger and exo |
| K383A | closed conformation of finger and exo |
| L389A | closed conformation of finger and exo |
| L389W | closed conformation of finger and exo |
| L389H | closed conformation of finger and exo |
| F393A | closed conformation of finger and exo |
| F393W | closed conformation of finger and exo |
| F393H | closed conformation of finger and exo |
| I433A | closed conformation of finger and exo |
| I433W | closed conformation of finger and exo |
| I433H | closed conformation of finger and exo |
| K383L | phosphate backbone interaction |
| K383H | phosphate backbone interaction |
| K383R | phosphate backbone interaction |
| Q380R | phosphate backbone interaction |
| Q380H | phosphate backbone interaction |
| Q380K | phosphate backbone interaction |
| K371L | phosphate backbone interaction |
| K371H | phosphate backbone interaction |
| K371R | phosphate backbone interaction |
| K379L | phosphate backbone interaction |
| K379H | phosphate backbone interaction |
| K379R | phosphate backbone interaction |
| E486A | phosphate backbone interaction |
| E486D | phosphate backbone interaction |
| N387L | incoming nucleotide base and translocation |
| N387F | incoming nucleotide base and translocation |
| N387V | incoming nucleotide base and translocation |
| N251H | phosphate interaction |
| N251Q | phosphate interaction |
| N251D | phosphate interaction |
| N251E | phosphate interaction |
| N251K | phosphate interaction |
| N251R | phosphate interaction |
| A484K | phosphate interaction |
| A484R | phosphate interaction |
| K383Q | phosphate interaction |
| K383N | phosphate interaction |
| K383T | phosphate interaction |
| K383S | phosphate interaction |
| K383A | phosphate interaction |
| I179H/I378H | closed conformation |
| I179W/I378W | closed conformation |
| I179Y/I378Y | closed conformation |
| K478L | |
| I378Y | |
| I370A | |
| I179Y | |
| N387L/A484E | |
| N387L/A484Y | |
| T372Q/N387L/A484E | |
| T372Q/N387L/A484Y | |
| T372L/N387L/A484E | |
| T372L/N387L/K478Y/A484Y | |
| T372Y/N387L/K478Y/A484E | |
| T372Y/N387L/K478Y/A484Y | |

Table 3 presents exemplary Φ29 mutants that exhibit two slow step behavior under appropriate reaction conditions. The first three modified polymerases exhibit the most pronounced two slow step behavior, followed by the next six. As noted, the polymerases are optionally exonuclease-deficient; for example, they can also include an N62D substitution.

TABLE 3

A484E/E375Y/K512Y/T368F
A484Y/E375Y/K512Y/T368F
N387L/E375Y/K512Y/T368F
T372Q/E375Y/K512Y/T368F
T372L/E375Y/K512Y/T368F
T372Y/K478Y/E375Y/K512Y/T368F
I370W/E375Y/K512Y/T368F
F198W/E375Y/K512Y/T368F
L381A/E375Y/K512Y/T368F
E375Y/K512Y/T368F

Compositions, kits, and systems (e.g., sequencing systems) including the modified recombinant polymerases with decreased rate constants are features of the invention, as are methods employing the modified polymerases (e.g., methods of sequencing or making DNA). Methods for generating recombinant polymerases are also featured, as described in greater detail below, as are the resulting polymerases. Thus, one aspect provides a modified recombinant Φ29-type DNA polymerase comprising one or more mutations (e.g., amino acid substitutions or insertions) relative to a parental polymerase at one or more positions selected from the group consisting of: a) positions that form a binding site for a metal ion that interacts with an epsilon and/or digamma phosphate of a bound nucleotide analog having five or more phosphate groups; b) positions 372-397 and 507-514; c) positions that form a binding site for a terminal fluorophore on a phosphate-labeled nucleotide analog, particularly hexaphosphate analogs; d) positions at an intramolecular interface in a closed conformation of a ternary complex comprising the polymerase, a DNA, and a nucleotide or nucleotide analog; e) positions that form a binding site for a polyphosphate group of a bound nucleotide or nucleotide analog; f) positions that interact with the base of a bound nucleotide or nucleotide analog; and g) positions that interact with a bound DNA; wherein numbering of positions is relative to wild-type Φ29 polymerase. Preferably, the one or more mutations comprise at least one mutation other than a 514Y, 514W, 514F, 514I, 514K, 259S, 370V, 370K, 372D, 372E, 372R, 372K, 372N, 372L, 387A, 387D, 478D, 478E, 478R, 480K, 480M, 480R, 371Q, 379E, 379T, 486D, 486A, 188A, 188S, 254F, 254V, 254A, 390F, or 390A substitution. The modified polymerase optionally exhibits a decreased first rate constant, balanced first and second rate constants, and the like as for the embodiments described above.

A number of relevant positions and mutations are described herein. For example, the modified polymerase can comprise at least one amino acid substitution at at least one residue selected from the group consisting of positions 484, 249, 179, 198, 211, 255, 259, 360, 363, 365, 370, 372, 378, 381, 383, 387, 389, 393, 433, 478, 480, 514, 251, 371, 379, 380, 383, 458, 486, 101, 188, 189, 303, 313, 395, 414, 497, 500, 531, 532, 534, 558, 570, 572, 574, 64, 305, 392, 402, 422, 496, 529, 538, 555, 575, 254, and 390. Exemplary modified polymerases include those with at least one amino acid substitution or combination of substitutions selected from the group consisting of an amino acid substitution at position 484; an amino acid substitution at position 198; an amino acid substitution at position 381; A484E; A484Y; N387L; T372Q; T372Y; T372Y and K478Y; K478Y; I370W; F198W; L381A; T368F; A484E, E375Y, K512Y, and T368F; A484Y, E375Y, K512Y, and T368F; N387L, E375Y, K512Y, and T368F; T372Q, E375Y, K512Y, and T368F; T372L, E375Y, K512Y, and T368F; T372Y, K478Y, E375Y, K512Y, and T368F; I370W, E375Y, K512Y, and T368F; F198W, E375Y, K512Y, and T368F; L381A, E375Y, K512Y, and T368F; and E375Y, K512Y, and T368F, as well as others described herein. As another example, the modified polymerase can include an insertion of at least one amino acid (e.g., 1-7 amino acids, e.g., glycine) within residues 372-397 and/or 507-514 (e.g., after residue 374, 375, 511, and/or 512).

Polymerase Reaction Conditions

Recombinant polymerases of the invention are optionally modified in a manner in which the relative rates of steps of the polymerization reaction are changed, for example, such that the polymerase is capable of showing two slow step characteristics. The reaction conditions can also affect reaction rates. Reaction conditions can thus be manipulated, for example, to further slow a step or steps which are already slowed in a modified polymerase, or to slow an additional step, such that the resulting polymerase system exhibits two slow step behavior.

The polymerase reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance two slow step behavior of polymerases is described in detail in U.S. patent application Ser. No. 12/414,191 filed Mar. 30, 2009, and entitled "Two slow-step polymerase enzyme systems and methods."

Enzymatic reactions are often run in the presence of a buffer, which is used, in part, to control the pH of the reaction mixture. The type of buffer can in some cases influence the kinetics of the polymerase reaction in a way that can lead to two slow-step kinetics. For example, in some cases, use of TRIS as buffer is useful for obtaining a two slow-step reaction. Suitable buffers include, for example, TAPS (3-{[tris (hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl) methylglycine), HEPES 4-2-hydroxyethyl-1-piperazineethanesulfonic acid), TES (2-{[tris (hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some cases, the pH is between about 6.5 and about 8.0. In some cases, the pH is between about 6.5 and 7.5. In some cases, the pH is about 6.5, 6.6, 6.7, 6.8, 6.9, 7.0, 7.1, 7.2, 7.3, 7.4, or 7.5.

The temperature of the reaction can be adjusted in order to obtain a reaction exhibiting two slow-step kinetics. The reaction temperature may depend upon the type of polymerase which is employed. Temperatures between 15° C. and 90° C., between 20° C. and 50° C., between 20° C. and 40° C., or between 20° C. and 30° C. can be used.

In some cases, additives can be added to the reaction mixture that will influence the kinetics of the polymerase reaction in a manner that can lead to two slow-step kinetics. In some cases, the additives can interact with the active site of the enzyme, acting for example as competitive inhibitors. In some cases, additives can interact with portions of the enzyme away from the active site in a manner that will influence the kinetics of the reaction so as to produce a reaction exhibiting two slow steps. Additives that can influence the kinetics include, for example, competitive but otherwise unreactive substrates or inhibitors in analytical reactions to modulate the rate of reaction as described in copending U.S. Utility patent application Ser. No. 12/370,472, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps shown in FIG. 12. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

One aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interaction in polymerase reactions, see, e.g., Arndt, et al., Biochemistry (2001) 40:5368-5375.

For example, and without being bound to any particular theory of operation, it is understood that metal cofactor binding in and around the active site serves to stabilize binding of incoming nucleotides and is required for subsequent catalysis, e.g., as shown in steps 106 and 108 of FIG. 12. Other metal cofactor binding sites in polymerases, e.g., in the exonuclease domains, are understood to contribute to different functionality of the overall proteins, such as exonuclease activity. Modulation, and particularly competitive modulation, of divalent metal cofactors to the synthesis reaction can provide substantial benefits in terms of reaction kinetics without a consequent increase in negative reaction events.

In the synthesis reaction, certain divalent or trivalent metal cofactors, such as magnesium and manganese, are known to interact with the polymerase to modulate the progress of the reaction (See, e.g., U.S. Pat. No. 5,409,811). Other divalent metal ions, such as $Ca^{2+}$, have been shown to interact with the polymerase, such as Φ29 derived polymerases, to negative effect, e.g., to halt polymerization. As will be appreciated, depending upon the nature of the polymerization reaction, environmental conditions, the polymerase used, the nucleotides employed, etc., different metal co-factors will have widely varying catalytic effects upon the polymerization reaction. In the context of the present invention, different metal co-factors will be referred to herein based upon their relative catalytic impact on the polymerization reaction, as compared to a different metal included under the same reaction conditions. For purposes of discussion, a first metal cofactor that interacts with the polymerase complex to support the polymerization reaction to a higher level than a second metal co-factor under the same conditions is termed a "catalytic metal ion" or "catalytic metal." In preferred aspects, such catalytic metals support the continued, iterative or processive polymerization of nucleic acids under the particular polymerase reaction conditions, e.g., through the addition of multiple bases, while in some cases, a given type of metal cofactor may only support addition of a single base. Such metals may be sufficiently catalytic, depending upon the specific application.

In certain cases, particularly preferred divalent metal ions or catalytic metals include, e.g., $Mn^{2+}$, and in some cases will include $Mg^{2+}$. Less preferred multivalent metal ions that may provide a sufficient level of catalytic activity depending upon the desired application include, e.g., zinc.

For purposes of the invention, metal ions that interact with the polymerase but that do not promote the polymerization reaction, and in many cases act to arrest or prevent polymerization, are termed "non-catalytic metals." Included among the non-catalytic metals for various polymerase systems are calcium, barium, strontium, iron, cobalt, nickel, tin, zinc, and europium. For example, these metals can be added to the polymerization reaction in salt form such as $Sr(OAc)_2$, $Sr(OAc)_2$, $CoCl_2$, $SnCl_2$, $CaCl_2$, or $ZnSO_4$.

As described in detail in U.S. patent application Ser. No. 12/414,191 filed Mar. 30, 2009, and entitled "Two slow-step polymerase enzyme systems and methods," it has been discovered that mixtures of both catalytic and non-catalytic metal ions in the polymerization reaction mixture yields surprisingly beneficial results in this process. In particular, it has been observed that the competitive exchange rate for catalytic and non-catalytic metal ions in nucleic acid polymerases is sufficiently fast that one can exchange catalytic for non-catalytic ions in the reaction complex. Thus, these exchangeable catalytic and non-catalytic cofactors can be contacted with the polymerase complex to first sequester the nucleotide in a non-exchangeable state within the polymerase complex, from which it is substantially less likely to be released. Upon exchange of a non-catalytic cofactor with a catalytic co-factor, the nucleotide will be transitioned into an exchangeable state within the complex, from which it can proceed through an incorporation reaction. Further, the rate of the exchange is such that one can effectively modulate the speed of the polymerase reaction by modulating the relative proportion of catalytic/non-catalytic metal ions in the reaction mixture. In particular, modulating the relative concentrations of these ions effectively modulates the reaction kinetics of individual enzymes, rather than just in bulk. Furthermore, because the nature of the interaction of the complex with calcium ions interferes with both the forward progress of incorporation and the reverse progress of release or branching, one can effectively slow the reaction, or more specifically, increase the time the "to be incorporated" nucleotide is bound, without a consequent increase in the amount of nucleotide released or branching.

Thus, exemplary additives that can enhance control of kinetic behavior include non-catalytic metal ions, generally provided in a mixture of catalytic and non-catalytic metal ions. The molar ratio of catalytic to non-catalytic metals in the reaction mixture will generally vary depending upon the type of kinetic modulation desired for a given synthesis reaction, where slower incorporation would suggest higher levels of non-catalytic metal ions. Typically, such ratios of catalytic to non-catalytic metals in the reaction mixture will vary from about 10:1 to about 1:10, and preferably, from about 10:1 to about 1:5 (e.g., from about 5:1 to about 1:1 or about 2.5:1 to about 1.5:1), depending upon the desired level of modulation, the particular enzyme system employed, the catalytic and non-catalytic metal cofactors that are used, and the reaction conditions.

In addition to the presence of such metals at the ratios described herein, the absolute concentration of such metals in the reaction mixtures will typically range from about 0.1 mM to about 10 mM. For example, the reaction can include from about 0.25 mM $MnCl_2$ to about 1 mM $MnCl_2$ and from about 0.1 mM $CaCl_2$ to about 1.5 mM $CaCl_2$.

Modifying DNA Polymerases to Decrease Branching Fraction, Increase Closed Complex Stability, and Alter Reaction Rates Structure-Based Design of Recombinant Polymerases Structural data for a polymerase can be used to conveniently identify amino acid residues as candidates for mutagenesis to create recombinant polymerases, for example, having modified domain interfaces to improve complex stability and/or modified active site regions that reduce branching and/or reaction rates. For example, analysis of the three-dimensional structure of a polymerase such as Φ29 can identify residues that are in the active polymerization site of the enzyme, residues that form part of the nucleotide analog binding pocket, and/or amino acids at an interface between domains.

The three-dimensional structures of a large number of DNA polymerases have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb(dot)org/pdb. Structures, along with domain and homology information, are also freely available for search and download from the National Center for Biotechnology Information's Molecular Modeling Data-Base, at www(dot)ncbi(dot)nlm(dot)nih(dot)gov/Structure/

MMDB/mmdb(dot)shtml. The structures of Φ29 polymerase, Φ29 polymerase complexed with terminal protein, and Φ29 polymerase complexed with primer-template DNA in the presence and absence of a nucleoside triphosphate are available; see Kamtekar et al. (2004) "Insights into strand displacement and processivity from the crystal structure of the protein-primed DNA polymerase of bacteriophage Φ29" Mol. Cell 16(4): 609-618), see Kamtekar et al. (2006) "The phi29 DNA polymerase:protein-primer structure suggests a model for the initiation to elongation transition" EMBO J. 25(6):1335-43, and Berman et al. (2007) "Structures of phi29 DNA polymerase complexed with substrate: The mechanism of translocation in B-family polymerases" EMBO J. 26:3494-3505, respectively. The structures of additional polymerases or complexes can be modeled, for example, based on homology of the polymerases with polymerases whose structures have already been determined. Alternatively, the structure of a given polymerase (e.g., a wild-type or modified polymerase), optionally complexed with a DNA (e.g., template and/or primer) and/or nucleotide analog, or the like, can be determined.

Techniques for crystal structure determination are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide, 2nd Edition* Wiley Publishers, New York; Ladd and Palmer (1993) *Structure determination by X-ray crystallography, 3rd Edition* Plenum Press, New York; Blundell and Johnson (1976) *Protein Crystallography* Academic Press, New York; Glusker and Trueblood (1985) *Crystal structure analysis: A primer, 2nd Ed*. Oxford University Press, New York; *International Tables for Crystallography, Vol. F. Crystallography of Biological Macromolecules*; McPherson (2002) *Introduction to Macromolecular Crystallography* Wiley-Liss; McRee and David (1999) *Practical Protein Crystallography, Second Edition* Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing, Volume 5* IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" Acta Cryst. D56:232-237; Dauter (2002) "New approaches to high-throughput phasing" Curr. Opin. Structural Biol. 12:674-678; Chen et al. (1991) "Crystal structure of a bovine neurophysin-II dipeptide complex at 2.8 Å determined from the single-wavelength anomalous scattering signal of an incorporated iodine atom" Proc. Natl Acad. Sci. USA, 88:4240-4244; and Gavira et al. (2002) "Ab initio crystallographic structure determination of insulin from protein to electron density without crystal handling" Acta Cryst.D58:1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" Methods in Enzymology 276: 307-326), the CCP4 package (Collaborative Computational Project (1994) "The CCP4 suite: programs for protein crystallography" Acta Crystallogr D 50:760-763), SOLVE and RESOLVE (Terwilliger and Berendzen (1999) Acta Crystallogr D 55 (Pt 4):849-861), SHELXS and SHELXD (Schneider and Sheldrick (2002) "Substructure solution with SHELXD" Acta Crystallogr D Biol Crystallogr 58:1772-1779), Refmac5 (Murshudov et al. (1997) "Refinement of Macromolecular Structures by the Maximum-Likelihood Method" Acta Crystallogr D 53:240-255), PRODRG (van Aalten et al. (1996) "PRODRG, a program for generating molecular topologies and unique molecular descriptors from coordinates of small molecules" J Comput Aided Mol Des 10:255-262), and O (Jones et al. (1991) "Improved methods for building protein models in electron density maps and the location of errors in these models" Acta Crystallogr A 47 (Pt 2):110-119).

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis*, 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) Curr. Opin. Struct. Biol. 10:585; Gardner (1998) Annu. Rev. Biophys. Biomol. Struct. 27:357; Wüthrich (2003) Angew. Chem. Int. Ed. 42:3340; Bax (1994) Curr. Opin. Struct. Biol. 4:738; Pervushin et al. (1997) Proc. Natl. Acad. Sci. U.S.A. 94:12366; Fiaux et al. (2002) Nature 418: 207; Fernandez and Wider (2003) Curr. Opin. Struct. Biol. 13:570; Ellman et al. (1992) J. Am. Chem. Soc. 114:7959; Wider (2000) BioTechniques 29:1278-1294; Pellecchia et al. (2002) Nature Rev. Drug Discov. (2002) 1:211-219; Arora and Tamm (2001) Curr. Opin. Struct. Biol. 11:540-547; Flaux et al. (2002) Nature 418:207-211; Pellecchia et al. (2001) J. Am. Chem. Soc. 123:4633-4634; and Pervushin et al. (1997) Proc. Natl. Acad. Sci. USA 94:12366-12371.

The structure of a polymerase, or polymerase bound to a DNA or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide bound. The active site or other relevant domain of the polymerase can be identified, for example, by homology with other polymerases, examination of polymerase-template or polymerase-nucleotide co-complexes, biochemical analysis of mutant polymerases, and/or the like. The position of a nucleotide analog (as opposed to an available nucleotide structure) in the active site can be modeled, for example, by projecting the location of non-natural features of the analog (e.g., additional phosphate or phosphonate groups in the phosphorus containing chain linked to the nucleotide, e.g., tetra, penta or hexa phosphate groups, detectable labeling groups, e.g., fluorescent dyes, or the like) based on the previously determined location of another nucleotide or nucleotide analog in the active site.

Such modeling of the nucleotide analog or template (or both) in the active site can involve simple visual inspection of a model of the polymerase, for example, using molecular graphics software such as the PyMOL viewer (open source, freely available on the World Wide Web at www(dot)pymol (dot)org), Insight II, or Discovery Studio 2.1 (commercially available from Accelrys at (www (dot) accelrys (dot) com/ products/discovery-studio). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" Drug Discov. Today 7:1047-1055; Molecular Modeling for Beginners, at (www (dot) usm (dot) maine (dot) edu/~rhodes/SPVTut/index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) corn), the Discover simulation package (included in Insight II, supra), and Dynama (available at (www(dot) cs (dot) gsu (dot) edu/~cscrwh/progs/progs (dot) html). See also an extensive list of modeling software at (www (dot) netsci (dot) org/ Resources/Software/Modeling/MMMD/top (dot) html.

Visual inspection and/or computational analysis of a polymerase model, including optional comparison of models of the polymerase in different states, can identify relevant features of the polymerase, including, for example, residues that can be mutated to stabilize the closed complex of the polymerase, to decrease branching, and to alter rate constants. Such residues can include, for example, amino acid residues of domains that are in close proximity to one another (to stabilize inter-domain interactions), residues in an active site or binding pocket that interact with a nucleotide or analog, DNA, or product, residues that modulate how large a binding pocket for an analog is relative to the analog, etc.

Thus, in addition to methods of using the polymerases and other compositions herein, the present invention also includes methods of making the polymerases. (Polymerases made by the methods are also a feature of the invention.) As described, methods of making a recombinant DNA polymerase can include structurally modeling a parental polymerase, e.g., using any available crystal structure and molecular modeling software or system. Based on the modeling, one or more amino acid residue positions in the polymerase are identified as targets for mutation. For example, one or more feature affecting closed complex stability, nucleotide access to or removal from the active site (and, thereby, branching), binding of a DNA or nucleotide analog, product binding, etc. is identified. These residues can be, e.g., in the active site or a binding pocket or in a domain such as the exonuclease, TPR2 or thumb domain (or interface between domains) or proximal to such domains. The DNA polymerase is mutated to include different residues at such positions (e.g., another one of the nineteen other commonly occurring natural amino acids or a non-natural amino acid, e.g., a nonpolar and/or aliphatic residue, a polar uncharged residue, an aromatic residue, a positively charged residue, or a negatively charged residue), and then screened for an activity of interest (e.g., processivity, $k_{off}$, $K_d$, branching fraction, decreased rate constant, balanced rate constants, etc.). It will be evident that catalytic and/or highly conserved residues are typically (but not necessarily) less preferred targets for mutation.

As one example, as noted above inspection of a closed Φ29-DNA complex reveals an important interface formed by the exonuclease, TPR2 and thumb domains, e.g., positions 68 to 76 and position 92 (exonuclease), positions 405 to 413 (TPR2), and positions 560 to 564 (thumb) (all numbered relative to wild-type Φ29). Mutations that stabilize this interface can increase stability of the closed complex and thus increase processivity. The parental polymerase can be mutated to introduce an interaction predicted to stabilize the closed complex. For example, one more residues that are in close proximity to each other in the closed complex can be replaced with residues having complementary features, for example, oppositely charged residues (e.g., aspartic or glutamic acid, and lysine, arginine, or histidine), residues that can hydrogen bond with each other (e.g., serine, threonine, histidine, asparagine, or glutamine), hydrophobic residues that can interact with each other, aromatic residues that can engage in π-π or edge-face stacking interactions, residues that can engage in cation-π interactions, or the like. As noted, a residue can be replaced with another naturally occurring amino acid (e.g., a nonpolar and/or aliphatic residue, a polar uncharged residue, an aromatic residue, a positively charged residue, or a negatively charged residue) or with a non-natural amino acid (e.g., having a chemical group that would interact with group(s) in the polymerase). Similarly, the parental polymerase can be mutated to remove an interaction predicted to destabilize the closed complex (two positively charged or two negatively charged residues in close proximity, residues with unfavorable van der Waals interactions, etc.).

In another example, branching fraction for a nucleotide or nucleotide analog can be decreased, for example, by more tightly structuring the binding pocket for the nucleotide or analog. Residues limiting access of the nucleotide or analog to the binding pocket can be altered to decrease steric inhibition, or residues can be modified to introduce favorable interactions with complementary features of the analog.

The size or composition (e.g., position of charged or hydrophobic residues) of the binding pocket in the active site can control entry and release of the nucleotide or analog, which can affect branching fraction. A residue can, for example, be deleted or replaced with a residue having a different (smaller, larger, ionic, non-ionic, etc.) side chain. Similarly, residues that can be altered to introduce desirable interactions with the nucleotide analog can be identified to reduce branching. Such a residue can be replaced with a residue that is complementary with, e.g., a non-natural feature of the analog, for example, with a residue that can hydrogen bond to the analog (e.g., serine, threonine, histidine, asparagine, or glutamine), a hydrophobic residue that can interact with a hydrophobic group on the analog, an aromatic residue that can provide favorable hydrophobic interactions with a group on the analog (e.g., a fluorophore), an aromatic residue that can engage in a π-π or edge-face stacking interaction with an aromatic group in the analog (e.g., a base or fluorophore), a residue that can engage in a cation-π interaction with the analog, or a charged residue (e.g., aspartic or glutamic acid, or lysine, arginine, or histidine) that can electrostatically interact with an oppositely charged moiety on the analog (e.g., an additional phosphate group). Interactions with other non-natural features of analogs (e.g., a linker, e.g., between the terminal phosphate and a dye) can also be introduced. As noted, a residue can be replaced with another naturally occurring amino acid (e.g., a nonpolar and/or aliphatic residue, a polar uncharged residue, an aromatic residue, a positively charged residue, or a negatively charged residue) or with a non-natural amino acid (e.g., having a chemical group that would interact with group(s) in the analog). As just one specific example of such structure-based design of polymerases with decreased branching fraction, inspection of a model of the Φ29 polymerase reveals that a modified recombinant polymerase comprising E375Y and K512Y substitutions can exhibit an improved branching fraction phenotype. The amino acid residues 375 and 512 are located in positions predicted to bracket the exit position of the nucleotide analogs, and the aromatic rings of the tyrosines in the aforementioned modified recombinant polymerase can interact favorably with the aromatic groups of the analogs.

As another example, the parental polymerase can be mutated to decrease at least one elemental reaction rate, to produce a modified polymerase having a rate constant less than that of the parental polymerase. Several exemplary strategies follow.

Figure 4:
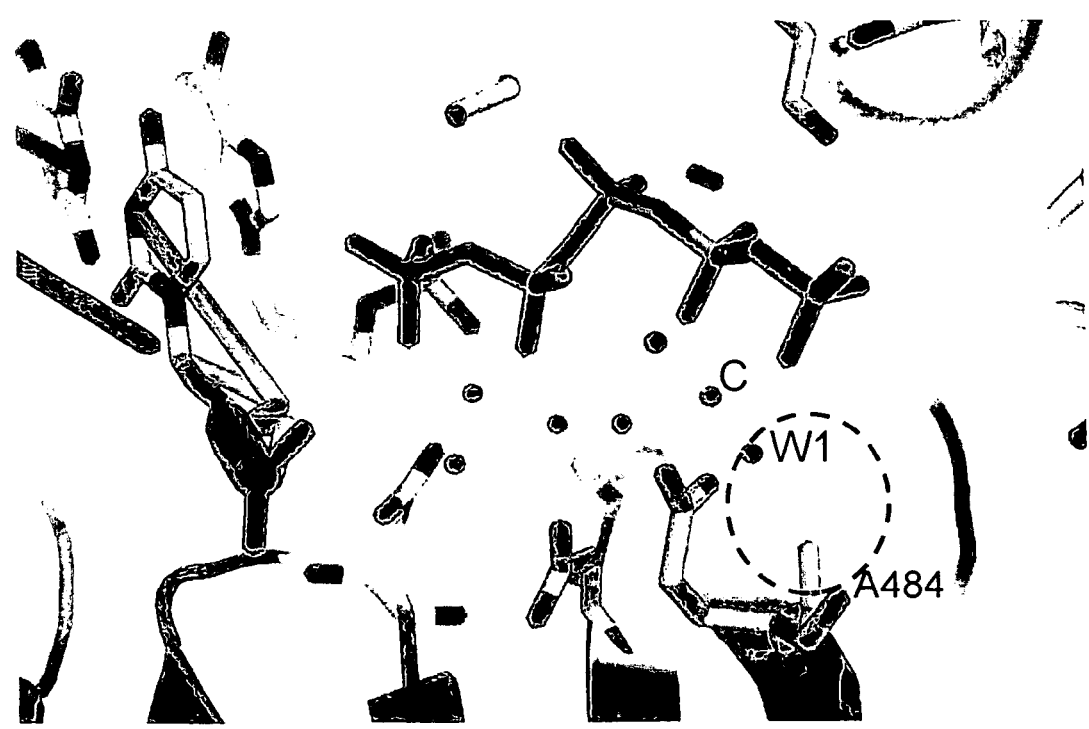
FIG. 4 illustrates a novel metal binding site observed in a crystal structure of D12A/D66A/T368F/E375Y/K512Y Φ29 polymerase complexed with hexaphosphate analog A555dG6P. The novel metal is labeled C.

Examination of a crystal structure of a D12A/D66A/T368F/E375Y/K512Y Φ29 polymerase complexed with analog A555dG6P revealed a new metal binding site that is formed by the fifth (epsilon) and sixth (digamma) phosphates of the analog, residue Glu469, and three fixed water molecules (FIG. 4). Metal binding to the enzyme and analog can be strengthened by replacing the water molecules by either manipulation of the analog phosphate backbone or the polymerase side chains, e.g., by mutation of nearby residues A484 and/or D249, e.g., by site-saturated mutagenesis. Mutations that replace A484 and/or D249 with a larger side chain are of particular interest, such that the mutated residue(s) can replace one or more water molecules and chelate the metal ion with the fifth and sixth phosphates, slowing release of cleaved products. Exemplary mutations include A484E, A484Y, A484H, A484D, D249E, D249Y, D249H, and combinations thereof (e.g., D249E with one of the mutations at position 484).

Another strategy for slowing reaction rates involves stabilizing a closed conformation of a ternary complex comprising the polymerase, a DNA, and a nucleotide or nucleotide analog, for example, to slow release of the analog. The parental polymerase can be mutated at one or more positions to introduce at least one intramolecular interaction predicted to stabilize the closed conformation of the ternary complex or to remove at least one intramolecular interaction predicted to destabilize the closed conformation. For example, one or more residues that are in close proximity to each other in the closed conformation of the ternary complex can be replaced with residues having complementary features, for example, oppositely charged residues (e.g., aspartic or glutamic acid, and lysine, arginine, or histidine), residues that can hydrogen bond with each other (e.g., serine, threonine, histidine, asparagine, or glutamine), hydrophobic residues that can interact with each other, aromatic residues that can engage in π-π or edge-face stacking interactions, residues that can engage in cation-π interactions, or the like, e.g., to stabilize the closed conformation of the fingers, the finger-exonuclease domain interface, finger-palm interactions, etc., including natural and non-natural residues as noted herein. Residues identified as targets for stabilizing the closed conformation include, e.g., 179, 198, 211, 255, 259, 360, 363, 365, 370, 372, 378, 381, 383, 387, 389, 393, 433, 478, and 480. Exemplary substitutions include 179Y, 179H, 179A, 179W, 198W, 198A, 198H, 211W, 211A, 211H, 255W, 255A, 255H, 259W, 259A, 259H, 360W, 360A, 360H, 363W, 363A, 363H, 365N, 365Q, 370W, 370A, 370H, 372Q, 372L, 372Y, 372H, 372V, 372I, 372F, 372N, 378A, 378H, 378W, 378Y, 381A, 381H, 381W, 383N, 383A, 383L, 383H, 383R, 387L, 387F, 387V, 389A, 389W, 389H, 393A, 393W, 393H, 433A, 433W, 433H, 478Y, 478L, 480H, and 480F, as well as combinations thereof such as T372L/K478Y, T372Y/K478Y, T372Y/K478L, I179A/L381A, I179A/I378A/L381A, I370A/I378A, I179A/I370A/I378A/L381A, I179H/I378H, I179W/I378W, and I179Y/I378Y. As for other embodiments herein, site-saturated mutagenesis to all possible residues can also be performed.

Increasing interaction between the polymerase and the base of an incoming nucleotide or nucleotide analog can also slow a reaction step, e.g., translocation. Residue 387 can be mutated to a hydrophobic or aromatic residue to increase hydrophobic interactions with the base and/or stack with it. Exemplary mutations include N387L, N387F, and N387V. Site-saturated mutagenesis to all possible residues can also be performed.

Similarly, the polymerase can be mutated to increase interaction between the polymerase and a label on a nucleotide analog, e.g., a terminal fluorophore. As for the embodiments above, one or more residues can be mutated to introduce a favorable interaction between the polymerase and the label or to remove an unfavorable interaction. As one example, residue 514 can be mutated to another hydrophobic residue or to an aromatic residue to improve interaction with a terminal fluorophore, particularly on a hexaphosphate analog. Exemplary mutations include V514Y and V514F. As another example, the flexibility of either or both of two surface loops on the polymerase, residues 372-397 and 507-514, can be increased by insertion of one or more amino acid residues (e.g., 1-7 residues, e.g., glycine) within either or both loops to facilitate interaction of other regions with the analog (e.g., of residue 512 with a terminal fluorophore, in a mutant polymerase that also includes K512Y). For example, a glycine residue can be introduced after residue 374, 375, 511, and/or 512 (designated as 374.1G, 375.1G, etc.).

For single molecule sequencing with phosphate-labeled analogs, the timing of polyphosphate release after nucleotidyl transfer can play an important role in detection of the event, as described above. The release of pyrophosphate is coupled with the movement of the DNA polymerase and DNA translocation (Steitz (2004) "The structural basis of the transition from initiation to elongation phases of transcription, as well as translocation and strand separation, by T7 RNA polymerase" Curr Opin Struct Biol 14(1):4-9, Steitz (2006) "Visualizing polynucleotide polymerase machines at work" EMBO J 25(15):3458-68, and Steitz and Yin (2004) "Accuracy, lesion bypass, strand displacement and translocation by DNA polymerases" Philos Trans R Soc Lond B Biol Sci 359(1441):17-23). Where translocation follows polyphosphate release, slowing translocation will increase interpulse distance and decrease the chance of merging two consecutive pulses in SMS as described herein. Where polyphosphate release is concurrent with translocation, slowing translocation will not change interpulse distance but rather pulse width, which can improve detection of pulses as described herein.

Figure 7:
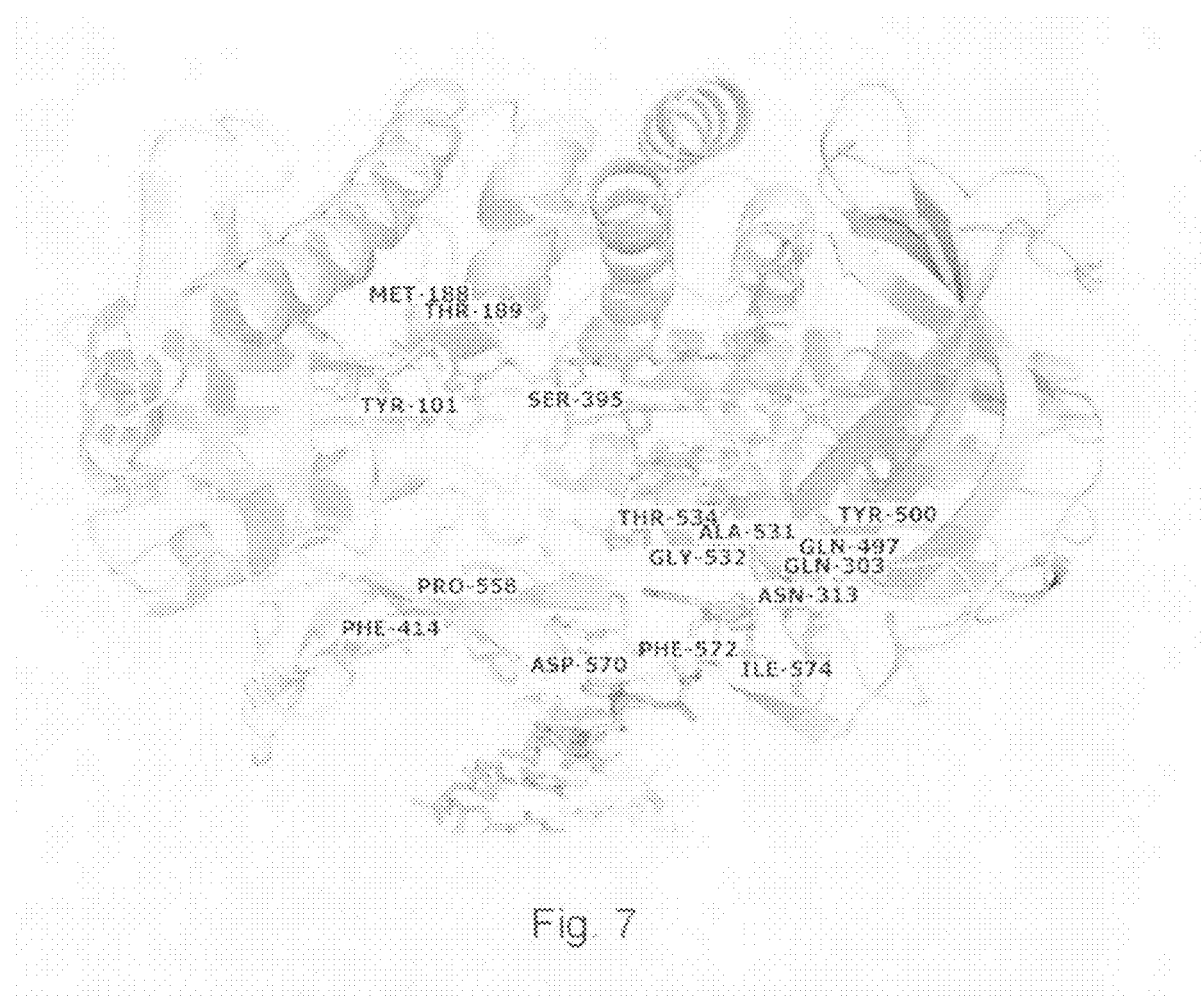
FIG. 7 presents the structure of Φ29 polymerase in complex with DNA and a nucleotide analog, showing the non-positively charged residues in group one. These residues are within 4 Å of the DNA.
Figure 8:
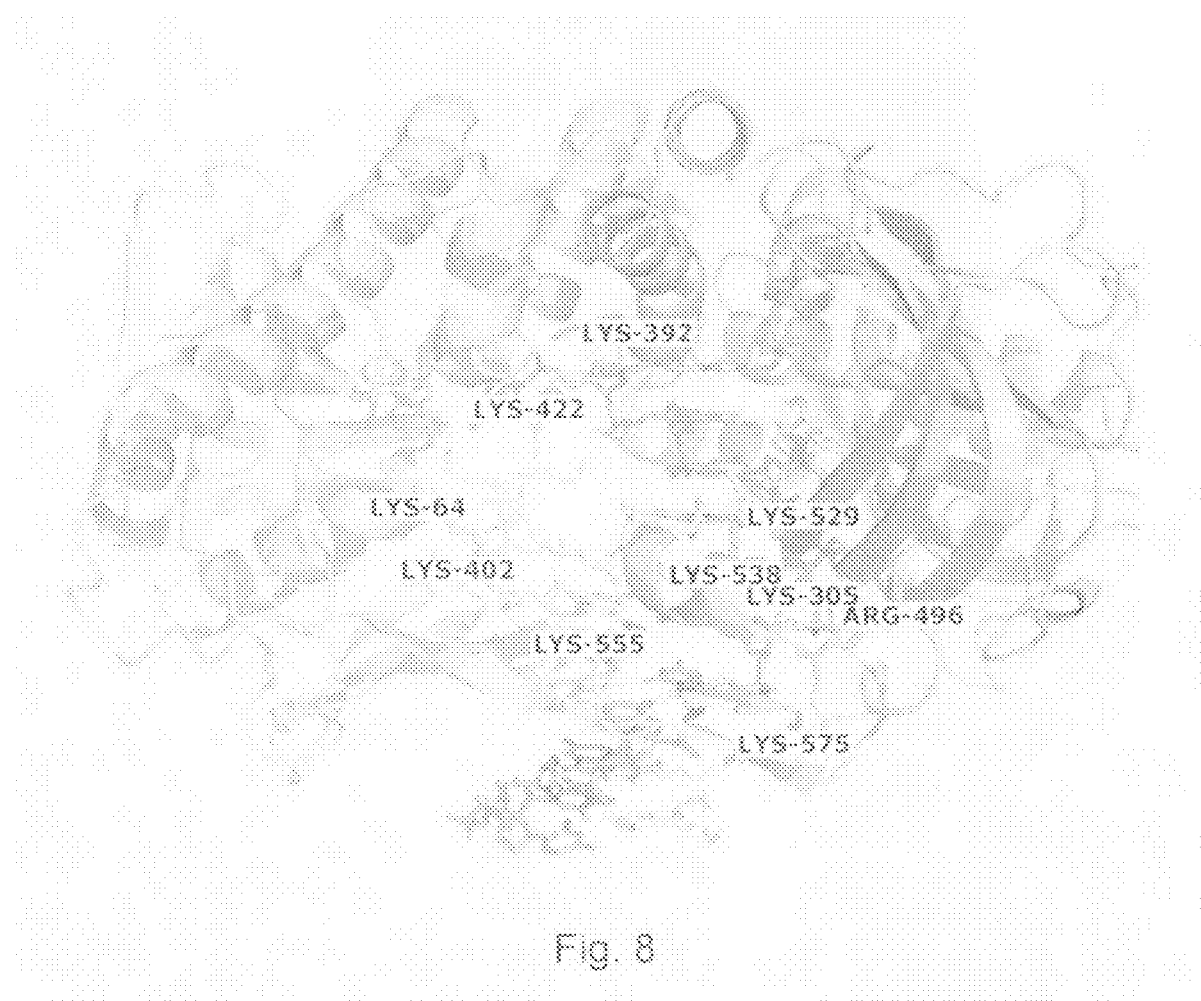
FIG. 8 presents the structure of Φ29 polymerase in complex with DNA and a nucleotide analog, showing the positively charged residues in group two. These residues are within 4 Å of the DNA and directly or indirectly interact with the DNA backbone.

Examination of an in-house crystal structure of Φ29 polymerase revealed two groups of residues within 4 Å of the DNA backbone and directly or indirectly interacting with the DNA. Residues in group one have non-positive charge: Y101, M188, T189, Q303, N313, S395, F414, Q497, Y500, A531, G532, T534, P558, D570, F572, and I574 (FIG. 7). Residues in group two have positive charge: K64, K305, K392, K402, K422, R496, K529, K538, K555, and K575 (FIG. 8). These two groups of residues exclude residues close to the enzyme's incoming deoxynucleotide binding site (active site).

Figure 9A:
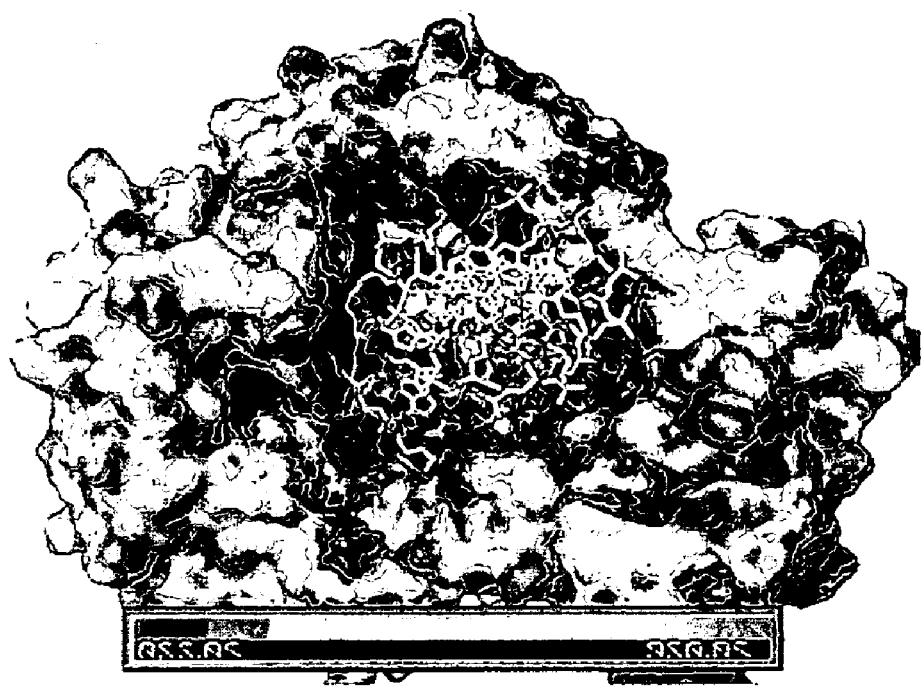
FIG. 9 Panels A and B depict the electrostatic surface of Φ29 polymerase in contact with the DNA. Positive charge is dark gray and negative charge is light gray; the intensity of the color represents the strength of the charge. The wild type of group one residues and the lysine mutants of group one residues are colored in the same scale in Panels A and B, respectively. The DNA binding interface is mainly positively charged. The positive charge on the DNA binding interface is significantly increased after the mutation of group one residues to lysine.
Figure 9B:
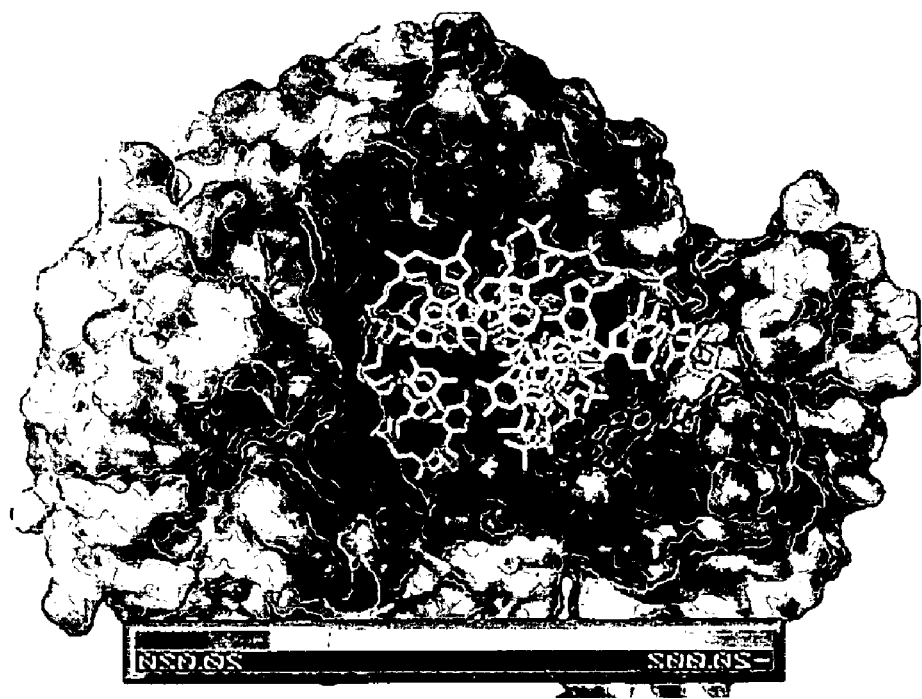
Figure 10A:
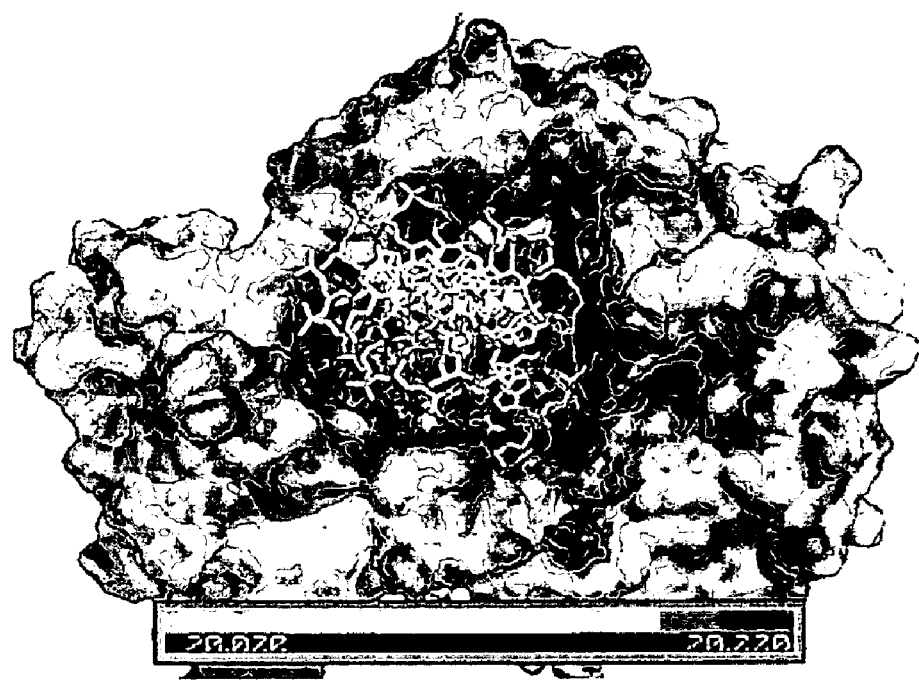
FIG. 10 Panels A and B depict the electrostatic surface of Φ29 polymerase in contact with the DNA. Positive charge is dark gray and negative charge is light gray; the intensity of the color represents the strength of the charge. The wild type of positively charged group two residues and the alanine mutants of group one residues are colored in the same scale in Panels A and B, respectively. The DNA binding interface is mainly positively charged. The positive charge on the DNA binding interface is significantly decreased after the mutation of group two residues to alanine.
Figure 10B:
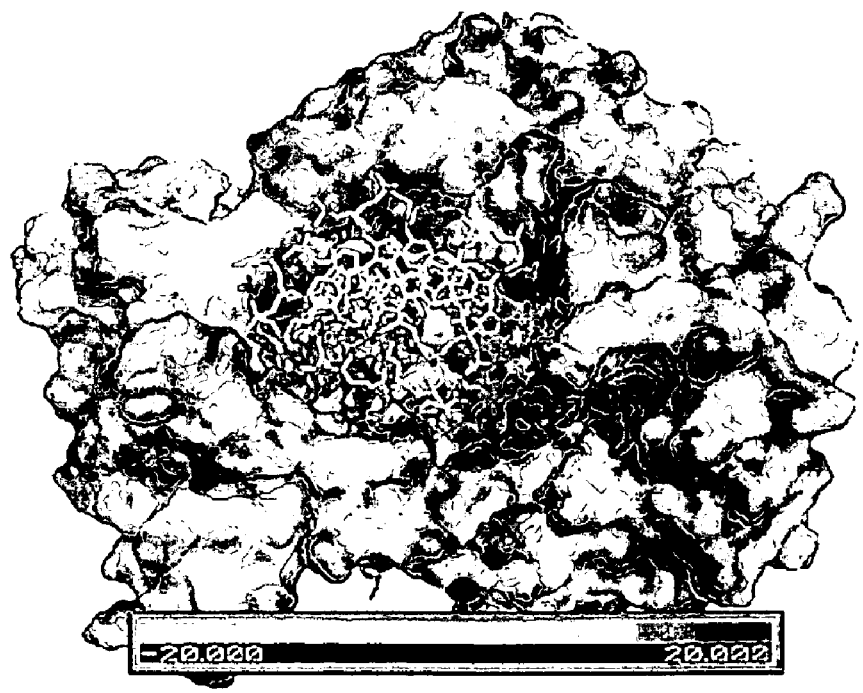

Residues from either or both groups can be mutated to strengthen or weaken interactions with the DNA and thus affect translocation and/or polyphosphate release. Typically, positively charged residues are favored for DNA binding due to the negatively charged DNA backbone. Thus, one or more residue from group one can be mutated to a positively charged residue, e.g., lysine, arginine, or histidine, to increase interaction. (Site-saturated mutagenesis to all possible residues can also be performed.) As for other strategies herein, promising mutations can be combined for greater enhancement of effect on rate. Since the residues of group ones are spread out in the region along the DNA backbone (except for the active site), mutation effect is generally addable. Virtual mutation of all residues in group one to positively charged lysine shows a significant enhancement of electrostatic interactions between the polymerase and the DNA (FIG. 9 Panels A and B). Similarly, one or more residues from group two can be mutated, e.g., to any of the other amino acids, e.g., by site-saturated mutagenesis. Virtual mutation of all residues in group two to uncharged alanine shows a significant decrease in electrostatic interactions between the polymerase and DNA (FIG. 10 Panels A and B). The mutation effect for group two is also generally addable. Combinations of mutations from groups one and two are also evaluated. Residues around the active site can also control translocation, for example, tyrosines 254 and 390 and asparagine 387. Mutation of these residues can also alter DNA translocation.

As another strategy, one or more residues in the polymerase that are proximal to a phosphate on a bound nucleotide or nucleotide analog can be mutated to weaken or strengthen interaction with the phosphate (e.g., any phosphate in a tri-, tetra-, penta-, hexa-, or hepta-phosphate analog). For example, a positively charged residue that interacts with a phosphate can be mutated to an uncharged or even a negatively charged residue to weaken interactions with the phosphate, or an uncharged or negatively charged residue can be mutated to a polar uncharged residue or a positively charged residue to strengthen interaction. Such mutations can, e.g., affect release of a polyphosphate product (e.g., pyrophosphate or a longer polyphosphate, e.g., with attached label).

Mutation of residues proximal to the polyphosphate tail of a bound nucleotide or analog can affect isomerization of the polyphosphate tail, slowing nucleotide isomerization and/or polyphosphate product release. This strategy can be particularly useful for nucleotide analogs with four or more phosphate groups. During the process of DNA polymerization, a nucleotide isomerization step before the chemical reaction step has been observed and considered to be a relatively slow step compared to the initial nucleotide binding event (Dahlberg and Benkovic (1991) "Kinetic mechanism of DNA polymerase I (Klenow fragment): Identification of a second conformational change and evaluation of the internal equilibrium constant" Biochemistry 30(20):4835-43, Patel et al. (1991) "Pre-steady-state kinetic analysis of processive DNA replication including complete characterization of an exonuclease-deficient mutant" Biochemistry 30(2):511-25, Hsieh et al. (1993) "Kinetic mechanism of the DNA-dependent DNA polymerase activity of human immunodeficiency virus reverse transcriptase" J. Biol. Chem 268(33):24607-13, Washington et al. (2001) "Yeast DNA polymerase eta utilizes an induced-fit mechanism of nucleotide incorporation" Cell 107(7):917-27, and Anand and Patel (2006) "Transient state kinetics of transcription elongation by T7 RNA polymerase" J. Biol. Chem 281(47):35677-85).

Figure 5A:
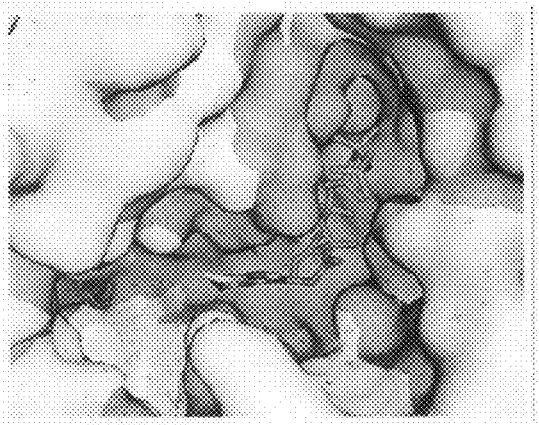
FIG. 5 illustrates the structure of a Φ29 polymerase ternary complex with the polyphosphate tail of the nucleotide analog in the active conformation with tight binding (Panel A) and in the inactive conformation with loose binding (Panel B).
Figure 5B:
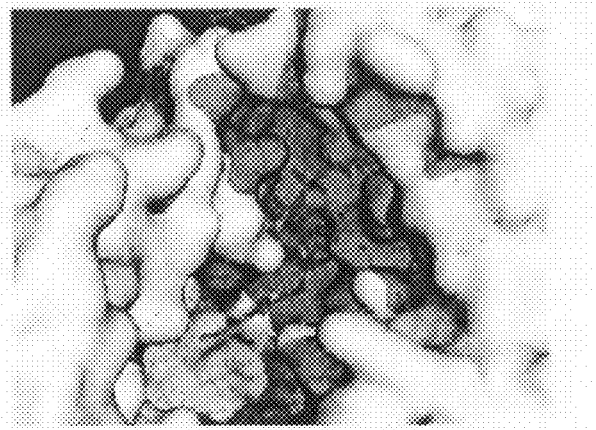

A group of DNA polymerase ternary complexes with the nucleoside polyphosphate tail in different conformations were determined by x-ray crystallography (Vaisman et al. (2005) "Fidelity of Dpo4: Effect of metal ions, nucleotide selection and pyrophosphorolysis" EMBO J 24(17):2957-67, and in-house crystal structures of Φ29 complexes). Crystal structures of Φ29 polymerase with a hexaphosphate analog determined in house reveal both active (FIG. 5 Panel A) and inactive (FIG. 5 Panel B) conformations of the polyphosphate tail on the incoming nucleotide analog. Comparison of the two ternary structures revealed that binding of the nucleotide analog is tighter in the active conformation than in the inactive conformation (FIG. 5 Panels A and B). The loose binding of the inactive hexaphosphate tail provides necessary space for sampling multiple inactive conformations and finally achieving the active conformation which leads to the chemical reaction. Increasing the multiplicity of the inactive conformations or stabilizing a certain inactive conformation can extend the isomerization time of the analog before the chemical reaction occurs. Mutants that do so without increasing branching fraction are preferred.

Figure 6:
FIG. 6 shows a superimposition of the structure of the polymerase ternary complex with the active polyphosphate conformation and the structure with the inactive polyphosphate conformation. The polymerase surface with the inactive polyphosphate conformation is shown. Two residues (Lys383 and Asp458) which act as a "clamp" (possible steric hindrance) between the active and inactive conformations are labeled.

Superposition of the active and inactive conformation structures revealed two residues, Lys383 and Asp458, on the two sides of the beta phosphate that provide limitation between the active and inactive conformational change. These two residues act as a "clamp" which introduces possible steric hindrance for the polyphosphate isomerization (FIG. 6). Decreasing the residue size at either or both of these two positions (especially position 383) can decrease the branching fraction. Mutating these residues can also increase the multiplicity of the inactive conformation, extending the isomerization time. Two other residues, Lys371 and Lys379, also interact with the polyphosphate tail. Mutation of these residues (e.g., to another positively charged residue or an uncharged residue) can also affect isomerization control. Note that Asp458 is in the polymerase active site, and mutating this residue may thus have undesirable effects on enzyme activity. The other three lysines provide a positively charged binding environment for the negatively charged polyphosphate tail. Severely changing the polarity of this binding pocket may disrupt accommodation of the analog, so mutation to other positively charged residues or to uncharged residues is typically preferred.

Residues that can be mutated to affect interactions with phosphates include, e.g., 251, 371, 379, 380, 383, 458, 484, and 486. Exemplary substitutions include 251E, 251K, 251R, 251H, 251Q, 251D, 371A, 371W, 371L, 371H, 371R, 371N, 371Q, 379L, 379H, 379R, 379N, 379Q, 380R, 380H, 380K, 383L, 383H, 383R, 383Q, 383N, 383T, 383S, 383A, 484K, 484R, 486A, and 486D. Site saturated mutagenesis, in which each of the other nineteen amino acids is substituted for the residue occupying a given position can also be performed at one or more of these positions, e.g., 383 or the others listed (and/or at essentially any of the positions noted elsewhere herein).

In a related strategy, the polymerase can be modeled with a polyphosphate in the binding pocket, e.g., through crystallographic study or molecular modeling. The polymerase can be mutated to alter isomerization of the polyphosphate product and thus slow its release. The length and/or chemical structure of the tail can also be modified to alter isomerization. Altering isomerization of the polyphosphate product can avoid inadvertently increasing branching fraction.

Mutating Polymerases

Various types of mutagenesis are optionally used in the present invention, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., decreased branch fraction, increased complex stability, improved processivity, decreased rate constant, and/or improved $k_{off}$, $K_m$, $V_{max}$, $k_{cat}$ etc., e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in WO 2007/076057 POLYMERASES FOR NUCLEOTIDE ANALOGUE INCORPORATION by Hanzel et al.; WO 2008/051530 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057 PROTEIN ENGINEERING STRATEGIES TO OPTIMIZE ACTIVITY OF SURFACE ATTACHED PROTEINS.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., *Molecular Cloning-A Laboratory Manual* (3rd Ed.), Vol. 1-3, Cold Spring Harbor Laboratory, Cold Spring Harbor, New York, 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel")) and *PCR Protocols A Guide to Methods and Applications* (Innis et al. eds) Academic Press Inc. San Diego, Calif. (1990) (Innis). The following publications and references cited within provide additional detail on mutation formats: Arnold, *Protein engineering for unusual environments*, Current Opinion in Biotechnology 4:450-455 (1993); Bass et al., *Mutant Trp repressors with new DNA-binding specificities*, Science 242:240-245 (1988); Bordo and Argos (1991) *Suggestions for "safe Residue Substitutions in Site-directed Mutagenesis* 217:721-729; Botstein & Shortle, *Strategies and applications of in vitro mutagenesis*, Science 229:1193-1201(1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Hayes (2002) *Combining Computational and Experimental Screening for rapid Optimization of Protein Properties* PNAS 99(25) 15926-15931; Kunkel, *The efficiency of oligonucleotide directed mutagenesis*, in Nucleic Acids & Molecular Biology (Eckstein, F. and Lilley, D. M. J. eds., Springer Verlag, Berlin)) (1987); Kunkel, *Rapid and efficient site-specific mutagenesis without phenotypic selection*, Proc. Natl. Acad. Sci. USA 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA*, 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology*, 19:456-460 (2001); Smith, *In vitro mutagenesis, Ann. Rev. Genet.* 19:423-462(1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond. A* 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors,*

Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Determining Kinetic Parameters

The polymerases of the invention can be screened or otherwise tested to determine whether the polymerase displays a modified activity for or with a nucleotide analog or template as compared to a parental DNA polymerase (e.g., a corresponding wild-type or available mutant polymerase from which the recombinant polymerase of the invention was derived). For example, branching fraction, a reaction rate constant, $k_{off}$, $k_{cat}$, $K_m$, $V_{max}$, $k_{cat}/K_m$, $V_{max}/K_m$, $k_{pol}$, and/or $K_d$ of the recombinant DNA polymerase for the nucleotide (or analog) or template nucleic acid can be determined. The enzyme perfection metric $k_{cat}/K_m$ is also a useful measure, e.g., for assessing branch rate. $k_{cat}/K_m$ is a measure of substrate binding that leads to product formation (and, thus, includes terms defining binding $K_d$ and inversely predicts branching fraction formation).

As is well-known in the art, for enzymes obeying simple Michaelis-Menten kinetics, kinetic parameters are readily derived from rates of catalysis measured at different substrate concentrations. The Michaelis-Menten equation, $V=V_{max}[S]([S]+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product (this provides an inverse measure of branching rate, as branching rate is the rate at which the enzyme binds substrate (e.g., nucleotide), but does not convert it to product (e.g., a DNA polymer).

$k_{cat}$ (also called the turnover number of the enzyme) can be determined if the total enzyme concentration ([$E_T$], i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics.

Details regarding $k_{off}$ determination are described above. In general, the dissociation rate can be measured in any manner that detects the polymerase/DNA complex over time. This includes stopped-flow spectroscopy, or even simply by taking aliquots over time and testing for polymerase activity on the template of interest. Free polymerase is captured with a polymerase trap after dissociation, e.g., by incubation in the presence of heparin or an excess of competitor DNA (e.g., non-specific salmon sperm DNA, or the like).

In one embodiment, using pre-steady-state kinetics, the nucleotide concentration dependence of the rate constant $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the Burst equation; Product=$A[1-\exp(-k_{obs}*t)]+k_{ss}*t$ where A represents amplitude an estimate of the concentration of the enzyme active site*s, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])-1$ where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" Methods Enzymol. 134:677-705, Patel et al. (1991) "Pre-steady-state kinetic analysis of processive DNA replication including complete characterization of an exonuclease-deficient mutant" Biochemistry 30(2):511-25, and Tsai and Johnson (2006) "A new paradigm for DNA polymerase specificity" Biochemistry 45(32):9675-87.

Parameters such as rate of binding of a nucleotide analog or template by the recombinant polymerase, rate of product release by the recombinant polymerase, or branching rate of the recombinant polymerase can also be determined, and optionally compared to that of a parental polymerase (e.g., a corresponding wild-type polymerase).

For a more thorough discussion of enzyme kinetics, see, e.g., Berg, Tymoczko, and Stryer (2002) Biochemistry, Fifth Edition, W. H. Freeman; Creighton (1984) Proteins: Structures and Molecular Principles, W. H. Freeman; and Fersht (1985) Enzyme Structure and Mechanism, Second Edition, W. H. Freeman.

In one aspect, the improved activity of the enzymes of the invention is compared with a given parental polymerase. For example, in the case of enzymes derived from a Φ29 parental enzyme, where the improvement being sought is an increase in stability of the closed complex, an improved enzyme of the invention would have a lower $k_{off}$ than the parental enzyme, e.g., wild type Φ29. Such comparisons are made under equivalent reaction conditions, e.g., equal concentrations of the parental and modified polymerase, equal substrate concentrations, equivalent solution conditions (pH, salt concentration, presence of divalent cations, etc.), temperature, and the like. In one aspect, the improved activity of the enzymes of the invention is measured with reference to a model analog or analog set and compared with a given parental enzyme.

Optionally, the improved activity of the enzymes of the invention is measured under specified reaction conditions. While the foregoing may be used as a characterization tool, it in no way is intended as a specifically limiting reaction of the invention.

Optionally, the polymerase also exhibits a $K_m$ for a phosphate-labeled nucleotide analog that is less than a $K_m$ observed for a wild-type polymerase for the analog to facilitate applications in which the polymerase incorporates the analog, e.g., during SMS. For example, the modified recombinant polymerase can exhibit a $K_m$ for the phosphate-labeled nucleotide analog that is less than less than 75%, 50%, 25% or less than that of wild-type or parental polymerase such as a wild type Φ29. In one specific class of examples, the polymerases of the invention have a $K_m$ of about 10 µM or less for a non-natural nucleotide analog such as a phosphate labeled analog.

Determining Whether a Polymerase System Exhibits Two Slow Steps

In some cases the presence of two slow steps can be ascertained by the characteristics of the polymerase reaction run under single molecule sequencing conditions, for example by measuring the distribution of pulse widths. For example, a distribution of pulse widths can be determined using systems described herein where the components of the system are labeled such that a bright state is observed during nucleotide binding, and a dark state is observed from after product release until the next nucleotide binding event. Under these conditions a bright pulse will be observed that corresponds to bound nucleotide. The width of the pulse corresponds to the amount of time that the nucleotide is bound. By measuring the width of a number of pulses, corresponding to a number of nucleotide incorporation events, a distribution of pulse widths can be obtained. From this distribution of pulse widths, in some cases, it can be determined that a polymerase reaction having two slow steps is occurring, and in particular, a polymerase reaction having two slow steps during the bright state during which the nucleotide is associated with the polymerase enzyme. The use of a distribution of pulses to determine a kinetic mechanism having two slow (kinetically observable) steps is described, for example, in Miyake et al. Analytical Chemistry 2008 80 (15), 6018-6022.

Analogously, the presence of two slow steps in the dark phase of a polymerase reaction can in some cases be detected by determining the distribution of the time between pulses (interpulse time). Where the system exhibits two slow steps, a distribution described by a double exponential can be seen.

In some cases, it is not possible or not practical to determine under single molecule conditions whether a system is exhibiting two slow-step kinetics. For example, in some cases, the frame time of the detection optics will be slow enough that a significant number of pulses or interpulse times are not detected, precluding a reliable determination of pulse width or interpulse time distribution. In such cases, the presence of two slow-step kinetics under such polymerase reaction conditions can be determined by running a reaction under substantially the same polymerase reaction conditions, but not under single molecule conditions. For example, a reaction can be run under substantially the same polymerase reaction conditions as the single molecule sequencing system, but with a higher concentration of polymerase enzyme and in some cases, a higher concentration of primer and/or template nucleotide. The reaction run under substantially the same polymerase reaction conditions, but with higher concentrations of polymerase enzyme, primer, and/or template can be used to determine whether the system shows two slow steps as described herein. The reaction to determine two slow-step kinetics may have labels on different components of the reaction than that for single molecule sequencing, such as having labels on the template nucleic acid.

For example, a stopped-flow reaction such as described in the examples below can be used to determine whether the polymerase reaction conditions exhibit two slow steps. As described in the examples, stopped-flow experiments can be used to establish that the polymerase reaction is exhibiting two slow step kinetics either in a bright phase or in a dark phase for single molecule sequencing.

A higher enzyme/primer/template concentration reaction such as a stopped-flow reaction can be used to identify systems having two slow steps for single molecule sequencing. Alternatively, the reaction run under substantially the same conditions but higher concentration of enzyme/primer/template can be used to verify that a single molecule sequencing system is being carried out under polymerase reaction conditions that exhibit two slow steps.

Screening Polymerases

Screening or other protocols can be used to determine whether a polymerase displays a modified activity, e.g., for a nucleotide analog, as compared to a parental DNA polymerase. For example, branching fraction, rate constant, $k_{off}$, $k_{cat}$, $K_m$, $V_{max}$, or $k_{cat}/K_m$ of the recombinant DNA polymerase for the template or nucleotide or analog can be determined as discussed above. As another example, activity can be assayed indirectly, e.g., as described in Example 4.

In one desirable aspect, a library of recombinant DNA polymerases can be made and screened for these properties. For example, a plurality of members of the library can be made to include one or more mutation that alters (e.g., decreases) reaction rate constants, improves closed complex stability, or decreases branching fraction and/or randomly generated mutations (e.g., where different members include different mutations or different combinations of mutations), and the library can then be screened for the properties of interest (e.g., decreased rate constant, decreased branching fraction, or increased closed complex stability). In general, the library can be screened to identify at least one member comprising a modified activity of interest.

Libraries of polymerases can be either physical or logical in nature. Moreover, any of a wide variety of library formats can be used. For example, polymerases can be fixed to solid surfaces in arrays of proteins. Similarly, liquid phase arrays of polymerases (e.g., in microwell plates) can be constructed for convenient high-throughput fluid manipulations of solutions comprising polymerases. Liquid, emulsion, or gel-phase libraries of cells that express recombinant polymerases can also be constructed, e.g., in microwell plates, or on agar plates. Phage display libraries of polymerases or polymerase domains (e.g., including the active site region or interdomain stability regions) can be produced. Likewise, yeast display libraries can be used. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems which can interface directly with microwell plates for fluid handling.

Desirable Properties

The polymerases of the invention can include any of a variety of modified properties towards natural nucleotides and/or nucleotide analogs, depending on the application, including decreased branching fraction, increased closed complex stability, increased speed, increased retention time (or decreased speed) for incorporated bases, greater processivity, slower product release, slower isomerization, slower translocation, etc. For example, $k_{off}$ can be measured to detect closed complex stability, as noted herein. $k_{cat}/K_m$ can be determined as an inverse measure of branch formation. Alternately, branch formation can be directly monitored in high-throughput SMS reactions using known templates. Branch fraction formation or complex stability can be screened for or against in selecting a polymerase of the invention, e.g., by screening enzymes based on kinetic or product formation properties.

For example, improvements in a dissociation rate (or improved processivity) of 30% or more, e.g., about 50%, 75%, or even 100% or more can be screened for in identifying polymerases that display closed complex stability. Similarly, detecting mutant polymerases that form branching fractions of less than 25%, e.g., 10% or less, 5% or less, and even 1% or 0.1% or less is a feature of the invention.

Additional Example Details

A number of specific examples of modified active site and interdomain regions are described herein. An "active site region" is a portion of the polymerase that includes or is proximal to the active site (e.g., within about 2 nm of the active site) in a three dimensional structure of a folded polymerase. Similarly, an interdomain region or residue occurs in the region between two domains, e.g., when the enzyme is in the closed conformation or a closed complex. Specific examples of structural modifications within or proximal to the active site or interdomain regions of Φ29 DNA polymerase are described herein.

The polymerase optionally further includes one or more mutations/deletions relative to the wild-type polymerase that provide additional properties of interest, including reducing or eliminating endogenous exonuclease activity, deletion or insertion of steric features near the active site that improve specificity for an unnatural nucleotide, or that improve surface bound activity of the protein, or the like. A variety of useful additional mutations that can be used in combination with the present invention are described, e.g., in WO 2007/076057 POLYMERASES FOR NUCLEOTIDE ANALOGUE INCORPORATION by Hanzel et al.; WO 2008/051530 POLYMERASE ENZYMES AND REAGENTS FOR ENHANCED NUCLEIC ACID SEQUENCING by Rank et al.; WO 2007/075987 ACTIVE SURFACE COUPLED POLYMERASES by Hanzel et al.; and WO 2007/076057 PROTEIN ENGINEERING STRATEGIES TO OPTIMIZE ACTIVITY OF SURFACE ATTACHED PROTEINS by Hanzel et al.

As will be appreciated, the numbering of amino acid residues is with respect to a particular reference polymerase, such as the wild-type sequence of the Φ29 polymerase (Table 5); actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

Affinity Tags And Other Optional Polymerase Features

The recombinant DNA polymerase optionally includes additional features exogenous or heterologous to the polymerase. For example, the recombinant polymerase optionally includes one or more exogenous affinity tags, e.g., purification or substrate binding tags, such as a polyhistidine tag sequence, a 6 His tag sequence, a GST tag, an HA tag sequence, a plurality of 6 His tag sequences, a plurality of GST tags, a plurality of HA tag sequences, a SNAP-tag, a c-myc tag, a c-myc fusion, or the like. These and other features useful in the context of binding a polymerase to a surface are optionally included, e.g., to orient and/or protect the polymerase active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, His tags, etc.) are typically located in the N-terminal region to avoid interfering with the active site when the polymerase is coupled to a surface.

In general, surface binding elements and purification tags that can be added to the polymerase (recombinantly or, e.g., chemically) include, e.g., polyhistidine tags, HIS-6 tags, biotin, avidin, GST sequences, modified GST sequences, e.g., that are less likely to form dimers, biotin ligase recognition (BiTag) sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface, attaching tags, and the like are found in WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al. Further details on attaching tags is available in the art. See, e.g., U.S. Pat. Nos. 5,723,584 and 5,874,239 for additional information on attaching biotinylation peptides to recombinant proteins.

Making and Isolating Recombinant Polymerases

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase of the invention, e.g., a mutant polymerase that, without being bound to a particular theory, decreases reaction rate, increases closed complex stability, or that includes a nucleotide complementarity/active site access feature that makes the enzyme more efficient at using the nucleotide (decreasing branching fraction). Recombinant methods for making nucleic acids, expression and isolation of expressed products are well known and described in the art. Optionally, when modifying the active site, features are selected (e.g., by modeling, though random approaches can also be used) that improve steric access of the nucleotide analog to the active site and/or that improves charge-charge or hydrophobic interactions between a given nucleotide analog and the polymerase target. Methods for making and selecting mutations in the active site of polymerases, including for modifying steric features in or near the active site to permit improved access by nucleotide analogs are found, e.g., in WO 2007/076057 POLYMERASES FOR NUCLEOTIDE ANALOGUE INCORPORATION by Hanzel et al., and WO 2008/051530 POLYMERASE ENZYMES AND REAGENTS FOR ENHANCED NUCLEIC ACID SEQUENCING by Rank et al.

Additional useful references for mutation, recombinant and in vitro nucleic acid manipulation methods (including cloning, expression, PCR, and the like) include Berger and Kimmel, *Guide to Molecular Cloning Techniques, Methods in Enzymology volume* 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) PCR *Cloning Protocols, Second Edition* (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

In addition, systems of orthogonal components are available that can incorporate any of a variety of unnatural (non-natural) amino acids into a recombinant protein (e.g., polymerase of the invention). In brief, a cell or other translation system (e.g., an in vitro translation system) is constructed that includes an orthogonal tRNA ("OtRNA," a tRNA not recognized by the cell's endogenous translation machinery, such as an amber or 4-base tRNA) and an orthogonal tRNA synthetase ("ORS," a synthetase that does not aminoacylate any endogenous tRNA of the cell but which can aminoacylate the OtRNA in response to a selector codon). A nucleic acid encoding the enzyme is constructed to include a selector codon at a selected position that is specifically recognized by the OtRNA. The ORS specifically incorporates an unnatural amino acid with a desired chemical functionality at one or more selected sites. This chemical functional group can be unique as compared to those ordinarily found on amino acids. These are coupled to the coupling domains through appropriate chemical linkages. Further information on orthogonal systems can be found, e.g., in Wang et al. (2001) Science 292:498-500, Chin et al. (2002) Journal of the American Chemical Society 124:9026-9027, Chin and Schultz (2002) ChemBioChem 11:1135-1137, Chin et al. (2002) PNAS 99:11020-11024, and Wang and Schultz (2002) Chem. Comm., 1-10. See also, International Publications WO 2002/086075, entitled "METHODS AND COMPOSITIONS FOR THE PRODUCTION OF ORTHOGONAL tRNA AMINOA-CYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) Plant Cell, *Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A variety of protein isolation and detection methods are known and can be used to isolate polymerases, e.g., from recombinant cultures of cells expressing the recombinant polymerases of the invention. A variety of protein isolation and detection methods are well known in the art, including, e.g., those set forth in R. Scopes, *Protein*

Purification, Springer-Verlag, N.Y. (1982); Deutscher, *Methods in Enzymology Vol.* 182: *Guide to Protein Purification*, Academic Press, Inc. N.Y. (1990); Sandana (1997) *Bioseparation of Proteins*, Academic Press, Inc.; Bollag et al. (1996) *Protein Methods, 2nd Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Kits

The present invention also features kits that incorporate the polymerases of the invention, optionally with additional useful reagents such as one or more nucleotide analogs, e.g., for sequencing, nucleic acid amplification, or the like. Such kits can include the polymerase of the invention packaged in a fashion to enable use of the polymerase, a set of different nucleotide analogs of the invention, e.g., those that are analogous to A, T, G, and C, e.g., where one or more of the analogs comprise a detectable moiety, to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions such as $Ca^{++}$, $Mg^{++}$, $Mn^{++}$ and/or $Fe^{++}$, and standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequence and Variants

As described herein, the invention also features polynucleotide sequences encoding, e.g., a polymerase as described herein. Examples of polymerase sequences that include features found herein, e.g., as in Tables 1-3, are provided. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of a polymerase of Tables 1-3 or any other specifically listed polymerase herein. Combinations of any of the mutations noted herein or combinations of any of the mutations herein in combination with those noted in other available references relating to improved polymerases, such as Hanzel et al WO 2007/076057 POLYMERASES FOR NUCLEOTIDE ANALOGUE INCORPORATION; Rank et al. WO 2008/051530 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057 PROTEIN ENGINEERING STRATEGIES TO OPTIMIZE ACTIVITY OF SURFACE ATTACHED PROTEINS are also features of the invention Accordingly, the invention provides a variety of polypeptides (polymerases) and polynucleotides (nucleic acids that encode polymerases). Example polynucleotides of the invention include, e.g., any polynucleotide that encodes a polymerase of Tables 1-3 or otherwise described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers decreased branching or increased complex stability.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 4

Conservative Amino Acid Substitutions

| Nonpolar and/ or Aliphatic Side Chains | Polar, Uncharged Side Chains | Aromatic Side Chains | Positively Charged Side Chains | Negatively Charged Side Chains |
| --- | --- | --- | --- | --- |
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Nucleic Acid Hybridization

Comparative hybridization can be used to identify nucleic acids of the invention, including conservative variations of nucleic acids of the invention. In addition, target nucleic acids which hybridize to a nucleic acid of the invention under high, ultra-high and ultra-ultra high stringency conditions, where the nucleic acids encode mutants corresponding to those noted in Tables 1-3 or other listed polymerases, are a feature of the invention. Examples of such nucleic acids include those with one or a few silent or conservative nucleic acid substitutions as compared to a given nucleic acid sequence encoding a polymerase of Tables 1-3 (or other exemplified polymerase), where any conservative substitutions are for residues other than those noted in Tables 1-3 or elsewhere as being relevant to a feature of interest (improved closed complex stability, decreased branch fraction formation, etc.).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization of the probe to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology-Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid that encodes a polymerase of Tables 1-3 or others described herein. The unique subsequence may be unique as compared to a nucleic acid corresponding to, e.g., a wild type Φ29. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polymerase of Tables 1-3 or otherwise detailed herein. Here, the unique subsequence is unique as compared to, e.g., wild type Φ29 or previously characterized mutation thereof.

The invention also provides for target nucleic acids which hybridize under stringent conditions to a unique coding oligonucleotide which encodes a unique subsequence in a polypeptide selected from the modified polymerase sequences of the invention, wherein the unique subsequence is unique as compared to a polypeptide corresponding to wild type Φ29. Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

For reference, the amino acid sequence of a wild-type Φ29 polymerase is presented in Table 5.

TABLE 5

| Wild-type Φ29 amino acid sequence. |
|---|
| SEQ ID NO: 1 mkhmprkmys cdfetttkve dcrvwayqym niedhseyki gnsldefmaw vlkvqadlyf hnlkfdgafi inwlerngfk wsadglpnty ntiisrmgqw ymidiclgyk gkrkihtviy dslkklpfpv kkiakdfklt vlkgdidyhk erpvgykitp eeyayikndi qiiaealliq fkqgldrmta gsdslkgfkd |

TABLE 5-continued

Wild-type Φ29 amino acid sequence.

```
iittkkfkkv fptlslgldk evryayrggf twlndrfkek
eigegmvfdv nslypaqmys rllpygepiv fegkyvwded
yplhiqhirc efelkegyip tiqikrsrfy kgneylkssg
geiadlwlsn vdlelmkehy dlynveyisg lkfkattglf
kdfidkwtyi kttsegaikq laklmlnsly gkfasnpdvt
gkvpylkeng algfrlgeee tkdpvytpmg vfitawaryt
titaaqacyd riiycdtdsi hltgteipdv ikdivdpkkl
gywahestfk rakylrqkty iqdiymkevd gklveqspdd
ytdikfsvkc agmtdkikke vtfenfkvgf srkmkpkpvq
vpggvvlvdd tftik
```

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

Determination of Branching Fractions for Modified Recombinant Polymerases

An active polymerase:template:analog ternary complex can be created in a 'static' non-extending (a.k.a 'sampling') configuration by including in the reaction a divalent cation that supports access of analog bases into the binding pocket but does not have sufficient coordination capability to allow the active configuration of the analog be assumed. The divalent cation that most efficiently fulfills this function for a polymerase extension reaction is calcium.

Figure 11A:
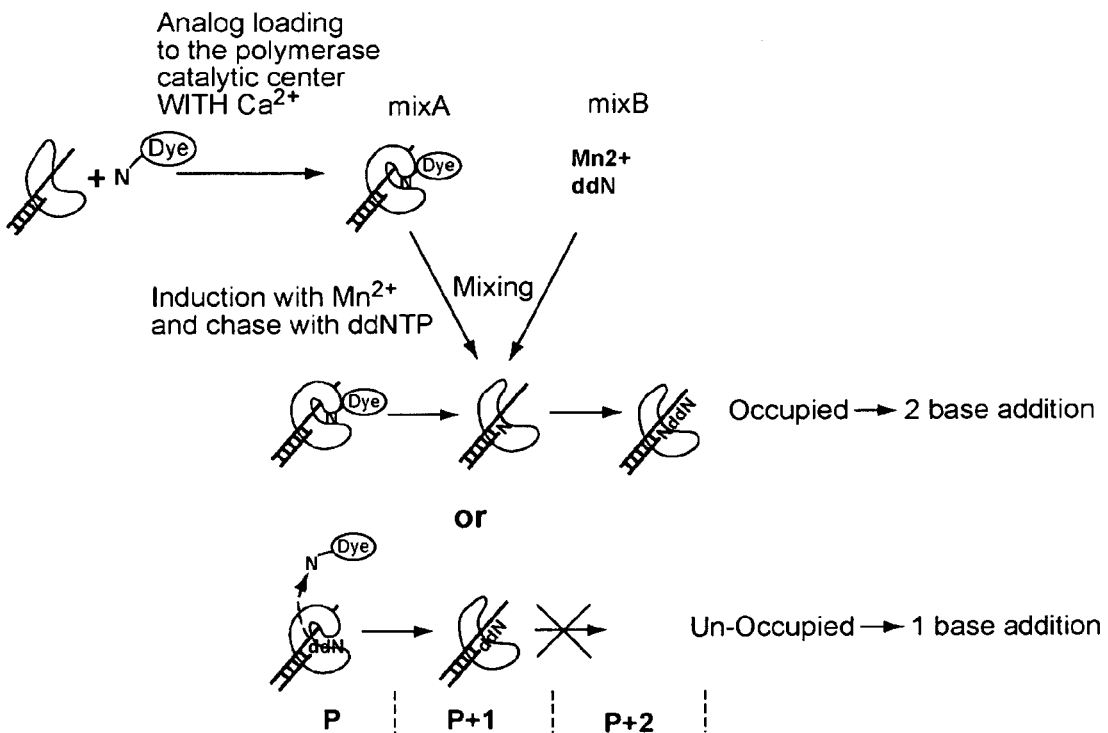
FIG. 11 Panel A schematically illustrates an assay for determination of branching fraction. Panel B illustrates detection of primer (P) and +1 and +2 products by gel electrophoresis.
Figure 11B:
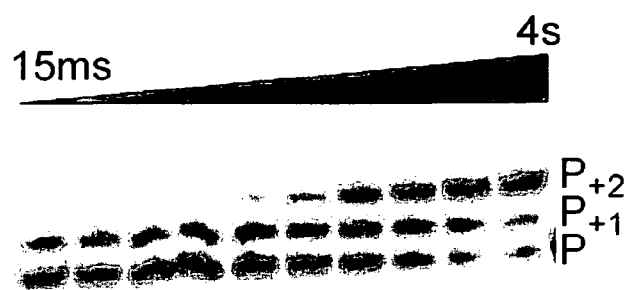

To perform a branching fraction assay, this static structure is leveraged by (for any variant being tested) initiating such a reaction that precludes extension, then (at a fixed time point) 'chasing' this state with saturating amounts of a dideoxynucleotide (or other non-hydrolyzable analog), extendable base analogs, and a divalent cation that supports product extension. The simultaneous addition of these three components results in sites that are unoccupied at the time of the 'chase' being terminated by the rapid, high-affinity binding of the non-hydrolyzable analog. This results in generation of a product that is only a single base longer then the original primer. Sites that are 'occupied' (i.e. contain the cognate, but unpaired, analog base) will (as a result of the 'chase' reaction) proceed with extension (the resident analog base completes chemistry with the free 3' OH group of the primer) and thereby generates a product that can be detected as a two (or more)-base addition(s). The ratio of the amount of these two products is used to estimate the proportion of unoccupied and occupied sites at an equilibrium state and therefore is proportional to the rate of branching. The assay is schematically illustrated in FIG. 11 Panel A.

Materials and Methods

In general, branching fraction can be determined as follows. Combine polymerase sample with 1 mM calcium chloride, the analog for testing, and an appropriate template: primer where the bases at position +1 and +2 are complementary to the test analog. Incubate at optimum polymerase reaction temperature for 5 minutes. Add to this reaction an equal volume of the same formulation containing 20-fold level of manganese over the calcium chloride concentration and 0.5 mM of a non-hydrolyzable nucleotide (of the same base as the analog being tested). Incubate at same temperature for 30 seconds. Terminate the reaction either by adding EDTA to a final concentration of 100mM or by adding a denaturing reagent such as formamide. Analyze samples to determine the amounts of the +1 and +2 products—this can be done by acrylamide gel electrophoresis (FIG. 11 Panel B) or capillary electrophoresis. The branching fraction is calculated as the proportion of the amount of the +1 product to the total amount of products formed (+1++2), i.e., branching fraction=$P_{+1}/(P_{+1}+P_{+2})$.

Branching fraction data presented for the Φ29 polymerase mutants in Table 1 was determined accordingly, under the following conditions. The analog, template, and primer employed were analog A555-dT6P, template 5'-ACGACGT-TGACAATAATACAAGTCCGATACAT-GATAATTACCGATAAGTTCGTC GAGAGCACATTAG-GCTGGCTG G-3' (SEQ ID NO:2), and primer 5'6-FAM/CCAGCCAGCCTAATGTGCTCTCGACGAACTTATCG-GTAATTATCATGTATC GGA C-3' (SEQ ID NO:3). Combine 130 nM Polymerase with 40 nM annealed Template: Primer in a solution containing 1 mM CaCl$_2$, 5 uM Analog, 0.095% Triton X-100, 75 mM Potassium Acetate, 5 mM DTT in 50 mM ACES pH 7.25 at a volume of 20 uL. Incubate at room temperature for 5 minutes. In a separate tube, combine 20 mM MnCl$_2$ with 0.5 mM 3'-amino-2'ddTTP in 50 mm ACES pH 7.25. At the completion of the 5 minute incubation step, transfer 20 uL of the second mix to the first. Incubate for 30 seconds at room temperature. Add EDTA to 5 mM to quench the reaction. Analyze samples by separating fragments by capillary electrophoresis and calculating integrated peak areas of the products.

Example 2

Polymerase Systems Having Two Kinetically Observable Steps—Stopped Flow Measurements This experiment describes the observation of a polymerase system having two kinetically observable steps (two slow steps) where the two kinetically observable steps occur while the nucleotide is associated with the enzyme (after nucleotide binding and through product release). In the experiment described here, the two kinetically observable steps would correspond to steps occurring in the bright state of a single-molecule sequencing system using nucleotides having dyes attached to the terminal phosphate of the nucleotides.

The oligonucleotides that constitute the template/primer complex were purchased from Integrated DNA Technologies (Coralville, Iowa). The position iAmMC6T has an Int amino modified C6 dT substituted for dT at this position. The "template" oligonucleotide was labeled at position "iAmMC6T" with alexa fluor 488 fluorescent dye.

Sequence of oligonucleotides used for the assays were (SEQ ID NO: 4)
5'-GGT GAT GTA GAT AGG TGG TAG GTG GTG TCA_____GAT C (SEQ ID NO: 5)
3'-CCA CTA CAT CTA TCC ACC ATC CAC CAC AG/iAmMC6T/ CTA GGC ATA ATA ACA GTT GCA GCA This stopped-flow assay relies on the quenching, for example by fluorescent resonance energy transfer (FRET) of the fluorescence of the Alexa fluor 488 attached to the template by a dye labeled nucleotide. A nucleotide having an Alexa fluor 555 as a terminal phosphate label is used in the polymerase reaction, which will quench the fluorescence of the Alexa fluor 488 dye attached to the template only when the nucleotide is associated with (bound to) the polymerase enzyme.

For this assay a SF-2004 stopped-flow instrument (Kintek Corp, Austin, Tex.) is used to monitor the fluorescence at 535 nm (using a band pass filter), to measure Alexa fluor 488 emission. The enzyme, DNA, buffer, potassium acetate, and dithiothreitol (DTT) are mixed in one sample and allowed to equilibrate. Alexa-555-dC6P (a terminally labeled hexaphosphate nucleotide substrate), buffer, potassium acetate, DTT, $MnCl_2$, and $CaCl_2$ are mixed in a second sample. The stopped-flow instrument rapidly mixes these samples and reads the fluorescent signal at 535 nm as a function of time.

The drop in the fluorescent signal, measured at 535 nM, is attributed to binding of the Alexa-555-dC6P nucleotide to the enzyme-DNA complex. Because quenching only occurs when the two dyes are in close proximity, a significant drop in the fluorescence of alexa fluor 488 due to the presence of alexa fluor 555 in solution would not be expected to occur. Alexa-555-dC6P bound in the active site of the enzyme, however, will cause a drop in the fluorescence of alexa fluor 488 labeled oligonucleotide. The rate of drop of the measured fluorescence signal is a function of the rate of binding of the nucleotide to the active site of the enzyme.

Once bound, the nucleotide analog can undergo nucleotidyl transfer catalyzed by the polymerase enzyme, extending the oligonucleotide. Subsequent to extension of the oligonucleotide, the product, the alexa fluor 555-pentaphosphate is released from the enzyme. Once released from the enzyme DNA complex, the alexa fluor 555-pentaphosphate no longer quenches the alexa fluor 488 attached to the template in the enzyme-DNA complex, and the measured fluorescence signal increases at a rate that is a function of the release of product.

The binding of the nucleotide to the enzyme-DNA complex is often observed to occur as a single exponential decrease in the fluorescence signal, indicating a process with a single kinetically observable step. Where the steps of the polymerase reaction from after binding through release of the pentaphosphate-dye molecule are governed by a single rate limiting step a single exponential increase in the fluorescent signal is expected. Thus, in the scenario where nucleotide binding and the subsequent steps through product release are each governed by single rate limiting steps, a fluorescent signal that is adequately described by a sum of two exponentials is observed.

Figure 15:
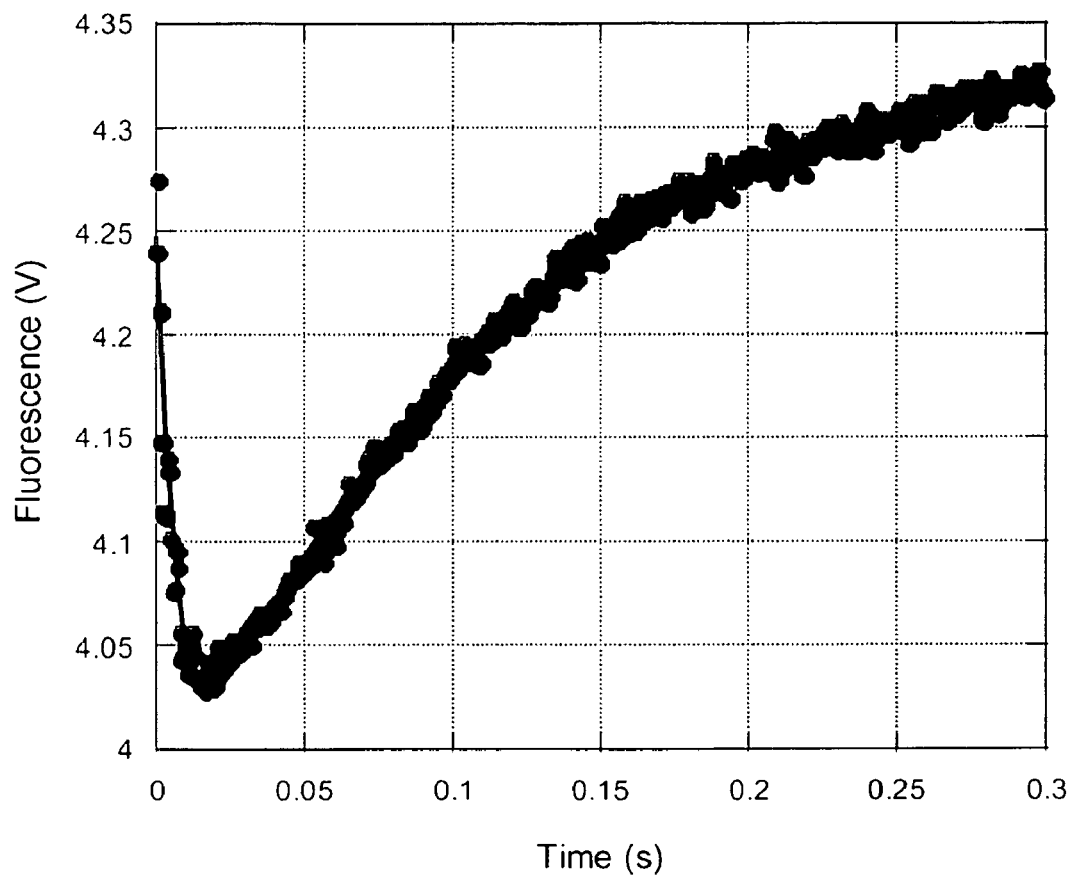
FIG. 15 shows the results of a stopped-flow experiment for a polymerase reaction system in which the decrease in the fluorescent signal fits to a single exponential and the increase in signal fits to a single exponential.

FIG. 15 shows the data from a polymerase reaction system in which the decrease in the fluorescent signal fits to a single exponential having an observed rate constant of 156±3 $s^{-1}$, and the increase in signal fits to a single exponential having an observed rate constant of 8.5±0.1 $s^{-1}$. FIG. 15 includes both the experimental data and the curve fits for single exponential decay and rise in fluorescence. The polymerase reaction shown in FIG. 15 involved a modified phi29 DNA polymerase having the mutations N62D/T368F/E375Y/K512Y and modified for streptavidin binding (polymerase R) in 50 mM ACES buffer at a pH of 7.1. The assay was performed with the following components and amounts: 0.125 µM polymerase R enzyme, 0.025 µM DNA, 50 mM ACES, pH 7.1, 0.7 mM $MnCl_2$, 75 mM potassium acetate, 5 mM dithiothreitol, 3 µM alexa 555-dC6P. The observed fluorescent signal was fit to a sum of two exponentials, where the rate of the drop is 156±3 $s^{-1}$, and the rate of the increase in signal is 8.5±0.1 $s^{-1}$.

Figure 16:
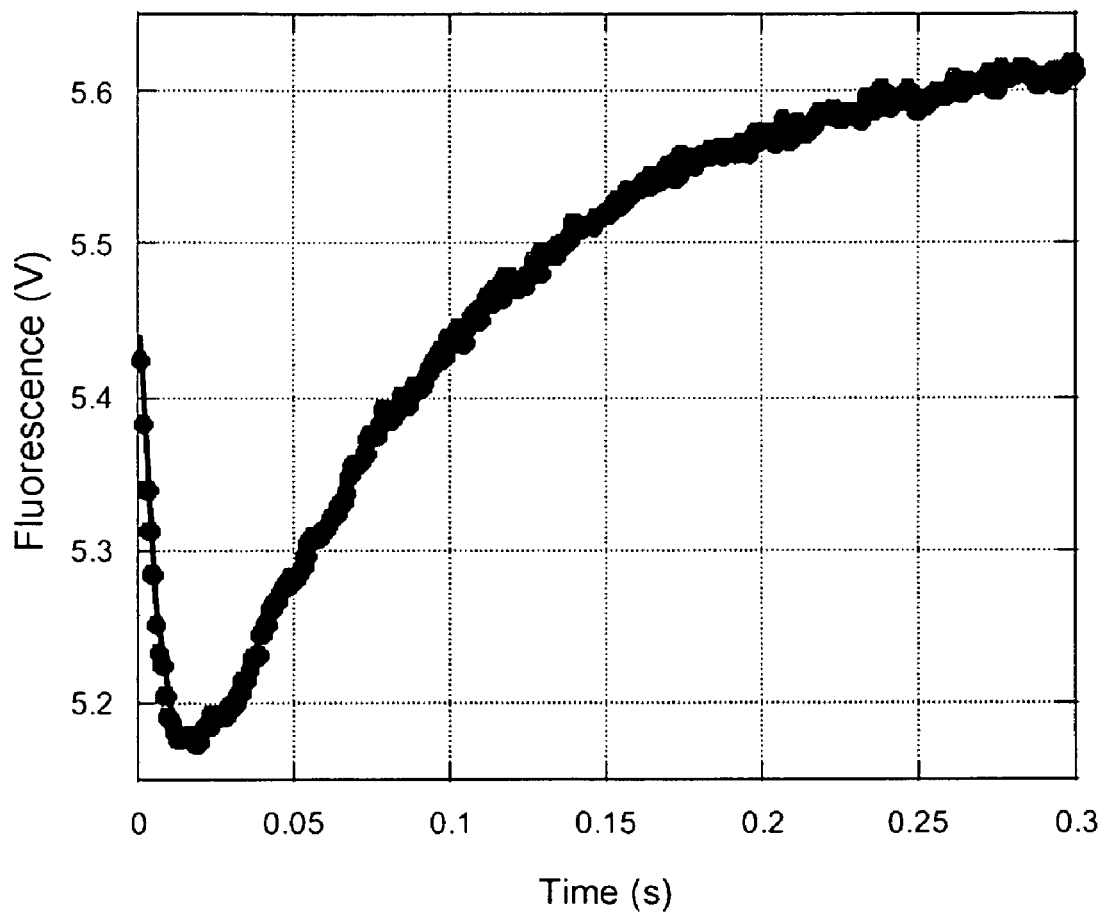
FIG. 16 shows the results of a stopped-flow experiment for a polymerase reaction system in which the decrease in the fluorescent signal fits to a single exponential and the increase in signal is best described by two exponentials.

FIG. 16 shows the data for a polymerase reaction system which exhibits two kinetically observable steps for the steps after nucleotide binding through product release. The polymerase reaction used the enzyme polymerase R in 50 mM Tris buffer, at pH 7.1, with 0.25 mM $CaCl_2$. The assay used 0.125 µM polymerase R enzyme, 0.025 µM DNA, 50 mM Tris, pH 7.1, 0.7 mM $MnCl_2$, 0.25 mM $CaCl_2$, 75 mM potassium acetate, 5 mM dithiothreitol, 3 µM alexa 555-dC6P. A good fit to the data could not be obtained with two exponentials. However, a good quality fit was obtained using the sum of three exponentials. The drop in fluorescence occurs with a single exponential having an observed rate constant of 172±12 $s^{-1}$. The increase in fluorescence is best described as the sum of two exponentials, where the faster of the two steps occurs with an observed rate constant of 60±10 $s^{-1}$, and the slower of the two steps occurs with an observed rate constant of 12.0±0.1 $s^{-1}$. The behavior of this system is best described by two kinetically observable steps during the part of the polymerase reaction in which the nucleotide is associated with the enzyme. Each of the steps is partially rate limiting. The observed fluorescent signal is fit to a sum of three exponentials, where the observed rate constant for the drop in fluorescence is 172±12 $s^{-1}$, and the increase in fluorescence exhibits two kinetically observable rate constants, one at 60±10 $s^{-1}$ and the other at 12.0±0.1 $s^{-1}$.

Figure 17:
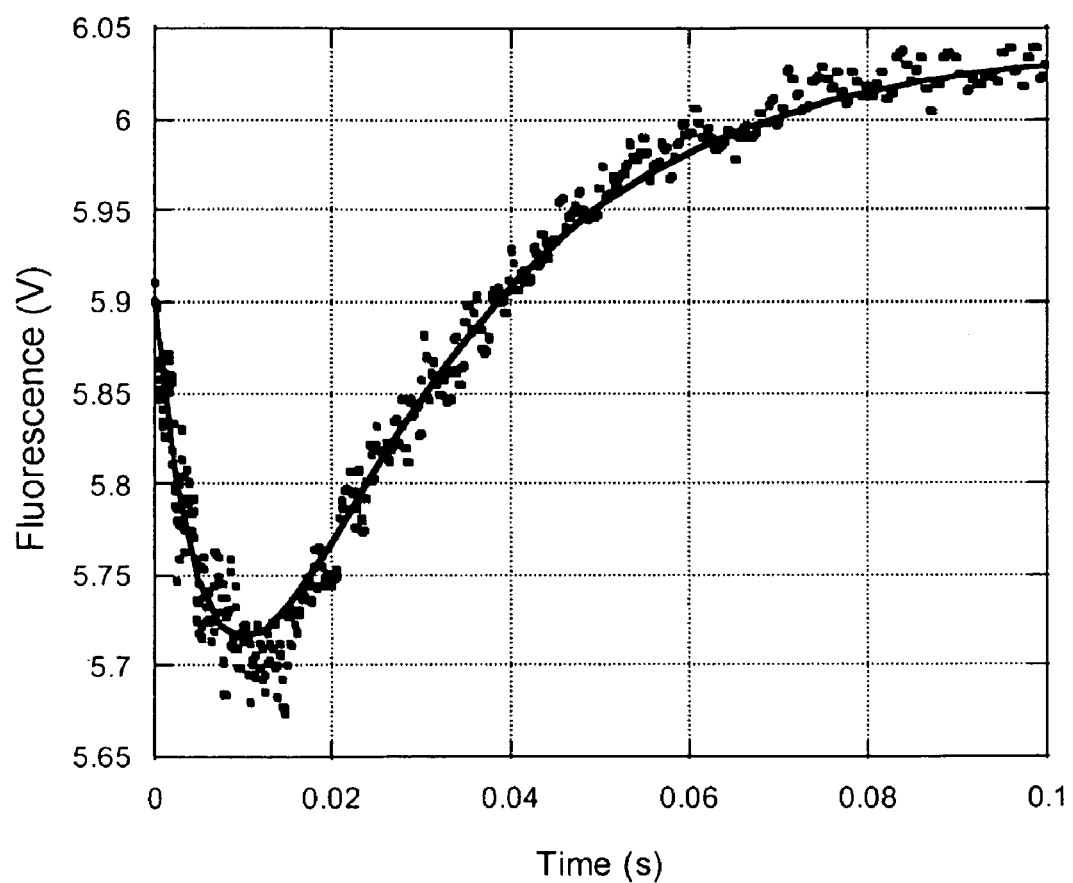
FIG. 17 shows the results of a stopped-flow experiment for a polymerase reaction system in which the decrease in the fluorescent signal fits to a single exponential and the increase in signal fits to a single exponential.

FIG. 17 shows stopped-flow experimental data for a polymerase having a drop in fluorescence and a rise in fluorescence which each can be fit to a single exponential. FIG. 17 shows the incorporation of Alexa 555-dC6P by a phi29 DNA polymerase enzyme having the mutations N62D/T368F/E375Y/A484E/K512Y and modified for streptavidin binding (polymerase T) in 50 mM Tris buffer, pH 7.1. The assay used 0.125 µM polymerase T enzyme, 0.025 µM DNA, 50 mM Tris, pH 7.1, 0.7 mM $MnCl_2$, 75 mM potassium acetate, 5 mM dithiothreitol, 3 µM alexa 555-dC6P. The observed fluorescent signal is fit to a sum of two exponentials (red curve), where the rate of the drop has an observed rate constant of 118±4 s−1, and the increase in the signal rate limiting step occurs with an observed rate constant of 46±1 s−1.

Figure 18B:
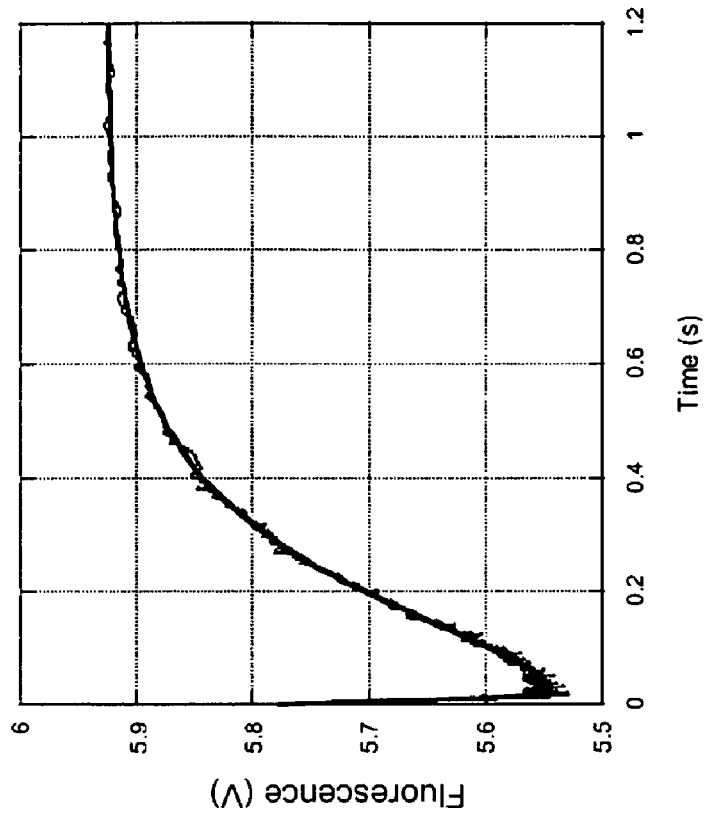
FIG. 18 Panels A and B show the results of a stopped-flow experiment for a polymerase reaction system in which the decrease in the fluorescent signal fits to a single exponential and the increase in signal is best described by to two exponentials (Panel B), and is poorly fit by a single exponential (Panel A).
Figure 18A:
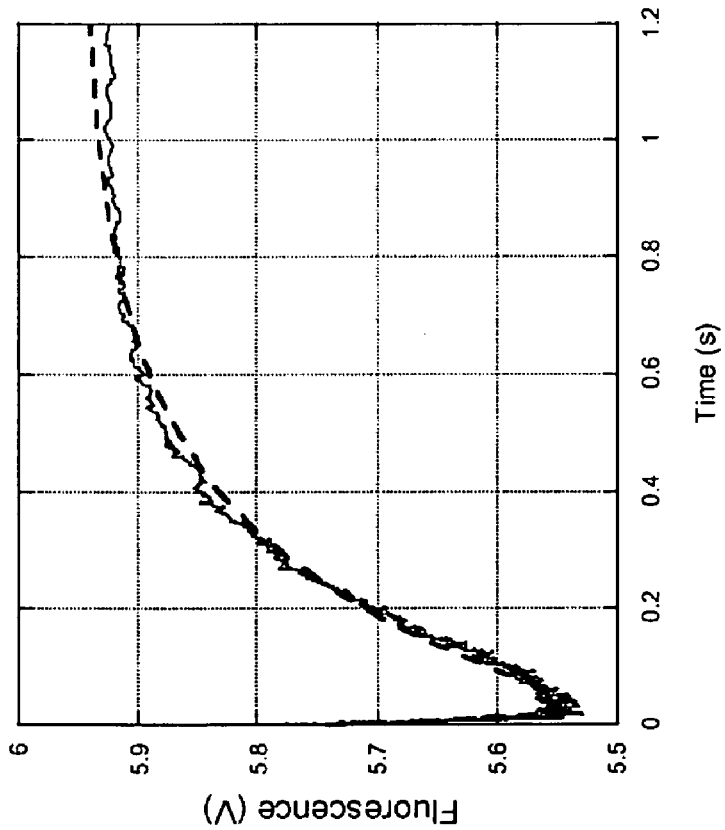

FIG. 18 illustrates how changing the polymerase reaction conditions can produce a polymerase reaction system which exhibits two kinetically observable rate limiting steps for the steps after nucleotide binding through product release. In this case, without limitation to any particular mechanism, it is believed that specific enzyme mutations in the polymerase T enzyme, coupled with the presence of Ca++ under the conditions of the polymerase reaction described, has changed the kinetic performance of the system to obtain a system in which there are two kinetically observable rate constants between nucleotide binding through product release with almost equal rate constants. FIG. 18 shows stopped-flow data for the incorporation of Alexa 555-dC6P by polymerase enzyme polymerase T in 50 mM Tris buffer, pH 7.1, with 1.25 mM $CaCl_2$. The assay used 0.125 µM polymerase T enzyme, 0.025 µM DNA, 50 mM Tris, pH 7.1, 0.7 mM $MnCl_2$, 1.25 mM $CaCl_2$, 75 mM potassium acetate, 5 mM dithiothreitol, 3 µM alexa 555-dC6P. FIG. 18 Panel A shows an attempt to fit the data with two exponentials, one for the decay, and the other for the rise in fluorescence. It can be seen from FIG. 18 Panel A that the data is not well described in this manner. FIG. 18 Panel B shows the observed fluorescent signal fit to a sum of three exponentials where the rate constant for the drop in fluorescence is $157\pm5$ $s^{-1}$, and the increase in the signal exhibits two kinetically observable steps, where one step exhibits an observed rate constant of $9\pm2$ $s^{-1}$ and the other step exhibits a rate constant of $7\pm1$ $s^{-1}$. The conditions that resulted in the two kinetically observable steps of FIG. 18 Panel B are the same as those for the experiment shown in FIG. 17, except for the presence of $CaCl_2$ at a concentration of 1.25 mM in this experiment.

A similar stopped-flow experiment was performed with a modified Φ29 DNA polymerase having the mutations N62D/T368F/E375Y/K512Y/N387L in Tris buffer at a pH of 7.1 with 0.5 mM $MnCl_2$ and no added $CaCl_2$. Data was fit with three exponentials, revealing a ratio between the two slow rates of about 0.5.

Example 3

Stopped Flow Experiment to Observe Two Kinetically Observable Steps for the Steps After Product Release Through Nucleotide Binding The presence of two kinetically observable steps after product release through nucleic acid binding can be observed by measuring the difference in the kinetics of single incorporation and multiple incorporations. First, a transient incorporation nucleotide incorporation assay (rapid chemical quench flow or stopped-flow fluorescence) is performed in order to determine the apparent rate constant for binding of a first nucleotide. Next, the experiment is run such that two nucleotides are incorporated. By comparing the kinetic parameters for the incorporation of two nucleotides as compared to those for incorporating one nucleotide, it can be determined whether there is an intervening step, such as translocation or isomerization, which significantly limits the rate. Where such a step is identified, the pseudo first order rate constant of the nucleotide binding step can be lowered by lowering the concentration of nucleotide. In this manner, a system having two slow steps in the phase after product release and through nucleotide binding can be produced by matching the apparent rate constant of nucleotide binding with that the preceding isomerization or translocation event.

Example 4

High Throughput Screen for Polymerase Mutants with Slow Product Release

As described above, polymerases exhibiting slow release of polyphosphate product are of particular interest, e.g., in producing polymerases exhibiting two slow steps for use in single molecule sequencing. Screening polymerase mutants using a stopped-flow assay to determine kinetic parameters, however, can be time-consuming. A higher throughput format for identifying polymerase variants exhibiting slow product release has thus been developed.

In the screen, each candidate polymerase mutant is employed in a primer extension reaction using a DNA template (e.g., a circular DNA template) and four dNTPs or analogs, in the presence or absence of a competitive inhibitor. Nucleotide incorporation is measured based upon elongation rate of the polymerization reaction, as determined from the change in synthesis product size (e.g., as determined by agarose gel electrophoresis).

Figure 19A:
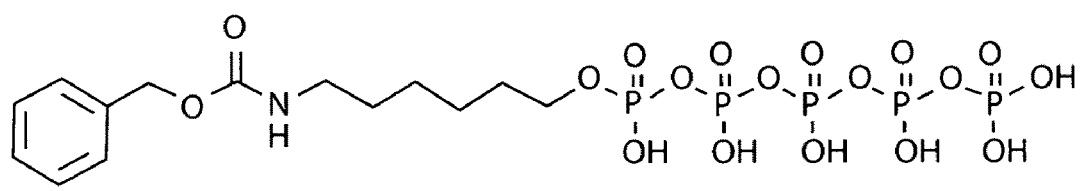
FIG. 19 Panel A depicts the unincorporatable competitive inhibitor Cbz-X-5P. Panels B and C show agarose gels of template dependent, polymerase mediated nucleic acid extension products in the presence of varying concentrations of Cbz-X-5P for two modified Φ29 polymerases.
Figure 19B:
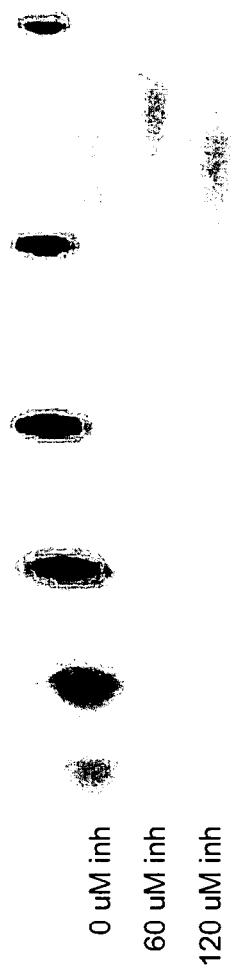
Figure 19C:

Suitable competitive inhibitors include, but are not limited to, Z-6-aminohexylpentaphosphate (Cbz-X-5P, FIG. 19 Panel A). Synthesis of Cbz-X-5P has been described in U.S. patent application Ser. No. 12/370,472, which also describes additional exemplary inhibitors. Without limitation to any particular mechanism, Cbz-X-5P mimics the polyphosphate reaction product and competes with dNTP binding, slowing primer extension. The assay is predicated on product affinity as an indication of slow product release; that is, mutants with slower product release are expected to have greater affinity for the competitive inhibitor and thus show a slower extension rate. Candidate mutants identified by the primer extension screen as potentially having decreased product release rates can be verified if desired, e.g., by stopped-flow measurements. The screen is optionally automated or partially automated.

Illustrative results are shown in FIG. 19 Panels B and C. DNA primer extension reactions were carried out using a circular template and a Φ29 polymerase in the presence of 5 µM native nucleotides (dNTPs), $MnCl_2$, ACES pH 7.1, 75 mM potassium acetate, and various concentrations of Cbz-X-5P (0 µM, 60 µM, and 120 µM). Products were analyzed by agarose gel electrophoresis.

As shown in FIG. 19 Panel B, for parental 129 polymerase N62D/E375Y/K512Y/T368F, increased concentration of the competitive inhibitor yielded a reduction in the size of the extension product. (A molecular weight standard is shown in the leftmost lane.) As shown in FIG. 19 Panel C, no product for modified Φ29 N62D/E375Y/K512Y/T368F/A484E is seen on inclusion of the competitive inhibitor. The strong inhibition of primer extension by Cbz-X-5P agrees with results of stopped-flow experiments for this mutant.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application at the time of its filing are incorporated by reference in their entirety for all purposes to the same extent as if each individual publication, patent, patent application, and/or other document were individually indicated to be incorporated by reference for all purposes.

What is claimed is:

1. A composition comprising a modified recombinant Φ29-type DNA polymerase, which modified recombinant polymerase comprises an amino acid sequence that is at least 80% identical to SEQ ID NO:1 and comprises an alanine substitution at position 253, wherein numbering of positions is relative to SEQ ID NO:1, and which modified recombinant polymerase exhibits polymerase activity.

2. The composition of claim 1, wherein the modified recombinant polymerase comprises an amino acid sequence that is at least 90% identical to SEQ ID NO:1.

3. The composition of claim 1, wherein the modified recombinant polymerase is a modified recombinant Φ29, PZA, or M2Y polymerase.

4. The composition of claim 1, wherein the modified recombinant polymerase is an exonuclease deficient polymerase.

5. The composition of claim 1, comprising a phosphate-labeled nucleotide analog.

6. The composition of claim 5, wherein the nucleotide analog comprises a fluorophore.

7. The composition of claim 1, comprising a phosphate-labeled nucleotide analog and a DNA template, wherein the modified recombinant polymerase incorporates the nucleotide analog into a copy nucleic acid in response to the DNA template.

8. The composition of claim 1, wherein the composition is present in a DNA sequencing system.

9. The composition of claim 8, wherein the sequencing system comprises a zero mode waveguide.

10. The composition of claim 1, wherein the modified recombinant polymerase is immobilized on a surface.

11. The composition of claim 1, wherein the modified recombinant polymerase comprises an amino acid sequence that is at least 95% identical to SEQ ID NO:1.

12. A method of making a DNA, the method comprising:
   a) providing a reaction mixture comprising:
      a template,
      a replication initiating moiety that complexes with or is integral to the template,
      the modified recombinant DNA polymerase of claim 1, which polymerase is capable of replicating at least a portion of the template using the moiety in a template-dependent polymerase reaction, and
      one or more nucleotides and/or nucleotide analogs; and
   b) reacting the mixture such that the polymerase replicates at least a portion of the template in a template-dependent manner, whereby the one or more nucleotides and/or nucleotide analogs are incorporated into the resulting DNA.

* * * * *